(12) United States Patent
Nishimura et al.

(10) Patent No.: US 9,880,466 B2
(45) Date of Patent: Jan. 30, 2018

(54) SALT, ACID GENERATOR, RESIN, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Takashi Nishimura, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/151,618

(22) Filed: May 11, 2016

(65) Prior Publication Data

US 2016/0334702 A1  Nov. 17, 2016

(30) Foreign Application Priority Data

May 12, 2015 (JP) .................................. 2015-097043

(51) Int. Cl.
| | |
|---|---|
| G03F 7/039 | (2006.01) |
| G03F 7/004 | (2006.01) |
| C07C 309/17 | (2006.01) |
| C07C 381/12 | (2006.01) |
| C07D 327/06 | (2006.01) |
| G03F 7/38 | (2006.01) |
| C08F 222/10 | (2006.01) |

(52) U.S. Cl.
CPC .......... *G03F 7/0045* (2013.01); *C07C 309/17* (2013.01); *C07C 381/12* (2013.01); *C07D 327/06* (2013.01); *G03F 7/0046* (2013.01); *G03F 7/0397* (2013.01); *C07C 2603/74* (2017.05); *C08F 2222/1013* (2013.01); *G03F 7/38* (2013.01)

(58) Field of Classification Search
None
See application file for complete search history.

(56) References Cited

U.S. PATENT DOCUMENTS

| | | | |
|---|---|---|---|
| 3,779,778 A | 12/1973 | Smith et al. | |
| 3,849,137 A | 11/1974 | Barzynski et al. | |
| 4,576,902 A | 3/1986 | Saenger et al. | |
| 4,822,716 A | 4/1989 | Onishi et al. | |
| 4,857,437 A | 8/1989 | Banks et al. | |
| 5,017,453 A | 5/1991 | Onishi et al. | |
| 5,073,476 A | 12/1991 | Meier et al. | |
| 5,198,520 A | 3/1993 | Onishi et al. | |
| 5,260,410 A | 11/1993 | Schwalm | |
| 5,453,341 A | 9/1995 | Schwalm | |
| 7,049,044 B2 * | 5/2006 | Gonsalves | C08G 77/442 430/270.1 |
| 8,906,589 B2 * | 12/2014 | Ichikawa | C07C 25/18 430/270.1 |
| 2002/0098441 A1 | 7/2002 | Okino et al. | |
| 2003/0149225 A1 | 8/2003 | Okino et al. | |
| 2004/0043324 A1 | 3/2004 | Okino et al. | |
| 2005/0031990 A1 | 2/2005 | Okino et al. | |
| 2005/0031991 A1 | 2/2005 | Okino et al. | |
| 2005/0037283 A1 | 2/2005 | Okino et al. | |
| 2005/0037284 A1 | 2/2005 | Okino et al. | |
| 2005/0048400 A1 | 3/2005 | Okino et al. | |
| 2008/0193874 A1 | 8/2008 | Takata et al. | |
| 2010/0035180 A1 | 2/2010 | Shimada et al. | |
| 2010/0151380 A1 | 6/2010 | Ando et al. | |
| 2010/0203446 A1 | 8/2010 | Ichikawa et al. | |
| 2011/0171576 A1 | 7/2011 | Yamaguchi et al. | |
| 2011/0200935 A1 | 8/2011 | Masuyama et al. | |
| 2011/0201823 A1 | 8/2011 | Yoshida et al. | |
| 2011/0269074 A1 | 11/2011 | Aqad et al. | |
| 2012/0264060 A1 * | 10/2012 | Ichikawa | C07C 309/12 430/285.1 |
| 2012/0328986 A1 | 12/2012 | Anryu et al. | |
| 2013/0143157 A1 | 6/2013 | Tanaka et al. | |
| 2014/0255853 A1 | 9/2014 | Takaki et al. | |

FOREIGN PATENT DOCUMENTS

| | | |
|---|---|---|
| DE | 3914407 A1 | 10/1990 |
| EP | 0126712 A1 | 11/1984 |

(Continued)

OTHER PUBLICATIONS

Machine translation of JP 2013-082893 (2013).*
Gavina et al., "Non Concerted Pathways in the Generation of Dehydroarenes by Thermal Decomposition of Diaryliodonium Carboxylates", Tetrahedron, 1989, pp. 6281-6296, vol. 45, No. 19, Pergamon Press, Great Britain.

*Primary Examiner* — Martin Angebranndt
(74) *Attorney, Agent, or Firm* — Birch, Stewart, Kolasch & Birch, LLP

(57) ABSTRACT

A salt represented by formula (I):

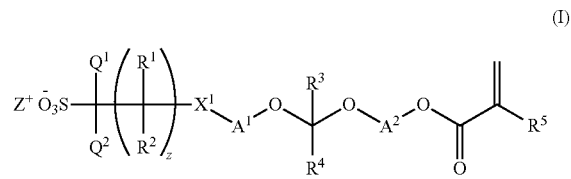

wherein $Q^1$ and $Q^2$ independently represent a fluorine atom or a $C_1$ to $C_6$ perfluoroalkyl group, $R^1$ and $R^2$ in each occurrence independently represent a hydrogen atom, a fluorine atom or a $C_1$ to $C_6$ perfluoroalkyl group, z represents an integer of 0 to 6, $X^1$ represents *—CO—O—, *—O—CO— or —O—, * represents a binding position to $C(R^1)(R^2)$ or $C(Q^1)(Q^2)$, $A^1$ represents a $C_4$ to $C_{24}$ hydrocarbon group having a $C_4$ to $C_{18}$ divalent alicyclic hydrocarbon moiety, $A^2$ represents a $C_2$ to $C_{12}$ divalent hydrocarbon group, $R^3$ and $R^4$ independently represent a hydrogen atom or a $C_1$ to $C_6$ monovalent saturated hydrocarbon group, $R^5$ represents a hydrogen atom, a fluorine atom, or a $C_1$ to $C_6$ alkyl group where a hydrogen atom may be replaced by a fluorine atom, and $Z^+$ represents an organic cation.

7 Claims, No Drawings

(56) References Cited

FOREIGN PATENT DOCUMENTS

| | | | |
|---|---|---|---|
| JP | 55-164824 A | | 12/1980 |
| JP | 62-69263 A | | 3/1987 |
| JP | 62-153853 A | | 7/1987 |
| JP | 63-26653 A | | 2/1988 |
| JP | 63-146029 A | | 6/1988 |
| JP | 63-146038 A | | 6/1988 |
| JP | 63-163452 A | | 7/1988 |
| JP | 2000-122294 A | | 4/2000 |
| JP | 2008-209917 A | | 9/2008 |
| JP | 2010-61117 A | | 3/2010 |
| JP | 2010-204634 A | | 9/2010 |
| JP | 2010-204646 A | | 9/2010 |
| JP | 2011-39502 A | | 2/2011 |
| JP | 2011-191745 A | | 9/2011 |
| JP | 2011-215619 A | | 10/2011 |
| JP | 2012-6908 A | | 1/2012 |
| JP | 2012-41274 A | | 3/2012 |
| JP | 2012-72109 A | | 4/2012 |
| JP | 2012-229206 A | | 11/2012 |
| JP | 2013-082893 | * | 5/2013 |
| JP | 2013-166748 | * | 8/2013 |
| JP | 2013-190782 | * | 9/2013 |
| JP | 2014-197168 A | | 10/2014 |

* cited by examiner

SALT, ACID GENERATOR, RESIN, RESIST COMPOSITION AND METHOD FOR PRODUCING RESIST PATTERN

CROSS-REFERENCE TO RELATED APPLICATIONS

This application claims priority to Japanese Application No. 2015-097043 filed on May 12, 2015. The entire disclosures of Japanese Application No. 2015-097043 is incorporated hereinto by reference.

BACKGROUND

1. Field of the Invention

The present disclosure relates to a salt, an acid generator, a resin, a resist composition and a method for producing resist pattern.

2. Related Art

A method for synthesizing a salt represented by the following formula is described in Patent document of JP 2011-215619A.

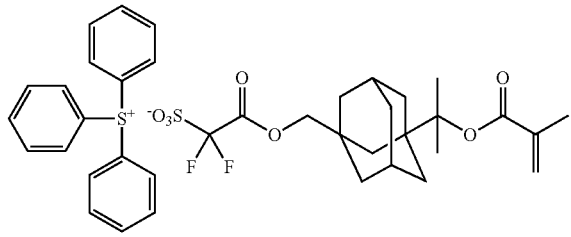

A resist composition which contains a resin having a structural unit derived from a salt represented by the following formula is described in Patent document of JP2014-197168A.

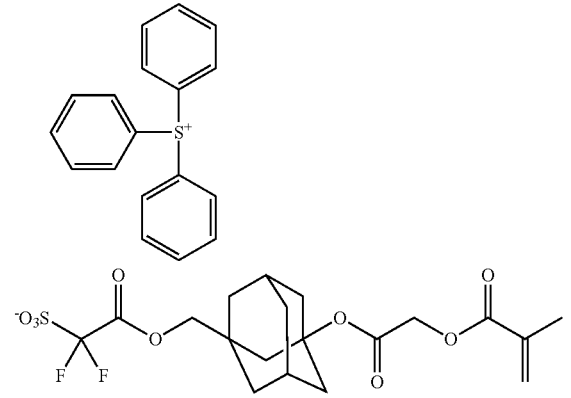

SUMMARY

The present disclosure provides the inventions as follows.

[1] A salt represented by formula (I):

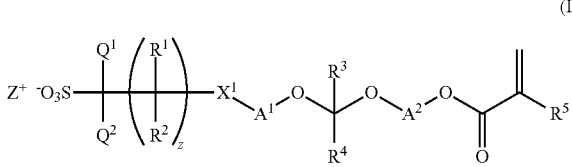

(I)

wherein $Q^1$ and $Q^2$ independently represent a fluorine atom or a $C_1$ to $C_6$ perfluoroalkyl group, $R^1$ and $R^2$ in each occurrence independently represent a hydrogen atom, a fluorine atom or a $C_1$ to $C_6$ perfluoroalkyl group, z represents an integer of 0 to 6, $X^1$ represents *—CO—O—, *—O—CO— or —O—, * represents a binding position to $C(R^1)(R^2)$ or $C(Q^1)(Q^2)$, $A^1$ represents a $C_4$ to $C_{24}$ hydrocarbon group having a $C_4$ to $C_{18}$ divalent alicyclic hydrocarbon moiety, $A^2$ represents a $C_2$ to $C_{12}$ divalent hydrocarbon group, $R^3$ and $R^4$ independently represent a hydrogen atom or a $C_1$ to $C_6$ monovalent saturated hydrocarbon group, $R^5$ represents a hydrogen atom, a fluorine atom, or a $C_1$ to $C_6$ alkyl group where a hydrogen atom may be replaced by a fluorine atom, and $Z^+$ represents an organic cation.

[2] The salt according to [1], wherein $X^1$ is *—CO—O—, where * represents a binding position to $C(R^1)(R^2)$ or $C(Q^1)(Q^2)$.

[3] The salt according to [1] or [2], wherein $A^1$ is a hydrocarbon group having an adamantanediyl moiety.

[4] The salt according to any one of [1] to [3], wherein $A^2$ is a $C_2$ to $C_6$ alkanediyl group.

[5] An acid generator comprising the salt according to any one of [1] to [4].

[6] A resin comprising a structural unit derived from the salt according to any one of [1] to [4].

[7] The resin according to [6], further comprising a structural unit having an acid-labile group, which structural unit being different from the structural unit derived from the salt represented by formula (I).

[8] The resin according to [6] or [7], wherein the structural unit having an acid-labile group is at least one selected from the group consisting of a structural unit represented by formula (a1-1) and a structural unit represented by formula (a1-2):

(a1-1)

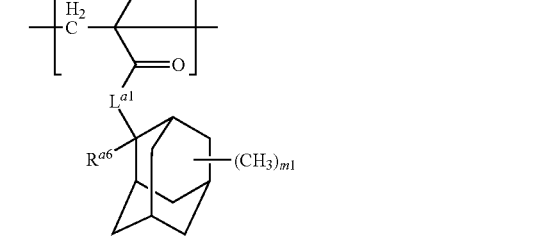

(a1-2)

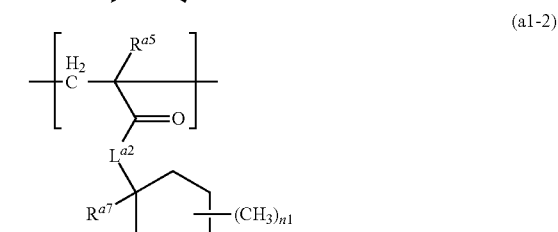

wherein $L^{a1}$ and $L^{a2}$ independently represent —O— or *—O—$(CH_2)_{k1}$—CO—O—, k1 represents an integer of 1 to 7,

* represents a binding position to —CO—, $R^{a4}$ and $R^{a5}$ independently represent a hydrogen atom or a methyl group, $R^{a6}$ and $R^{a7}$ independently represent a $C_1$ to $C_8$ alkyl group, a $C_3$ to $C_{18}$ alicyclic hydrocarbon group or a combination thereof, m1 represents an integer of 0 to 14, n1 represents an integer of 0 to 10, and n1' represents an integer of 0 to 3.

[9] A resist composition comprising the resin according to any one of [6] to [8] and an acid generator.

[10] The resist composition according to [9], wherein the acid generator is the acid generator according to [5].

[11] A resist composition comprising:

a resin having a structural unit having an acid-labile group, which structural unit being different from the structural unit derived from the a represented by formula (I), and the acid generator according to [5].

[12] The resist composition according to any one of [9] to [11]:

the acid generator further comprising a salt represented by formula (B1):

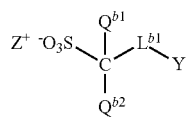
(B1)

wherein $Q^{b1}$ and $Q^{b2}$ respectively represent a fluorine atom or a $C_1$ to $C_6$ perfluoroalkyl group, $L^{b1}$ represents a $C_1$ to $C_{24}$ divalent saturated hydrocarbon group where a methylene group may be replaced by an oxygen atom or a carbonyl group and where a hydrogen atom may be replaced by a hydroxyl group or fluorine atom, and Y represents an optionally substituted methyl group, or an optionally substituted $C_3$ to $C_{18}$ alicyclic hydrocarbon group where a methylene group may be replaced by an oxygen atom, a carbonyl group or a sulfonyl group, and $Z^+$ represents an organic cation.

[13] The resist composition according to any one of [9] to [12] further comprising a salt which generates an acid lower in acidity than an acid generated from the acid generator.

[14] A method for producing a resist pattern comprising steps (1) to (5), (1) applying the resist composition according to any one of [9] to [13] onto a substrate;

(2) drying the applied composition to form a composition layer;

(3) exposing the composition layer;

(4) heating the exposed composition layer, and (5) developing the heated composition layer.

DETAILED DESCRIPTION OF DISCLOSURE

In the specification, the term "(meth)acrylic monomer" means a monomer having a structure of "$CH_2$=CH—CO—" or "$CH_2$=C($CH_3$)—CO—", as well as "(meth)acrylate" and "(meth)acrylic acid" mean "an acrylate or methacrylate" and "an acrylic acid or methacrylic acid," respectively. The group described herein, which can take both the linear structure and branch structure, may be either. When stereo isomers exist, it includes all stereoisomers. The indefinite articles "a" and "an" are taken as the same meaning as "one or more".

The term "solid components" means components other than solvents in a resist composition.

<Salt (I)>

The salt of the present disclosure is a salt represented by formula (I), which is sometimes referred to as "salt (I)".

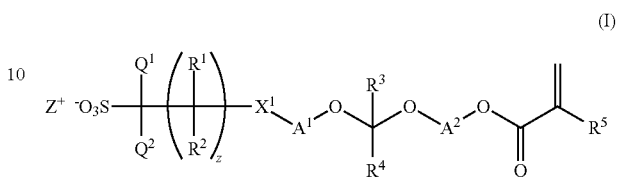
(I)

In the formula, wherein $Q^1$ and $Q^2$ independently represent a fluorine atom or a $C_1$ to $C_6$ perfluoroalkyl group, $R^1$ and $R^2$ in each occurrence independently represent a hydrogen atom, a fluorine atom or a $C_1$ to $C_6$ perfluoroalkyl group, z represents an integer of 0 to 6, $X^1$ represents *—CO—O—, *—O—CO— or *—O—, * represents a binding position to $C(R^1)(R^2)$ or $C(Q^1)(Q^2)$, $A^1$ represents a $C_4$ to $C_{24}$ hydrocarbon group having a $C_4$ to $C_{18}$ divalent alicyclic hydrocarbon moiety, $A^2$ represents a $C_2$ to $C_{12}$ divalent hydrocarbon group, $R^3$ and $R^4$ independently represent a hydrogen atom or a $C_1$ to $C_6$ monovalent saturated hydrocarbon group, $R^5$ represents a hydrogen atom, a fluorine atom, or a $C_1$ to $C_6$ alkyl group where a hydrogen atom may be replaced by a fluorine atom, and $Z^+$ represents an organic cation.

Examples of the perfluoroalkyl group for $Q^1$, $Q^2$, $R^1$ and $R^2$ include trifluoromethyl, perfluoroethyl, perfluoropropyl, perfluoro-isopropyl, perfluorobutyl, perfluoro-sec-butyl, perfluoro-tert-butyl, perfluoropentyl and perfluorohexyl groups.

$Q^1$ and $Q^2$ independently are preferably trifluoromethyl or fluorine atom, and more preferably a fluorine atom.

$R^1$ and $R^2$ independently are preferably a hydrogen atom or a fluorine atom.

z is preferably 0.

$X^1$ is preferably *—CO—O—, where * represents a binding position to $C(R^1)(R^2)$ or $C(Q^1)(Q^2)$.

Examples of the divalent hydrocarbon group represented by $A^1$ include a $C_4$ to $C_{18}$ divalent alicyclic hydrocarbon group, and a divalent group formed by combining a divalent alicyclic hydrocarbon group with a $C_1$ to $C_6$ alkanediyl group. The divalent hydrocarbon group of $A^1$ is 4 to 24, preferably 5 to 20, carbon atoms.

Examples of the alicyclic hydrocarbon group include cyclopentanediyl, cyclohexanediyl, adamantanediyl, and norbornanediyl groups. Among them, a cyclohexanediyl group and an adamantanediyl group are preferred, and an adamantanediyl group is more preferred.

Examples of the alkanediyl group include a chain alkanediyl group such as methylene, ethylene, propane-1,3-diyl, butane-1,4-diyl, pentane-1,5-diyl, and hexane-1,6-diyl groups, and a branched chain alkanediyl group such as ethane-1,1-diyl, propane-1,2-diyl, butane-1,3-diyl, 2-methylpropane-1,3-diyl, 2-methylpropane-1,2-diyl, pentane-1,4-diyl and 2-methylbutane-1,4-diyl groups.

$A^1$ is preferably a hydrocarbon group having an adamantanediyl moiety. Preferred examples of $A^1$ include an adamantanediyl group and a divalent group formed by combining an adamantanediyl group and alkanediyl group. As $A^1$, more preferred are an alkanediyl group as well as a divalent group formed by combining an adamantanediyl group and a methylene group, and still more preferred is a divalent group formed by combining an adamantanediyl group and a methylene group.

Examples of the divalent hydrocarbon group for $A^2$ include an alkanediyl group, a divalent alicyclic saturated hydrocarbon group, a divalent aromatic hydrocarbon group and a combination thereof.

Specific examples of the alkanediyl group include a chain alkanediyl group such as ethylene, propane-1,3-diyl, butane-1,4-diyl, pentane-1,5-diyl and hexane-1,6-diyl groups, and a branched chain alkanediyl group such as ethane-1,1-diyl, propane-1,2-diyl, butane-1,3-diyl, 2-methylpropane-1,3-diyl, 2-methylpropane-1,2-diyl, pentane-1,4-diyl and 2-methylbutane-1,4-diyl groups.

Specific examples of the alicyclic hydrocarbon group include cyclopentanediyl, cyclohexanediyl, adamantanediyl and norbornanediyl groups. Among them, a cyclohexanediyl group and an adamantanediyl group are preferred, and an adamantanediyl group is more preferred.

Specific examples of the aromatic hydrocarbon group include an aryl group such as phenylene, naphthylene, p-methylphenylene, p-tert-butylphenylene, tolylene, xylylene, cumenylene, mesitylene, biphenylene, 2,6-diethylphenylene and 2-methyl-6-ethylphenylene groups.

$A^2$ is preferably a $C_2$ to $C_6$ alkanediyl group, and more preferably a $C_2$ to $C_4$ alkanediyl group.

Examples of the monovalent hydrocarbon group for $R^3$ and $R^4$ include an alkyl group such as methyl, ethyl, propyl, butyl, isobutyl, sec-butyl, tert-butyl, pentyl and hexyl groups: a cycloalkane group such as cyclopentyl and cyclohexyl groups: and a combination thereof.

$R^3$ and $R^4$ are independently preferably a hydrogen atom, a methyl group and an ethyl group, more preferably a hydrogen atom and a methyl group, and still more preferably one of $R^3$ and $R^4$ being a hydrogen atom, and the other being a methyl group.

Examples of the alkyl group for $R^5$ include methyl, ethyl, n-propyl, isopropyl, n-butyl, sec-butyl, tert-butyl, n-pentyl and n-hexyl groups. $R^5$ is preferably a $C_1$ to $C_4$ alkyl group, and more preferably a methyl group and an ethyl group.

Examples of the halogen atom for $R^5$ include fluorine, chlorine, bromine and iodine atoms.

Examples of the alkyl group having a halogen atom for $R^5$ include trifluoromethyl, perfluoroethyl, perfluoropropyl, perfluoroisopropyl, perfluorobutyl, perfluoro sec-butyl, perfluoro tert-butyl, perfluoropentyl, perfluorohexyl, perchloromethyl, perbromomethyl and periodomethyl groups.

$R^5$ is preferably a hydrogen atom or a methyl group.

Specific examples of the anion in the salt (I) include the following ones. Among them, the anions represented by formulae (Ia-1) to (Ia-10) are preferred, and the anions represented by formulae (Ia-1) to (Ia-4) are more preferred.

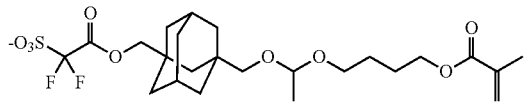
(Ia-1)

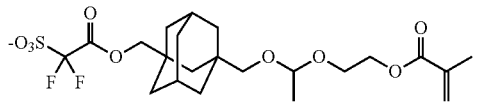
(Ia-2)

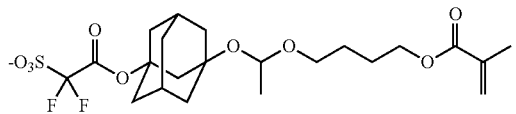
(Ia-3)

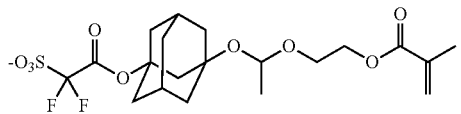
(Ia-4)

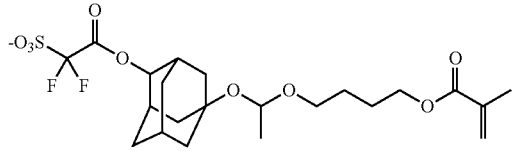
(Ia-5)

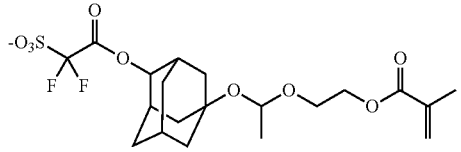
(Ia-6)

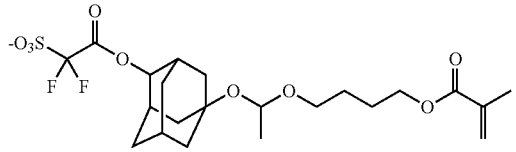
(Ia-7)

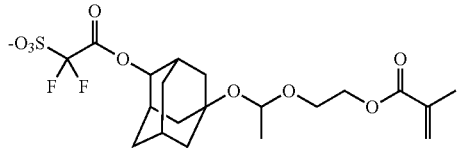
(Ia-8)

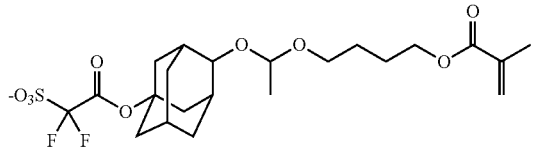
(Ia-9)

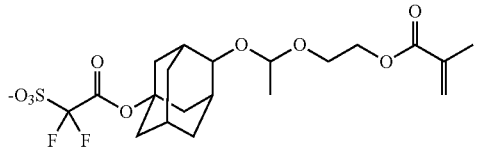
(Ia-10)

-continued

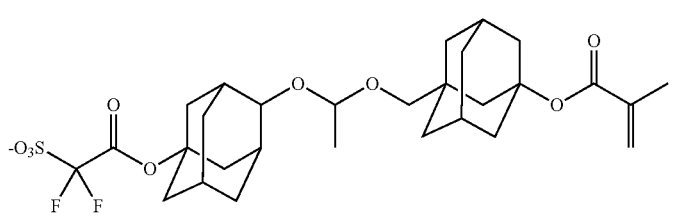
(Ia-11)

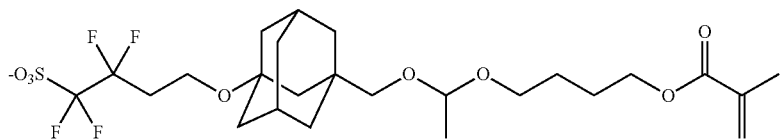
(Ia-12)

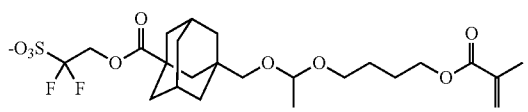
(Ia-13)

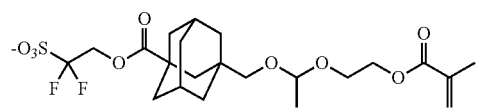
(Ia-14)

Examples of the organic cation represented by $Z^+$ include an organic onium cation such as an organic sulfonium cation, an organic iodonium cation, an organic ammonium cation, a benzothiazolium cation and an organic phosphonium cation, and an organic sulfonium cation and an organic iodonium cation are preferred, and an arylsulfonium cation is more preferred.

Among them, $Z^+$ is preferably a cation represented by any of formula (b2-1) to formula (b2-4):

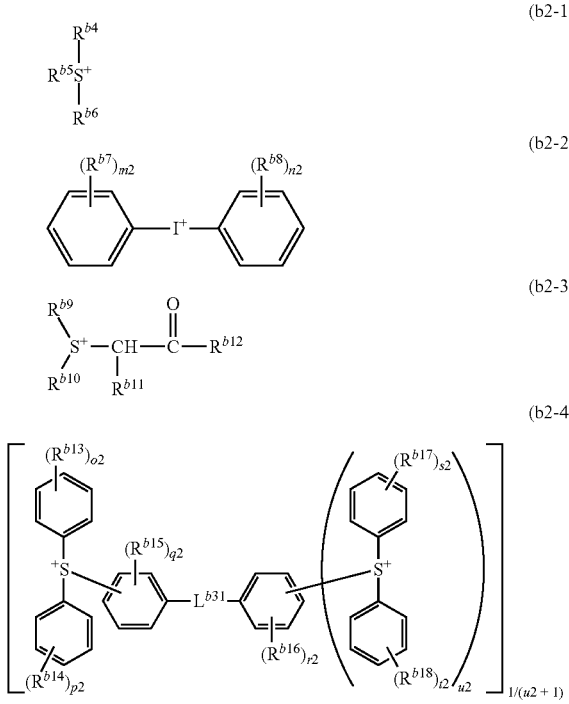

wherein $R^{b4}$, $R^{b5}$ and $R^{b6}$ independently represent a $C_1$ to $C_{30}$ aliphatic hydrocarbon group, a $C_3$ to $C_{36}$ alicyclic hydrocarbon group or a $C_6$ to $C_{36}$ aromatic hydrocarbon group, a hydrogen atom contained in an aliphatic hydrocarbon group may be replaced by a hydroxy group, a $C_1$ to $C_{12}$ alkoxy group, a $C_3$ to $C_{12}$ alicyclic hydrocarbon group or a $C_6$ to $C_{18}$ aromatic hydrocarbon group, a hydrogen atom contained in an alicyclic hydrocarbon group may be replaced by a halogen atom, a $C_1$ to $C_{18}$ aliphatic hydrocarbon group, a $C_2$ to $C_4$ acyl group or a glycidyloxy group, a hydrogen atom contained in an aromatic hydrocarbon group may be replaced by a halogen atom, a hydroxy group or a $C_1$ to $C_{12}$ alkoxy group, or $R^{b4}$ and $R^{b5}$ may be bonded together with a sulfur atom bonded thereto to form a sulfur-containing ring, a methylene group contained in the ring may be replaced by an oxygen atom, a sulfur atom or a carbonyl group;

$R^{b7}$ and $R^{b8}$ in each occurrence independently represent a hydroxy group, a $C_1$ to $C_{12}$ aliphatic hydrocarbon group or a $C_1$ to $C_{12}$ alkoxy group, m2 and n2 independently represent an integer of 0 to 5;

$R^{b9}$ and $R^{b10}$ independently represent a $C_1$ to $C_{36}$ aliphatic hydrocarbon group or a $C_3$ to $C_{36}$ alicyclic hydrocarbon group, or $R^{b9}$ and $R^{b10}$ may be bonded together with a sulfur atom bonded thereto to form a sulfur-containing ring, and a methylene group contained in the ring may be replaced by an oxygen atom, sulfur atom or a carbonyl group;

$R^{b11}$ represents a hydrogen atom, a $C_1$ to $C_{36}$ aliphatic hydrocarbon group, a $C_3$ to $C_{36}$ alicyclic hydrocarbon group or a $C_6$ to $C_{18}$ aromatic hydrocarbon group;

$R^{b12}$ represents a $C_1$ to $C_{12}$ aliphatic hydrocarbon group, a $C_3$ to $C_{18}$ alicyclic hydrocarbon group or a $C_6$ to $C_{18}$ aromatic hydrocarbon group, a hydrogen atom contained in an aliphatic hydrocarbon group may be replaced by a $C_6$ to $C_{18}$ aromatic hydrocarbon group, and a hydrogen atom contained in an aromatic hydrocarbon group may be replaced by a $C_1$ to $C_{12}$ alkoxy group or a $C_1$ to $C_{12}$ alkylcarbonyloxy group;

$R^{b11}$ and $R^{b12}$ may be bonded together with —CH—CO— bonded thereto to form a ring, and a methylene group contained in the ring may be replaced by an oxygen atom, sulfur atom or a carbonyl group;

$R^{b13}$, $R^{b14}$, $R^{b15}$, $R^{b16}$, $R^{b17}$ and $R^{b18}$ in each occurrence independently represent a hydroxy group, a $C_1$ to $C_2$ aliphatic hydrocarbon group or a $C_1$ to $C_{12}$ alkoxy group;

$L^{b1}$ represents —S— or —O—;

o2, p2, s2 and t2 independently represent an integer of 0 to 5;

q2 or r2 independently represent an integer of 0 to 4; and u2 represents an integer of 0 or 1.

Examples of the aliphatic group preferably include methyl, ethyl, n-propyl, isopropyl, n-butyl, sec-butyl, tert-butyl, n-pentyl, n-hexyl, n-octyl and 2-ethylhexyl groups. Among them, the aliphatic hydrocarbon group of $R^{b9}$ to $R^{b12}$ is preferably a $C_1$ to $C_{12}$ aliphatic hydrocarbon group.

Examples of the alicyclic hydrocarbon group preferably include monocyclic groups such as a cycloalkyl group, i.e., cyclopropyl, cyclobutyl, cyclopentyl, cyclohexyl, cycloheptyl, cyclooctyl and cyclodecyl groups; and polycyclic hydrocarbon groups such as decahydronaphtyl, adamantyl and norbornyl groups as well as groups below.

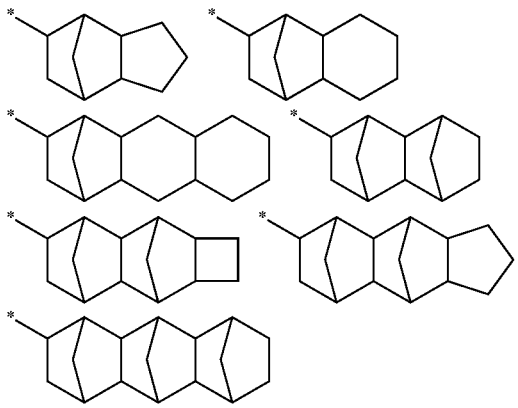

Among them, the alicyclic hydrocarbon group of $R^{b9}$ to $R^{b12}$ is preferably a $C_3$ to $C_{18}$ alicyclic hydrocarbon group, and more preferably a $C_4$ to $C_{12}$ alicyclic hydrocarbon group.

Examples of the alicyclic hydrocarbon group where a hydrogen atom has been replaced by an aliphatic hydrocarbon group include methylcyclohexyl, dimethylcyclohexyl, 2-alkyladamantanc-2-yl, methylnorbornyl and isobornyl groups. In the alicyclic hydrocarbon group where a hydrogen atom may be replaced by an aliphatic hydrocarbon group, the total carbon number of the alicyclic hydrocarbon group and the aliphatic hydrocarbon group is preferably 20 or less.

Examples of the aromatic hydrocarbon group preferably include an aryl group such as phenyl, tolyl, xylyl, cumenyl, mesityl, p-ethylphenyl, p-tert-butylphenyl, p-cyclohexylphenyl, p-adamantylphenyl, biphenyl, naphthyl, phenanthryl, 2,6-diethylphenyl and 2-methyl-6-ethylphenyl groups.

When the aromatic hydrocarbon includes an aliphatic hydrocarbon group or an alicyclic hydrocarbon group, a $C_1$ to $C_{18}$ aliphatic hydrocarbon group or a $C_3$ to $C_{18}$ alicyclic hydrocarbon group is preferred.

Examples of the aromatic hydrocarbon group where a hydrogen atom may be replaced by an alkoxy group include a p-methoxyphenyl group.

Examples of the aliphatic hydrocarbon group where a hydrogen atom may be replaced by an aromatic hydrocarbon group include an aralkyl group such as benzyl, phenethyl phenylpropyl, trityl, naphthylmethyl and naphthylethyl groups.

Examples of the alkoxy group include methoxy, ethoxy, propoxy, butoxy, pentyloxy, hexyloxy, heptyloxy, octyloxy, and dodecyloxy groups.

Examples of the acyl group include acetyl, propionyl and butyryl groups.

Examples of the halogen atom include fluorine, chlorine, bromine and iodine atoms.

Examples of the alkylcarbonyloxy group include methylcarbonyloxy, ethylcarbonyloxy, n-propylcarbonyloxy, isopropylcarbonyloxy, n-butylcarbonyloxy, sec-butylcarbonyloxy, tert-butyl carbonyloxy, pentylcarbonyloxy, hexylcarbonyloxy, octylcarbonyloxy and 2-ethylhexylcarobonyloxy groups.

The sulfur atom-containing ring which is formed by $R^{b4}$ and $R^{b5}$ may be a monocyclic or polycyclic one, which may be an aromatic or non-aromatic one, and which may be a saturated or unsaturated one. The ring is preferably a ring having 3 to 18 carbon atoms, and more preferably a ring having 4 to 13 carbon atoms. Examples of the sulfur atom-containing ring include a 3- to 12-membered ring, preferably a 3- to 7-membered ring, examples thereof include rings below.

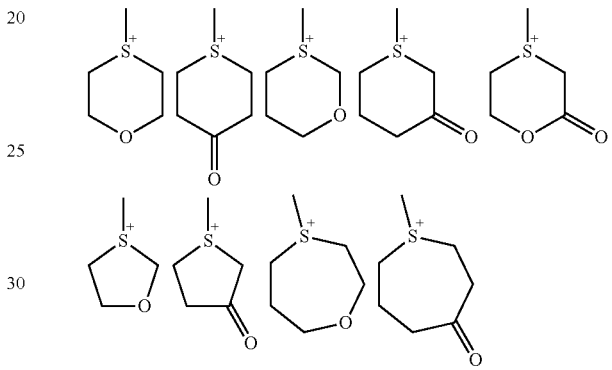

Examples of the ring formed by $R^{b9}$ and $R^{b10}$ may be any of monocyclic, polycyclic, aromatic, non-aromatic, saturated and unsaturated rings. The ring may be a 3- to 12-membered ring, preferably a 3- to 7-membered ring. Examples of the ring include thiolane-1-ium ring (tetrahydrothiophenium ring), thian-1-ium ring and 1,4-oxathian-4-ium ring.

Examples of the ring formed by $R^{b11}$ and $R^{b122}$ may be any of monocyclic, polycyclic, aromatic, non-aromatic, saturated and unsaturated rings. The ring may be a 3- to 12-membered ring, preferably a 3- to 7-membered ring. Examples of the ring include oxocycloheptane ring, oxocyclohexane ring, oxonorbornane ring and oxoadamantane ring.

Among the cations represented by formula (b2-1) to formula (b2-4), the cation represented by formula (b2-1) is preferred.

Examples of the cation represented by formula (b2-1) include the following ones.

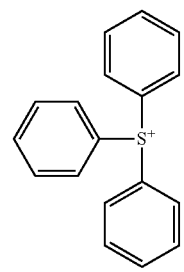

(b2-c-1)

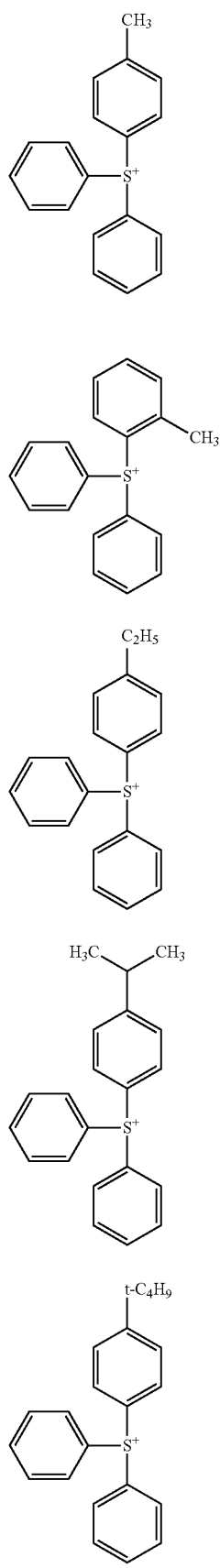
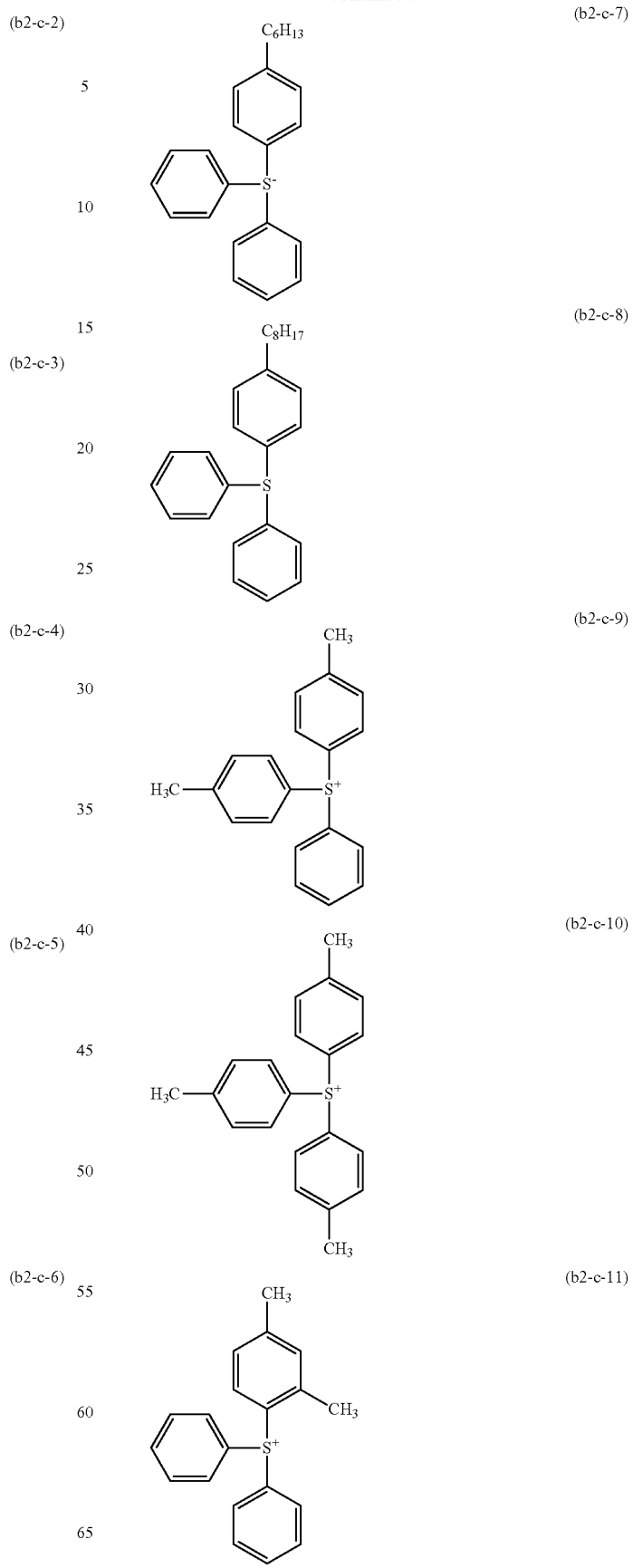

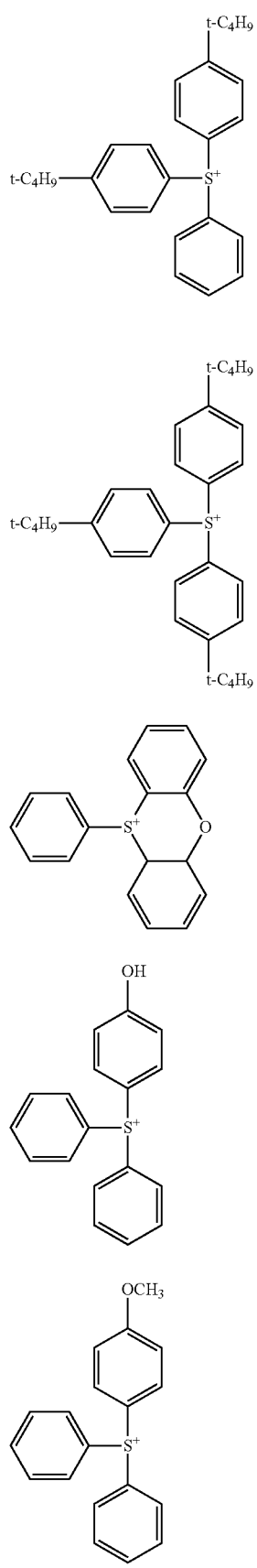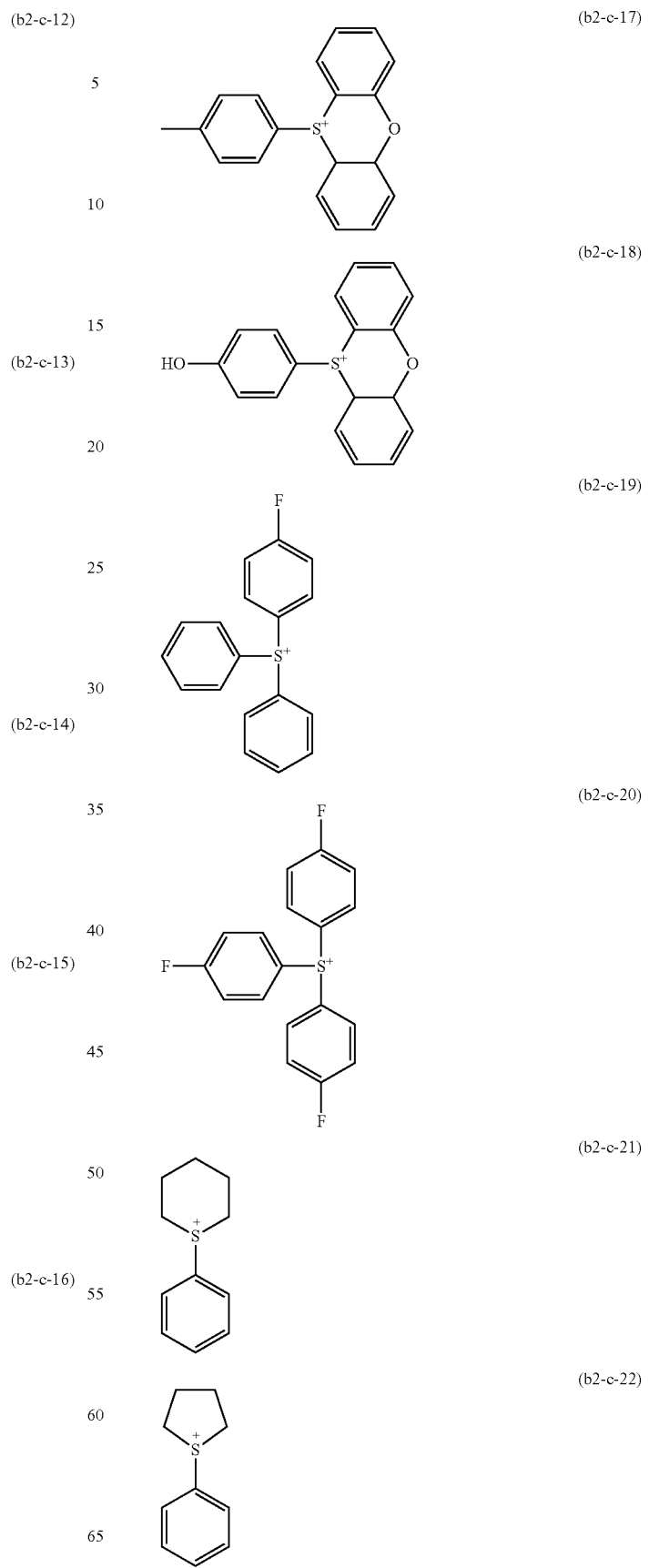

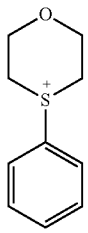
(b2-c-23)
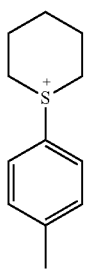
(b2-c-24)
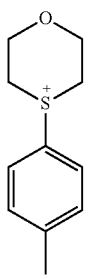
(b2-c-25)
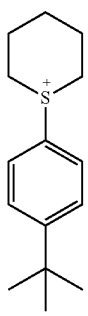
(b2-c-26)
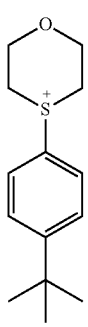
(b2-c-27)
Examples of the cation represented by formula (b2-2) include the following ones.
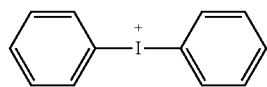
(b2-c-28)
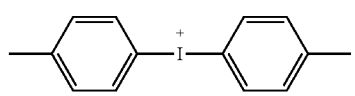
(b2-c-29)
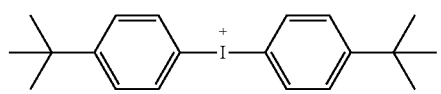
(b2-c-30)
Examples of the cation represented by formula (b2-3) include the following ones.
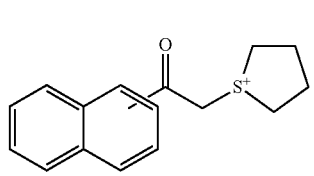
(b2-c-31)
(b2-c-32)
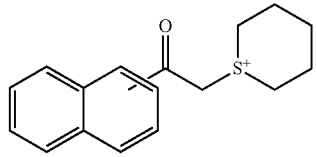
(b2-c-33)
(b2-c-34)
Examples of the cation represented by formula (b2-4) include the following ones.
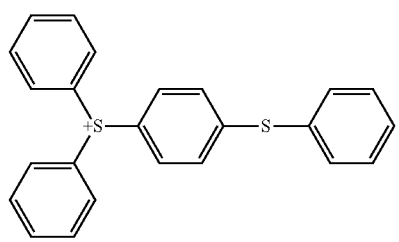

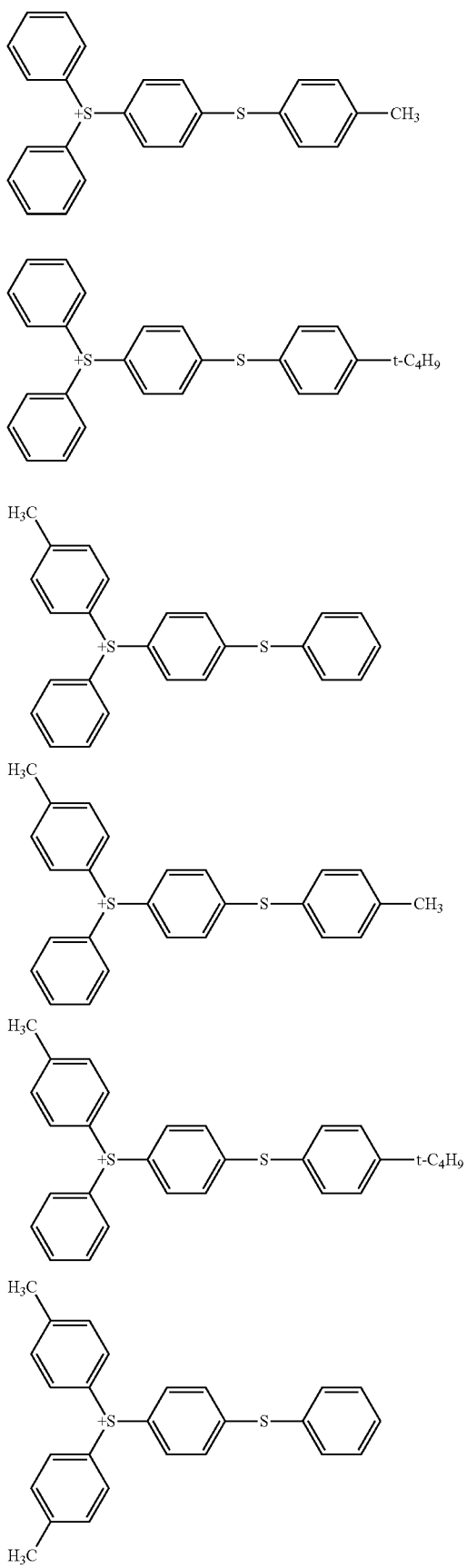
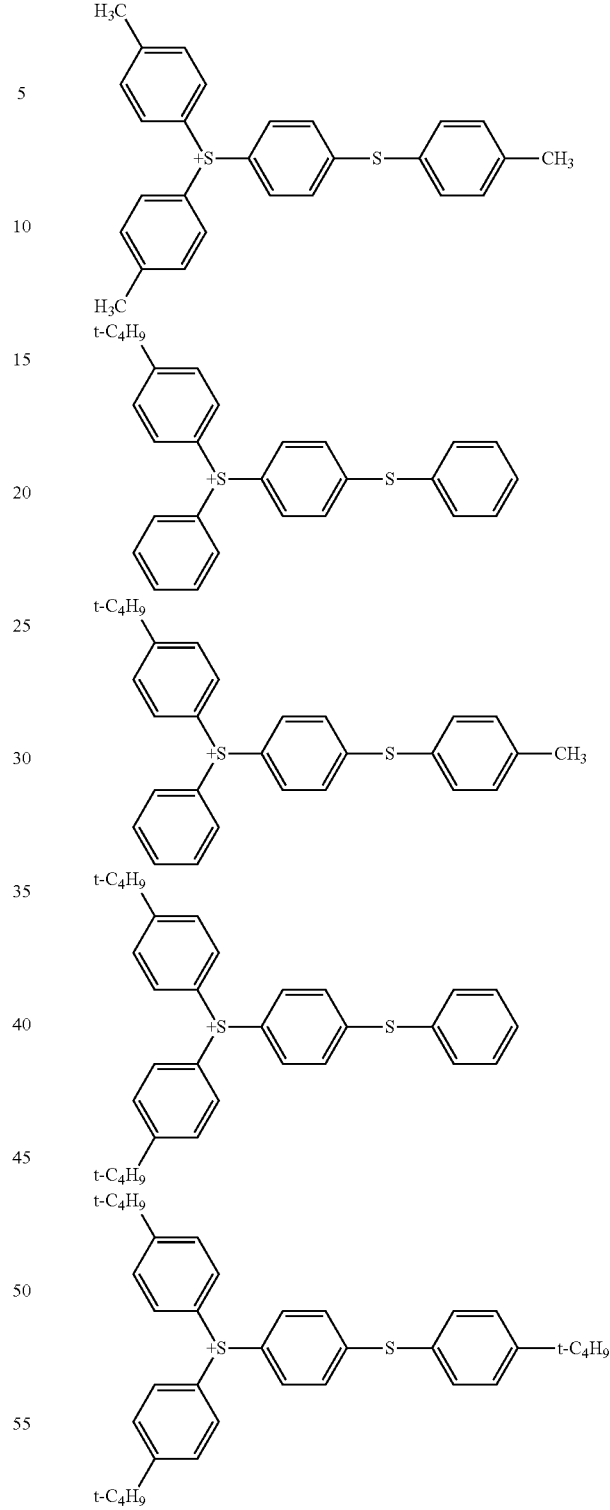

Preferred examples of the cations include those represented by formulae (b2-c-1), (b2-c-10), (b2-c-12), (b2-c-14), (b2-c-27), (b2-c-30) and (b2-c-31).

The salt (I) consists of one selected from among the above-mentioned sulfonic acid anions and one selected from among the above-mentioned organic cations. Specific examples of the salt (I) include salts illustrated in Table 1. In Table 1, the formulae representing the cation and anion which one salt is composed of are recited in the columns of the same raw as that of the salt. For example, the salt (I-1) is the salt consisting of the anion of formula (Ia-1) and the cation of formula (b2-c-1), which is represented below.

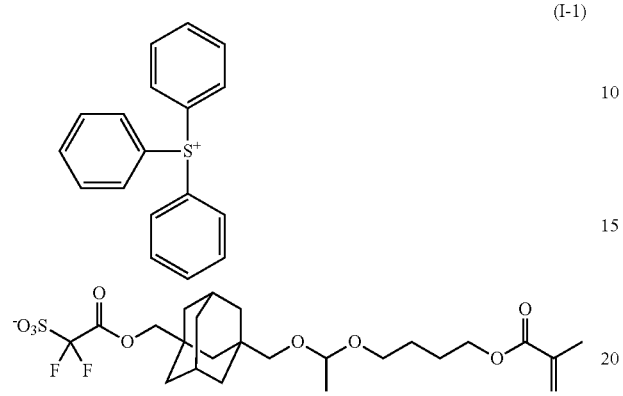

(I-1)

TABLE 1

| Salt (I) | Sulfonic Acid Anion | Organic Cation |
|---|---|---|
| (I-1) | (Ia-1) | (b2-c-1) |
| (I-2) | (Ia-2) | (b2-c-1) |
| (I-3) | (Ia-3) | (b2-c-1) |
| (I-4) | (Ia-4) | (b2-c-1) |
| (I-5) | (Ia-5) | (b2-c-1) |
| (I-6) | (Ia-6) | (b2-c-1) |
| (I-7) | (Ia-7) | (b2-c-1) |
| (I-8) | (Ia-8) | (b2-c-1) |
| (I-9) | (Ia-9) | (b2-c-1) |
| (I-10) | (Ia-10) | (b2-c-1) |
| (I-11) | (Ia-11) | (b2-c-1) |
| (I-12) | (Ia-12) | (b2-c-1) |
| (I-13) | (Ia-13) | (b2-c-1) |
| (I-14) | (Ia-14) | (b2-c-1) |
| (I-15) | (Ia-1) | (b2-c-10) |
| (I-16) | (Ia-2) | (b2-c-10) |
| (I-17) | (Ia-3) | (b2-c-10) |
| (I-18) | (Ia-4) | (b2-c-10) |
| (I-19) | (Ia-5) | (b2-c-10) |
| (I-20) | (Ia-6) | (b2-c-10) |
| (I-21) | (Ia-7) | (b2-c-10) |
| (I-22) | (Ia-8) | (b2-c-10) |
| (I-23) | (Ia-9) | (b2-c-10) |
| (I-24) | (Ia-10) | (b2-c-10) |
| (I-25) | (Ia-11) | (b2-c-10) |
| (I-26) | (Ia-12) | (b2-c-10) |
| (I-27) | (Ia-13) | (b2-c-10) |
| (I-28) | (Ia-14) | (b2-c-10) |
| (I-29) | (Ia-1) | (b2-c-12) |
| (I-30) | (Ia-2) | (b2-c-12) |
| (I-31) | (Ia-3) | (b2-c-12) |
| (I-32) | (Ia-4) | (b2-c-12) |
| (I-33) | (Ia-5) | (b2-c-12) |
| (I-34) | (Ia-6) | (b2-c-12) |
| (I-35) | (Ia-7) | (b2-c-12) |
| (I-36) | (Ia-8) | (b2-c-12) |
| (I-37) | (Ia-9) | (b2-c-12) |
| (I-38) | (Ia-10) | (b2-c-12) |
| (I-39) | (Ia-11) | (b2-c-12) |
| (I-40) | (Ia-12) | (b2-c-12) |
| (I-41) | (Ia-13) | (b2-c-12) |
| (I-42) | (Ia-14) | (b2-c-12) |
| (I-43) | (Ia-1) | (b2-c-14) |
| (I-44) | (Ia-2) | (b2-c-14) |
| (I-45) | (Ia-3) | (b2-c-14) |
| (I-46) | (Ia-4) | (b2-c-14) |
| (I-47) | (Ia-5) | (b2-c-14) |
| (I-48) | (Ia-6) | (b2-c-14) |
| (I-49) | (Ia-7) | (b2-c-14) |

TABLE 1-continued

| Salt (I) | Sulfonic Acid Anion | Organic Cation |
|---|---|---|
| (I-50) | (Ia-8) | (b2-c-14) |
| (I-51) | (Ia-9) | (b2-c-14) |
| (I-52) | (Ia-10) | (b2-c-14) |
| (I-53) | (Ia-11) | (b2-c-14) |
| (I-54) | (Ia-12) | (b2-c-14) |
| (I-55) | (Ia-13) | (b2-c-14) |
| (I-56) | (Ia-14) | (b2-c-14) |
| (I-57) | (Ia-1) | (b2-c-27) |
| (I-58) | (Ia-2) | (b2-c-27) |
| (I-59) | (Ia-3) | (b2-c-27) |
| (I-60) | (Ia-4) | (b2-c-27) |
| (I-61) | (Ia-5) | (b2-c-27) |
| (I-62) | (Ia-6) | (b2-c-27) |
| (I-63) | (Ia-7) | (b2-c-27) |
| (I-64) | (Ia-8) | (b2-c-27) |
| (I-65) | (Ia-9) | (b2-c-27) |
| (I-66) | (Ia-10) | (b2-c-27) |
| (I-67) | (Ia-11) | (b2-c-27) |
| (I-68) | (Ia-12) | (b2-c-27) |
| (I-69) | (Ia-13) | (b2-c-27) |
| (I-70) | (Ia-14) | (b2-c-27) |
| (I-71) | (Ia-1) | (b2-c-30) |
| (I-72) | (Ia-2) | (b2-c-30) |
| (I-73) | (Ia-3) | (b2-c-30) |
| (I-74) | (Ia-4) | (b2-c-30) |
| (I-75) | (Ia-5) | (b2-c-30) |
| (I-76) | (Ia-6) | (b2-c-30) |
| (I-77) | (Ia-7) | (b2-c-30) |
| (I-78) | (Ia-8) | (b2-c-30) |
| (I-79) | (Ia-9) | (b2-c-30) |
| (I-80) | (Ia-10) | (b2-c-30) |
| (I-81) | (Ia-11) | (b2-c-30) |
| (I-82) | (Ia-12) | (b2-c-30) |
| (I-83) | (Ia-13) | (b2-c-30) |
| (I-84) | (Ia-14) | (b2-c-30) |
| (I-85) | (Ia-1) | (b2-c-31) |
| (I-86) | (Ia-2) | (b2-c-31) |
| (I-87) | (Ia-3) | (b2-c-31) |
| (I-88) | (Ia-4) | (b2-c-31) |
| (I-89) | (Ia-5) | (b2-c-31) |
| (I-90) | (Ia-6) | (b2-c-31) |
| (I-91) | (Ia-7) | (b2-c-31) |
| (I-92) | (Ia-8) | (b2-c-31) |
| (I-93) | (Ia-9) | (b2-c-31) |
| (I-94) | (Ia-10) | (b2-c-31) |
| (I-95) | (Ia-11) | (b2-c-31) |
| (I-96) | (Ia-12) | (b2-c-31) |
| (I-97) | (Ia-13) | (b2-c-31) |
| (I-98) | (Ia-14) | (b2-c-31) |

Among them, salt (I) is preferably salt (I-1), salt (I-2), salt (I-3), salt (I-4), salt (I-15), salt (I-16), salt (I-17), salt (I-18), salt (I-29), salt (I-30), salt (I-31), salt (I-32), salt (I-43), salt (I-44), salt (I-45), salt (I-46), salt (I-57), salt (I-58), salt (I-59), salt (I-60), salt (I-71), salt (I-72), salt (I-73), salt (I-74), salt (I-85), salt (I-86), salt (I-87) and salt (I-88).

<Method for Producing the Salt (I)>

The salt represented by formula (I) can be produced by treating a compound represented by formula (I-b), for example, with sodium hydroxide and then reacting the treated one with a salt represented by formula (I-a) in a solvent. In the formula below, all symbols are as defined above.

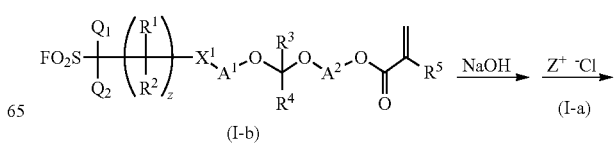

-continued

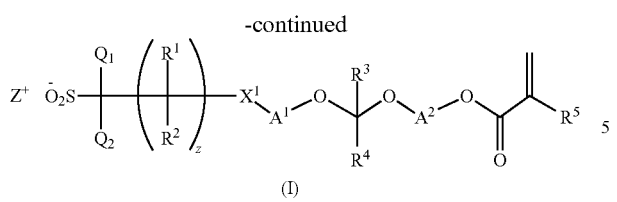

(I)

Examples of the solvent include chloroform, acetonitrile and ion exchanged water.

Examples of the salt represented by formula (I-a) include the compound represented by formula below which is available on the market.

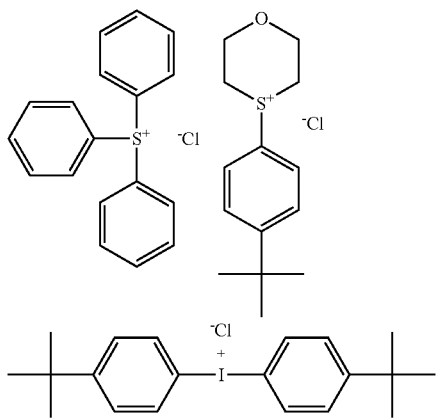

The reaction can be conducted at temperature of preferably −5° C. to 80° C., for 0.5 to 24 hours.

A variety of the salts represented formula (I) can be obtained by modifying one of the salts. For example, the salt (I) having an oxathianium cation can be obtained by reacting the salt (I) having diphenyliodonium with 1,4-oxathiane in the presence of dibenzoic acid copper (II).

The compound represented by formula (I-b) can be produced by reacting a compound represented by formula (I-c) with a compound represented by formula (I-d) in a solvent with in the presence of a catalyst.

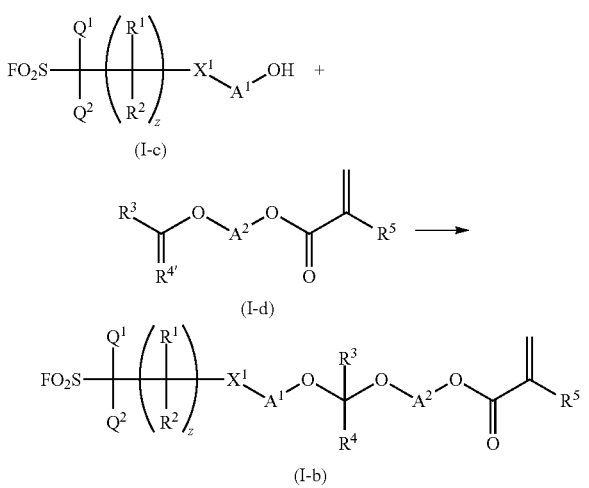

In the formula, $Q^1$, $Q^2$, $R^1$, $R^2$, $R^3$, $R^4$, $R^5$, $X^1$, $A^1$, $A^2$ and z are as defined above, and $R^{4'}$ represents the group in which one hydrogen atom has been removed from the group represented by $R^4$.

The reaction can be conducted at temperature of preferably 5° C. to 80° C., for 0.5 to 24 hours.

Examples of the solvent include chloroform and tetrahydrofuran.

Examples of the catalyst include a salt below.

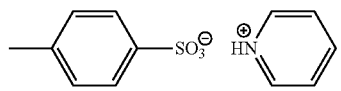

When $X^1$ is *—CO—O—, where * is a binding position to $CR^1R^2$ or $CQ^1R^2$, in the compound represented by formula (I-c), the compound, that is one represented by formula (I1-c), can be produced by reacting a salt represented by formula (I1-e) with a compound represented by formula (I1-f) in a solvent in the presence of a catalyst.

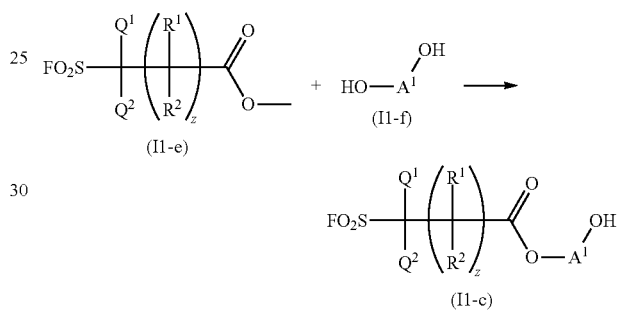

In the formula, $Q^1$, $Q^2$, $R^1$, $R^2$, $A^1$ and z are as defined above.

The reaction can be conducted at temperature of preferably 10° C. to 120° C., for 0.5 to 24 hours.

Examples of the solvent include chloroform and tetrahydrofuran.

Examples of the catalyst include a compound represented by formula $Ti(O-i-Pr)_4$.

Examples of the compound represented by formula (I1-e) include the compound represented by formula below which is available on the market.

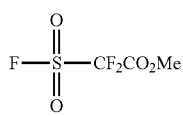

Examples of the compound represented by formula (I1-f) include the compound represented by formula below which is available on the market.

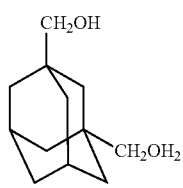

The compound represented by formula (I-d) can be produced by reacting a compound represented by formula (I-g) with a compound represented by formula (I-h) in a solvent in the presence of a catalyst.

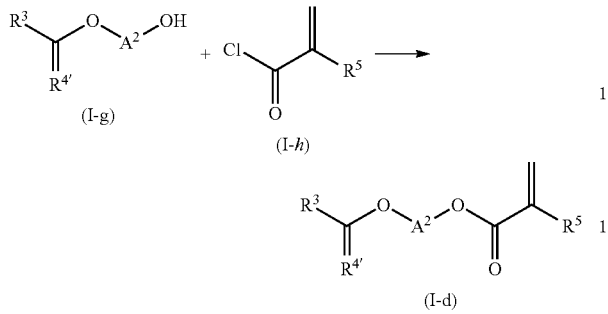

In the formula, $R^3$, $R^{4'}$, $R^5$ and $A^2$ are as defined above.

The reaction can be conducted at temperature of preferably −5° C. to 80° C., for 0.5 to 24 hours.

Examples of the solvent include chloroform and tetrahydrofuran.

Examples of the catalyst include a basic catalyst such as triethylamine.

Examples of the compound represented by formula (1-g) include the compound represented by formula below which is available on the market.

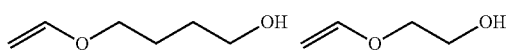

Examples of the compound represented by formula (1-h) include the compound represented by formula below which is available on the market.

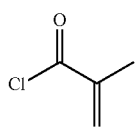

<Acid Generator>

The acid generator of the present disclosure contains the salt (I) generally as an active ingredient. The acid generator may contain one kind of the salt (I) or two or more kinds of the salt (I). The acid generator may contain the salt (I) in combination with a known acid generator in this art (which is sometimes referred to as "acid generator (B)") as an active ingredient.

When the acid generator contains the salt (I) and the acid generator (B), the weight ratio of the salt (I):the acid generator (B) may be 1:99 to 99:1, preferably 2:98 to 98:2, more preferably 5:95 to 95:5, still more preferably 10:90 to 40:60, and further still more preferably 15:85 to 30:70.

<Resin>

The resin of the present disclosure is a resin having a structural unit derived from the salt (I) (which is sometimes referred to as "structural unit (I)"), the resin is sometimes referred to as "resin (A)."

The resin may be a polymer having one kind of the structural unit (I) or two or more kinds of the structural unit (I).

The total proportion of the structural unit (I) is usually 0.1% by mole to 100% by mole, preferably 0.5% by mole to 50% by mole, more preferably 0.8% by mole to 30% by mole, and still more preferably 1% by mole to 10% by mole with respect to the total structural units (100% by mole) constituting the resin (A).

The resin (A) may further has a structural unit having an acid-labile group, which structural unit is different from the structural unit (I) (which is sometimes referred to as "structural unit (a1)"). Here the "acid-labile group" means a group having a leaving group which is detached by contacting with an acid to thereby form a hydrophilic group such as a hydroxy or carboxy group.

The resin (A) preferably includes a structural unit other than the structural unit (a1). Examples of the structural unit other than the structural unit (a1) include a structural unit having no acid-labile group (which is sometimes referred to as "structural unit (s)").

<Structural Unit (a1)>

The structural unit (a1) is derived from a monomer having an acid-labile group, which monomer is sometimes referred to as "monomer (a1)".

In the resin (A), the acid-labile group contained in the structural unit (a1) is preferably the following one of formula (1) and formula (2).

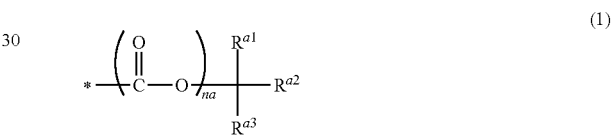

In the formula, $R^{a1}$ to $R^{a3}$ independently represent a $C_1$ to $C_8$ alkyl group, a $C_3$ to $C_{20}$ alicyclic hydrocarbon group or combination thereof, or $R^{a1}$ and $R^{a2}$ may be bonded together with a carbon atom bonded thereto to form a $C_3$ to $C_{20}$ divalent alicyclic hydrocarbon group, na represents an integer of 0 or 1, and

* represents a binding position.

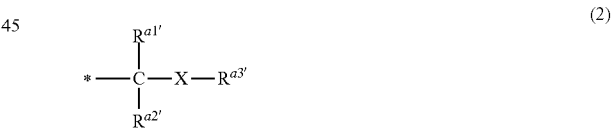

In the formula, $R^{a1'}$ and Re independently represent a hydrogen atom or a $C_1$ to $C_{12}$ hydrocarbon group, $R^{a3'}$ represents a $C_1$ to $C_{20}$ hydrocarbon group, or $R^{a2'}$ and $R^{a'}$ may be bonded together with a carbon atom and X bonded thereto to form a divalent $C_3$ to $C_{20}$ heterocyclic group, and a methylene group contained in the hydrocarbon group or the divalent heterocyclic group may be replaced by an oxygen atom or sulfur atom, X represents —O— or —S—, and

* represents a binding position.

Examples of the alkyl group for $R^{a1}$ to $R^{a3}$ include methyl, ethyl, propyl, n-butyl, n-pentyl, n-hexyl, n-heptyl and n-octyl groups.

Examples of the alicyclic hydrocarbon group for $R^{a1}$ to $R^{a3}$ include monocyclic groups such as a cycloalkyl group, i.e., cyclopentyl, cyclohexyl, cycloheptyl, cyclooctyl groups, and polycyclic hydrocarbon groups such as decahydronaphtyl, adamantyl and norbornyl groups as well as groups below. * represents a binding position.

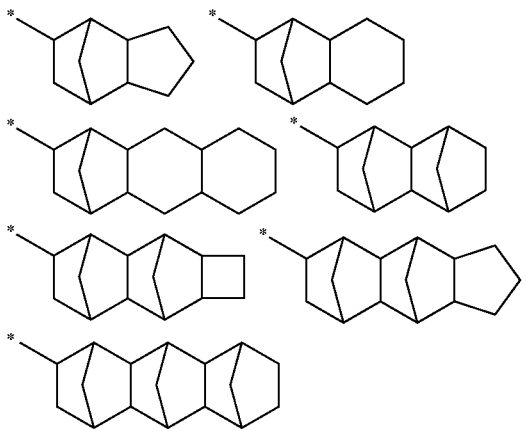

The alicyclic hydrocarbon group of $R^{a1}$ to $R^{a3}$ preferably has 3 to 16 carbon atoms.

Examples of groups combining the alkyl group and the alicyclic hydrocarbon group include methylcyclohexyl, dimethylcyclohexyl, methylnorbornyl, cyclohexylmethl, adamantylmethyl and norbornyletyl groups.

na is preferably an integer of 0.

When $R^{a1}$ and $R^{a2}$ are bonded together to form a divalent alicyclic hydrocarbon group, examples of the group represented by —C($R^{a1}$)($R^{a2}$)($R^{a3}$) include groups below. The divalent alicyclic hydrocarbon group preferably has 3 to 12 carbon atoms. * represent a binding position to —O—.

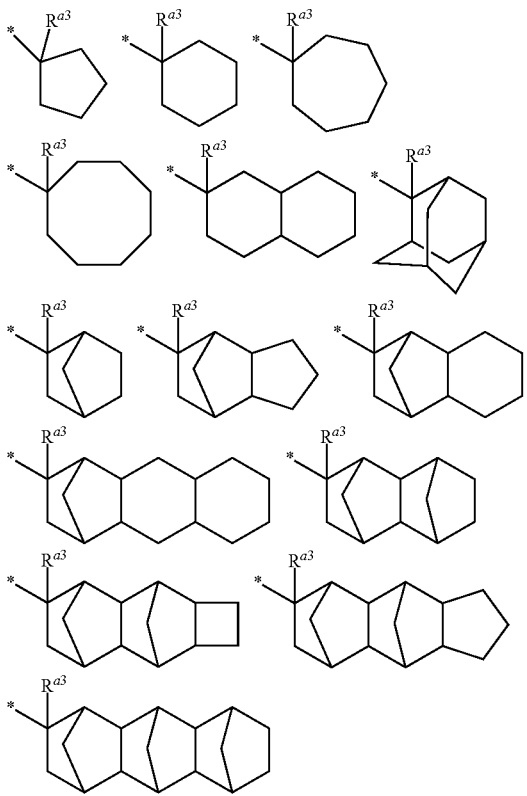

Specific examples of the group represented by formula (1) include 1,1-dialkylalkoxycarbonyl group (a group represented by formula (1) in which $R^{a1}$ to $R^{a3}$ are alkyl groups, preferably tert-butoxycarbonyl group), 2-alkyladamantane-2-yloxycarbonyl group (a group represented by formula (1) in which $R^{a1}$, $R^{a2}$ and a carbon atom form adamantyl group, and $R^{a3}$ is alkyl group), and 1-(adamantane-1-yl)-1-alkylalkoxycarbonyl group (a group represented by formula (1) in which $R^{a1}$ and $R^{a3}$ are alkyl group, and $R^{a3}$ is adamantyl group).

The hydrocarbon group for $R^{a1'}$ to $R^{a3'}$ includes an alkyl group, an alicyclic hydrocarbon group, an aromatic hydrocarbon group and a combination thereof.

Examples of the alkyl group and the alicyclic hydrocarbon group are the same examples as described above.

Examples of the aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the divalent heterocyclic group formed by binding with $R^{a2'}$ and $R^{a3'}$ include groups below. * represents a binding position.

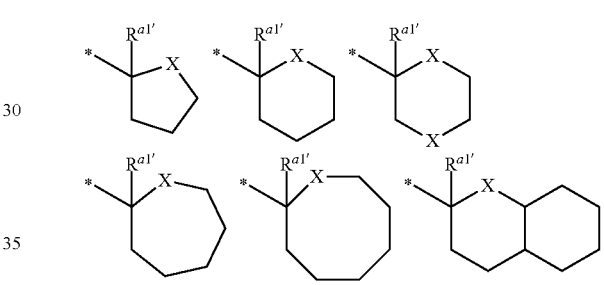

At least one of $R^{a1'}$ and $R^{a2'}$ is preferably a hydrogen atom.

Specific examples of the group represented by formula (2) include a group below. * represents a binding position.

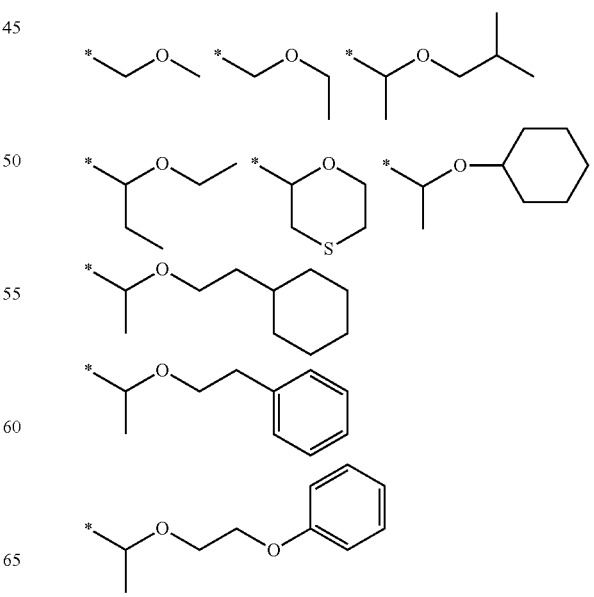

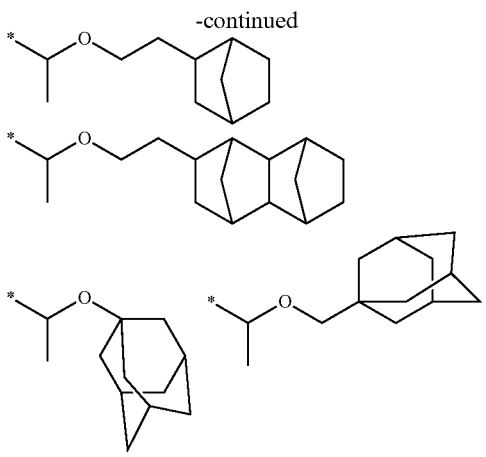

The monomer (a1) is preferably a monomer having an acid-labile group and an ethylene unsaturated bond, and more preferably a (meth)acrylic monomer having an acid-labile group.

Among the (meth)acrylic monomer having an acid-labile group, a monomer having a $C_5$ to $C_{20}$ alicyclic hydrocarbon group is preferred. When a resin (A) having a structural unit derived from a monomer (a1) having a bulky structure such as the alicyclic hydrocarbon group is used for a resist composition, the resist composition having excellent resolution tends to be obtained.

Examples of a structural unit derived from the (meth) acrylic monomer having the group represented by formula (1) preferably include structural units represented by formula (a1-0), formula (a1-1) and formula (a1-2) below. These may be used as one kind of the structural unit or as a combination of two or more kinds of the structural units. The structural unit represented by formula (a1-0), the structural unit represented by formula (a1-1) and a structural unit represented by formula (a1-2) are sometimes referred to as "structural unit (a1-0)", "structural unit (a1-1)" and "structural unit (a1-2)", respectively, and monomers deriving the structural unit (a1-0), the structural unit (a1-1) and the structural unit (a1-2) are sometimes referred to as "monomer (a1-0)", "monomer (a1-1)" and "monomer (a1-2)", respectively.

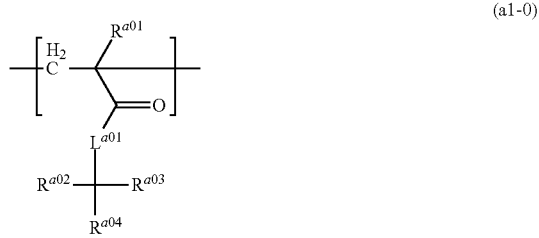

In the formula, $L^{a01}$ represents —O— or *—O—$(CH_2)_{k01}$—CO—O—.

k01 represents an integer of 1 to 7,

* represents a binding position to —CO—, $R^{a01}$ represents a hydrogen atom or a methyl group, and $R^{a02}$, $R^{a03}$ and $R^{a04}$ independently represent a $C_1$ to $C_8$ alkyl group, a $C_3$ to $C_{18}$ alicyclic hydrocarbon group or combination thereof.

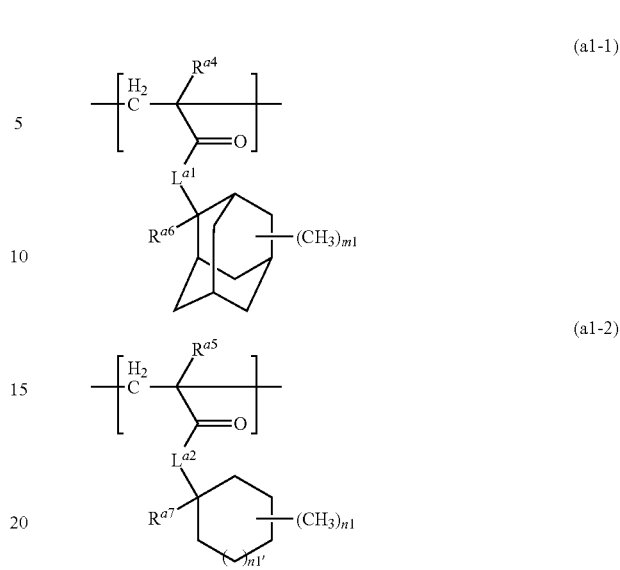

In the formula, $L^{a2}$ and $L^{a2}$ independently represent —O— or *—O—$(CH_2)_{k1}$—CO—O—, k1 represents an integer of 1 to 7,

* represents a binding position to —CO—, $R^{a4}$ and $R^{a5}$ independently represent a hydrogen atom or a methyl group, $R^{a6}$ and $R^{a7}$ independently represent a $C_1$ to $C_8$ alkyl group, a $C_3$ to $C_{18}$ alicyclic hydrocarbon group or a combination thereof, m1 represents an integer of 0 to 14, n1 represents an integer of 0 to 10, and n1' represents an integer of 0 to 3.

$L^{a01}$ is preferably an —O— or *—O—$(CH_2)_{k01}$—CO—O— in which k01 is preferably an integer of 1 to 4, more preferably an integer of 1, more preferably an —O—.

Examples of the alkyl group, an alicyclic hydrocarbon group and combination thereof for $R^{a02}$, $R^{a03}$ and $R^{a04}$ are the same examples as the group described in $R^{a1}$ to $R^{a3}$ in formula (1).

The alkyl group for $R^{a02}$, $R^{a03}$ and $R^{a04}$ is preferably a $C_1$ to $C_6$ alkyl group.

The alicyclic hydrocarbon group for $R^{a02}$, $R^{a03}$ and $R^{a04}$ is preferably a $C_3$ to $C_8$ alicyclic hydrocarbon group, more preferably a $C_3$ to $C_6$ alicyclic hydrocarbon group.

The group formed by combining the alkyl group and the alicyclic hydrocarbon group has preferably 18 or less of carbon atom. Examples of those groups include methylcyclohexyl, dimethylcyclohexyl, methylnorbornyl, methyladamantyl, cyclohexylmethyl, methyl cyclohexylmethyl, adamantylmethyl and norbornylmethy groups.

$R^{a02}$ and $R^{a03}$ is preferably a $C_1$ to $C_6$ alkyl group, more preferably a methyl group or an ethyl group.

$R^{a04}$ is preferably a $C_1$ to $C_6$ alkyl group or a $C_5$ to $C_{12}$ alicyclic hydrocarbon group, more preferably a methyl, ethyl, cyclohexyl or adamantyl group.

$L^{a1}$ and $L^{a2}$ are preferably —O— or *—O—$(CH_2)_{k1}$—CO—O— in which k1' represents an integer of 1 to 4 and more preferably 1, still more preferably —O—.

$R^{a4}$ and $R^{a5}$ are preferably a methyl group.

Examples of the alkyl group, an alicyclic hydrocarbon group and a combination thereof for $R^{a6}$ and $R^{a7}$ are the same examples as the group described in $R^{a1}$ to $R^{a3}$ in formula (1).

The alkyl group for $R^{a6}$ and $R^{a7}$ is preferably a $C_1$ to $C_6$ alkyl group.

The alicyclic hydrocarbon group for $R^{a6}$ and $R^{a7}$ is preferably a $C_3$ to $C_8$ alicyclic hydrocarbon group, more preferably a $C_3$ to $C_6$ alicyclic hydrocarbon group.

m1 is preferably an integer of 0 to 3, and more preferably 0 or 1.

n1 is preferably an integer of 0 to 3, and more preferably 0 or 1.

n1' is preferably 0 or 1, and more preferably 1.

Examples of the monomer (a1-0) preferably include monomers represented by formula (a1-0-1) to formula (a1-0-12), and more preferably monomers represented by formula (a1-0-1) to formula (a1-0-10) below.

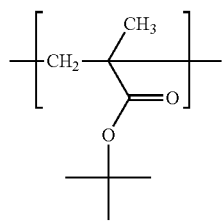
(a1-0-1)

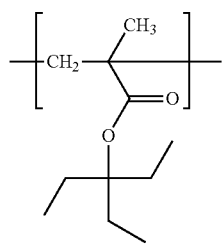
(a1-0-2)

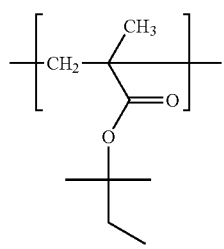
(a1-0-3)

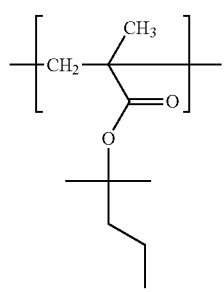
(a1-0-4)

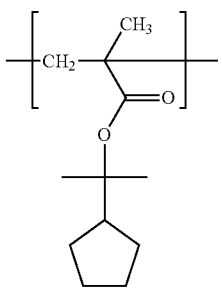
(a1-0-5)

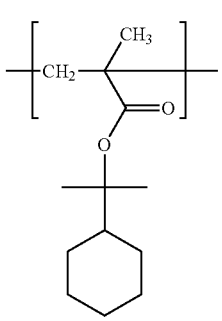
(a1-0-6)

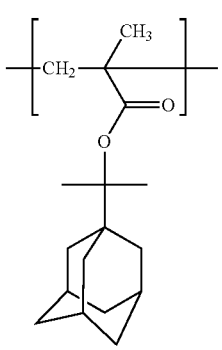
(a1-0-7)

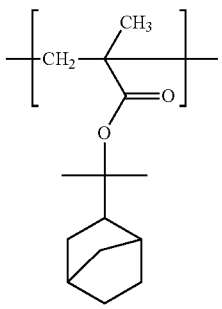
(a1-0-8)

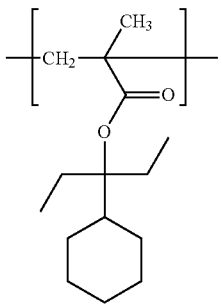
(a1-0-9)

(a1-0-10)
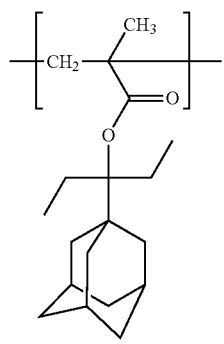

(a1-0-11)
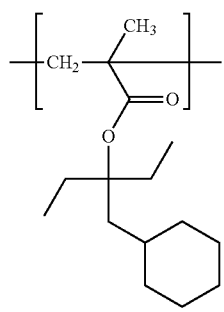

(a1-0-12)
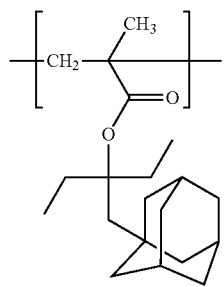

Examples of the structural units (a1-0) include structural units in which a methyl group corresponding to $R^{a01}$ in the structural units represented as above has been replaced by a hydrogen atom.

Examples of the monomer (a1-1) include monomers described in JP 2010-204646A. Among them, the monomers are preferably monomers represented by formula (a1-1-1) to formula (a1-1-8), and more preferably monomers represented by formula (a1-1-1) to formula (a1-1-4) below.

(a1-1-1)
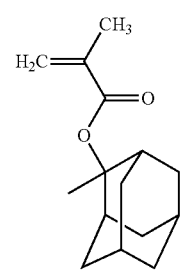

(a1-1-2)
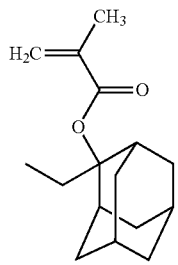

(a1-1-3)
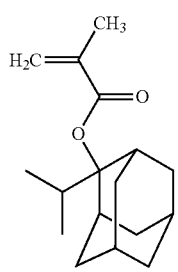

(a1-1-4)
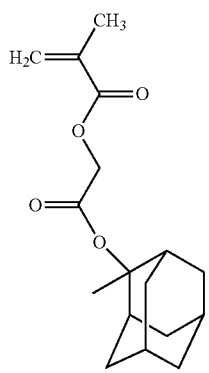

(a1-1-5)
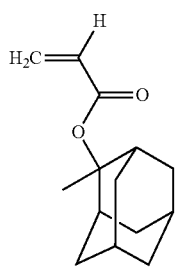

(a1-1-6)
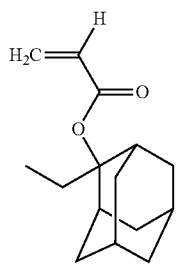

(a1-1-7)
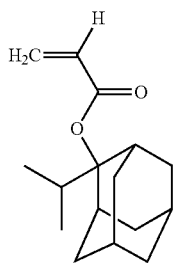

(a1-1-8)
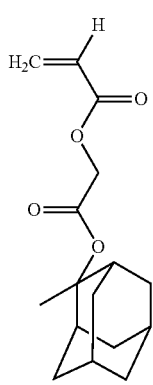

Examples of the monomer (a1-2) include 1-methylcyclopentane-1-yl (meth)acrylate, 1-ethylcyclopentane-1-yl (meth)acrylate, 1-methylcyclohexane-1-yl (meth)acrylate, 1-ethylcyclohexane-1-yl (meth)acrylate, 1-ethylcycloheptane-1-yl (meth)acrylate, 1-ethylcyclooctane-1-yl (meth)acrylate, 1-isopropylcyclopentane-1-yl (meth)acrylate and 1-isopropylcyclohexane-1-yl (meth)acrylate. Among them, the monomers are preferably monomers represented by formula (a1-2-1) to formula (a1-2-12), and more preferably monomers represented by formula (a1-2-3), formula (a1-2-4), formula (a1-2-9) and formula (a1-2-10), and still more preferably monomer represented by formula (a1-2-3) and formula (a1-2-9) below.

(a1-2-1)
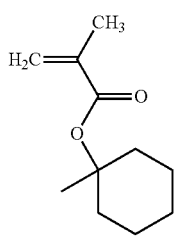

(a1-2-2)
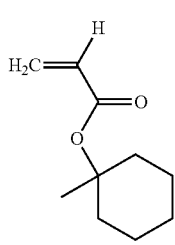

(a1-2-3)
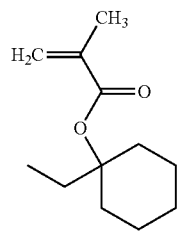

(a1-2-4)
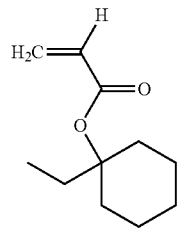

(a1-2-5)
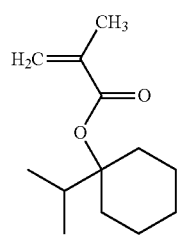

(a1-2-6)
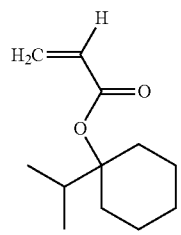

(a1-2-7)
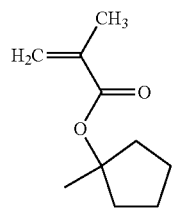

(a1-2-8)
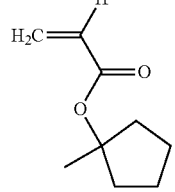

(a1-2-9)
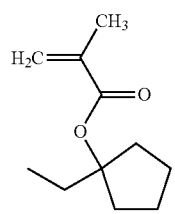

-continued

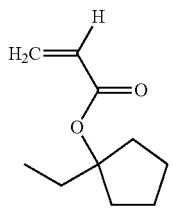
(a1-2-10)

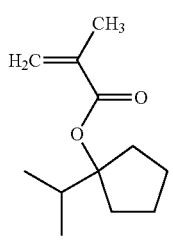
(a1-2-11)

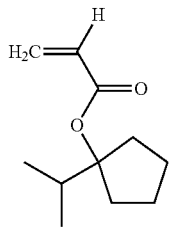
(a1-2-12)

When the resin (A) contains the structural unit (a1-0), the structural unit (a1-1) and/or the structural unit (a1-2), the total proportion thereof is generally 10 to 95% by mole, preferably 15 to 90% by mole, more preferably 20 to 85% by mole, with respect to the total structural units (100% by mole) of the resin (A).

Further, examples of the structural unit (a1) having a group (1) include a structural unit presented by formula (a1-3). The structural unit represented by formula (a1-3) is sometimes referred to as "structural unit (a1-3)". The monomer from which the structural unit (a1-3) is derived is sometimes referred to as "monomer (a1-3)".

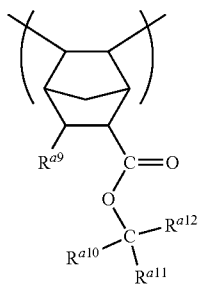
(a1-3)

In the formula, $R^{a9}$ represents a carboxy group, a cyano group, a —COOR$^{a13}$, a hydrogen atom or a $C_1$ to $C_3$ aliphatic hydrocarbon group that may have a hydroxy group, $R^{a13}$ represents a $C_1$ to $C_8$ aliphatic hydrocarbon group, a $C_3$ to $C_{20}$ alicyclic hydrocarbon group or a group formed by combining thereof, a hydrogen atom contained in the aliphatic hydrocarbon group and the alicyclic hydrocarbon group may be replaced by a hydroxy group, a methylene group contained in the aliphatic hydrocarbon group and the alicyclic hydrocarbon group may be replaced by an oxygen atom or a carbonyl group, and $R^{a10}$, $R^{a11}$ and $R^{a12}$ independently represent a $C_1$ to $C_8$ alkyl hydrocarbon group, a $C_3$ to $C_{20}$ alicyclic hydrocarbon group or a group formed by combining them, or $R^{a10}$ and $R^{a11}$ may be bonded together with a carbon atom bonded thereto to form a $C_1$ to $C_{20}$ divalent alicyclic hydrocarbon group.

Examples of the aliphatic hydrocarbon group that may have a hydroxy group for $R^{a9}$ include methyl, ethyl, propyl, hydroxymethy and 2-hydroxyethyl groups.

Examples of —COOR$^{a13}$ group include a group in which a carbonyl group is bonds to the alkoxy group, such as methoxycarbonyl and ethoxycarbonyl groups.

Examples of the $C_1$ to $C_8$ aliphatic hydrocarbon group for $R^{a13}$ include methyl, ethyl, propyl, isopropyl, n-butyl, sec-butyl, tert-butyl, n-pentyl, n-hexyl, n-heptyl, 2-ethylhexyl and n-octyl groups.

Examples of the $C_3$ to $C_{20}$ alicyclic hydrocarbon group for $R^{a13}$ include cyclopentyl, cyclopropyl, adamantyl, adamantylmetyl, 1-(adamantyl-1-yl)-methylethyl, 2-oxo-oxolane-3-yl, 2-oxo, oxolane-4-yl groups.

Examples of the alkyl group for $R^{a10}$ to $R^{a12}$ include methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group for $R^{a10}$ and $R^{a12}$ include monocyclic hydrocarbon groups such as a cycloalkyl group, i.e., cyclopropyl, cyclobutyl, cyclopentyl, cyclohexyl, methylcyclohexyl, dimethylcyclohexyl, cycloheptyl, cyclooctyl, cycloheptyl and cyclodecyl groups; and polycyclic hydrocarbon groups such as decahydronaphtyl, adamantyl, 2-alkyl-2-adamantyl, 1-(adamantane-1-yl) alkane-1-yl, norbornyl, methyl norbornyl and isobornyl groups.

When $R^{a10}$ and $R^{a11}$ is bonded together with a carbon atom bonded thereto to form a divalent alicyclic hydrocarbon group, examples of the group represented by —C($R^{a10}$)($R^{a11}$)($R^{a12}$) include groups below.

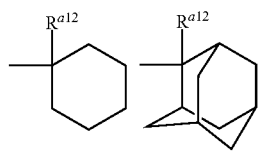

Examples of the monomer (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methy-2-adamantane-2-yl 5-norbornene-2-carboxylate, 2-ethyl-2-adamantane-2-yl 5-norbornene-2-carboxylate, 1-(4-methycyclohexyl)-1-methylethyl 5-norbornene-2-carboxylate, 1-(4-hydroxycyclohexyl)-1-methylethyl 5-norbornene-2-carboxylate, 1-methyl-(4-oxo-cyclohexyl)-1-ethyl 5-norbornene-2-carboxylate, and 1-(1-adamantane-1-yl)-1-methylethyl 5-norbornene-2-carboxylate.

The resin (A) having a structural unit (a1-3) can improve the resolution of the obtained resist composition because it has a bulky structure, and also can improve a dry-etching tolerance of the obtained resist composition because of a rigid norbornene ring having been incorporated into a main chain of the resin (A).

When the resin (A) contains the structural unit (a1-3), the proportion thereof is generally 10% by mole to 95% by mole, preferably 15% by mole to 90% by mole, and more preferably 20% by mole to 85% by mole, with respect to the total structural units constituting the resin (A) (100% by mole).

Examples of a structural unit (a1) having a group (2) include a structural unit represented by formula (a1-4). The structural unit is sometimes referred to as "structural unit (a1-4)".

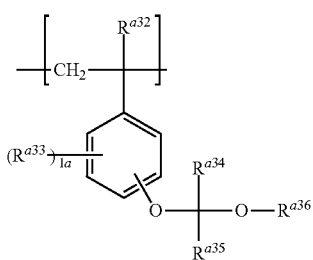

In the formula, $R^{a32}$ represents a hydrogen atom, a halogen atom or a $C_1$ to $C_6$ alkyl group that may have a halogen atom, $R^{a33}$ in each occurrence independently represent a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyloxy group or methacryloyloxy group, la represents an integer 0 to 4, $R^{a34}$ and $R^{a35}$ independently represent a hydrogen atom or a $C_1$ to $C_{12}$ hydrocarbon group; and $R^{a36}$ represents a $C_1$ to $C_{20}$ hydrocarbon group, or $R^{a35}$ and $R^{a36}$ may be bonded together with a C—O bonded thereto to form a $C_3$ to $C_{20}$ divalent heterocyclic group, and a methylene group contained in the hydrocarbon group or the divalent heterocyclic group may be replaced by an oxygen atom or sulfur atom.

Examples of the alkyl group for $R^{a32}$ and $R^{a33}$ include methyl, ethyl, propyl, isopropyl, butyl, pentyl and hexyl groups. The alkyl group is preferably a $C_1$ to $C_4$ alkyl group, and more preferably a methyl group or an ethyl group, and still more preferably a methyl group.

Examples of the halogen atom for $R^{a32}$ and $R^{a33}$ include fluorine, chlorine, bromine and iodine atoms.

Examples of the alkyl group that may have a halogen atom include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

Examples of an alkoxy group include methoxy, ethoxy, propoxy, butoxy, pentyloxy, and hexyloxy groups. The alkoxy group is preferably a $C_1$ to $C_4$ alkoxy group, more preferably a methoxy group or an ethoxy group, and still more preferably a methoxy group.

Examples of the acyl group include acetyl, propanonyl and butylyl groups.

Examples of the acyloxy group include acetyloxy, propanonyloxy and butylyloxy groups.

Examples of the hydrocarbon group for $R^{a34}$ and $R^{a35}$ are the same examples as described in $R^{a1'}$ to $R^{a2'}$ in formula (2).

Examples of hydrocarbon group for $R^{a36}$ include a $C_1$ to $C_{18}$ alkyl group, a $C_3$ to $C_{18}$ alicyclic hydrocarbon group, a $C_6$ to $C_{18}$ aromatic hydrocarbon group and a combination thereof.

In formula (a1-4), $R^{a32}$ is preferably a hydrogen atom.

$R^{a33}$ is preferably a $C_1$ to $C_4$ alkoxy group, more preferably a methoxy group or an ethoxy group, and still more preferably a methoxy group.

la is preferably 0 or 1, and more preferably 0.

$R^{a33}$ is preferably a hydrogen atom.

$R^{a35}$ is preferably a $C_1$ to $C_{12}$ hydrocarbon group, and more preferably a methyl group or an ethyl group.

The hydrocarbon group for $R^{a36}$ is preferably a $C_1$ to $C_{18}$ alkyl group, a $C_3$ to $C_{18}$ alicyclic hydrocarbon group, a $C_6$ to $C_{18}$ aromatic hydrocarbon group and a combination thereof, and more preferably a $C_1$ to $C_{18}$ alkyl group, a $C_3$ to $C_{18}$ alicyclic hydrocarbon group or a $C_7$ to $C_{10}$ aralkyl group. The alkyl group and the alicyclic hydrocarbon group for $R^{a36}$ is preferably not substituted. When the aromatic hydrocarbon group of $R^{a36}$ has a substituent, the substituent is preferably a $C_6$ to $C_{10}$ aryloxy group.

Examples of the monomer from which a structural unit (a1-4) is derived include monomers described in JP 2010-204646A. Among them, the monomers are preferably monomers represented by formula (a1-4-1) to formula (a1-4-7), and more preferably monomers represented by formula (a1-4-1) to formula (a1-4-5) below.

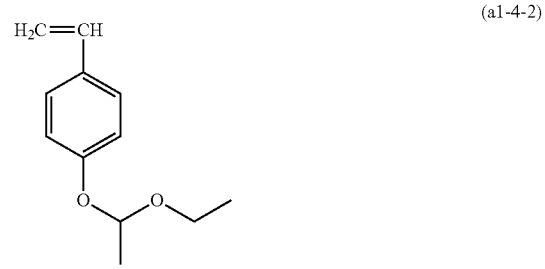

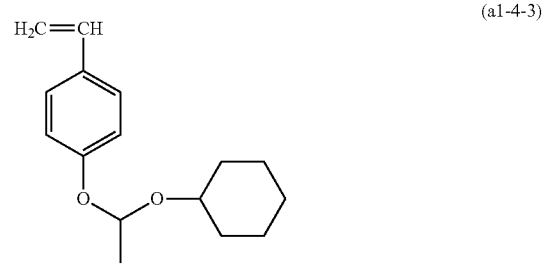

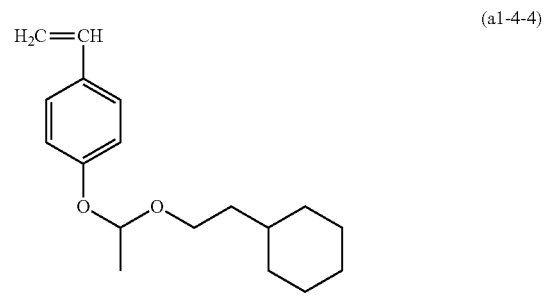

(a1-4-5)
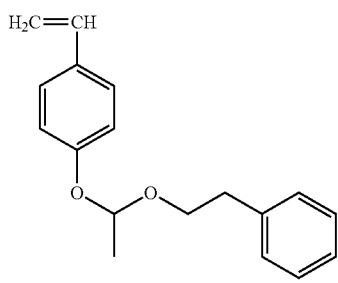

(a1-4-6)
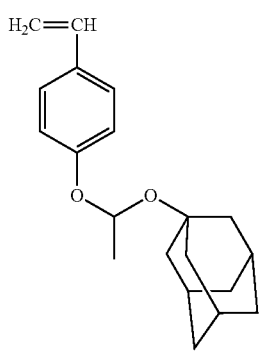

(a1-4-7)
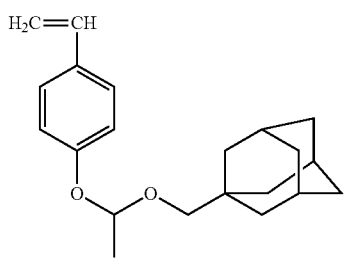

(a1-4-8)
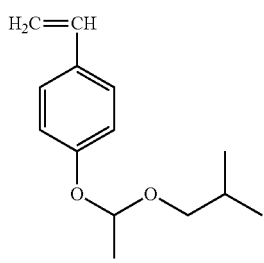

When the resin (A) contains the structural unit (a1-4), the proportion thereof is generally 10% by mole to 95% by mole, preferably 15% by mole to 90% by mole, more preferably 20% by mole to 85% by mole, with respect to the total structural units constituting the resin (A) (100% by mole).

Examples of a structural unit having an acid-labile group, which is derived from a (meth)acrylic, monomer include a structural unit represented by formula (a1-5). Such structural unit is sometimes referred to as "structural unit (a1-5)".

(a1-5)
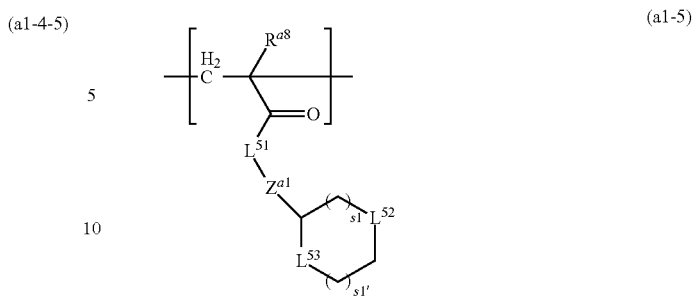

In the formula, $R^{a8}$ represents a hydrogen atom, a halogen atom or a $C_1$ to $C_6$ alkyl group that may have a halogen atom, $Z^{a1}$ represents a single bond or *—$(CH_2)_{h3}$—CO-$L^{54}$-, h3 represents an integer of 1 to 4,

* represents a binding position to $L^{51}$, $L^{51}$, $L^{52}$ and $L^{53}$ independently represent —O— or —S—, s1 represents an integer of 1 to 3, and s1' represents an integer of 0 to 3.

Examples of the halogen atom include fluorine, chlorine, bromine and iodine atoms, and preferably a fluorine atom.

Examples of the alkyl group that may have a halogen atom include methyl, ethyl, propyl, butyl, pentyl, hexyl, heptyl, octyl, fluoromethyl and trifluoromethyl groups.

In formula (a1-5), $R^{a8}$ is preferably a hydrogen atom, a methyl group or trifluoromethyl group, $L^{55}$ is preferably —O—, $L^{52}$ and $L^{53}$ are independently preferably —O— or —S—, and more preferably one is —O— and another is —S—, s1 is preferably 1, s1' is preferably an integer of 0 to 2, and $Z^{a1}$ is preferably a single bond or *—$CH_2$—CO—O—.

Examples of a monomer from which a structural unit (a1-5) is derived include a monomer described in JP 2010-61117A. Among them, the monomers are preferably monomers represented by formula (a1-5-1) to formula (a1-5-4), and more preferably monomers represented by formula (a1-5-1) to formula (a1-5-2) below.

(a1-5-1)
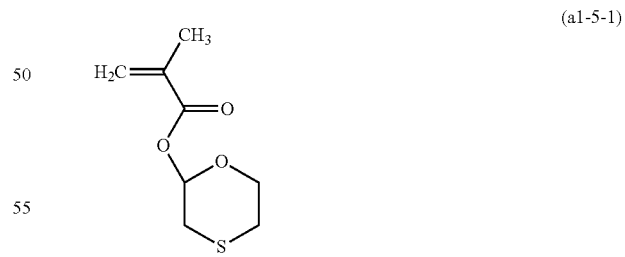

(a1-5-2)
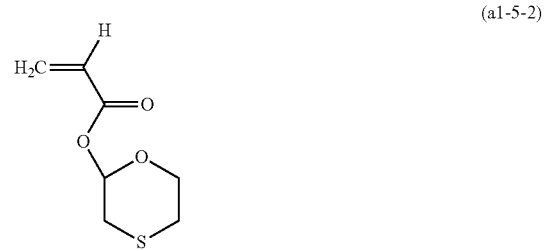

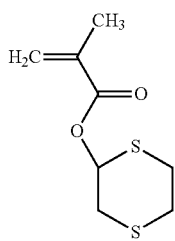

(a1-5-3)

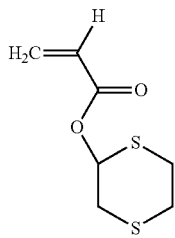

(a1-5-4)

When the resin (A) contains the structural unit (a1-5), the proportion thereof is generally 1% by mole to 50% by mole, preferably 3% by mole to 45% by mole, and more preferably 5% by mole to 40% by mole, with respect to the total structural units (100% by mole) constituting the resin (A).

Examples of a structural unit (a1) in a resin (A) is preferably at least one, more preferably two or more of the structural units selected from the structural unit (a1-0), the structural unit (a1-1), the structural unit (a1-2) and the structural unit (a1-5), still more preferably a combination of the structural unit (a1-1) and the structural unit (a1-2), a combination of the structural unit (a1-1) and the structural unit (a1-5), a combination of the structural unit (a1-1) and the structural unit (a1-0), a combination of the structural unit (a1-2) and the structural unit (a1-0), a combination of the structural unit (a1-5) and the structural unit (a1-0), a combination of the structural unit (a1-0), the structural unit (a1-1) and the structural unit (a1-2), a combination of the structural unit (a1-0), the structural unit (a1-1) and the structural unit (a1-5), in particular preferably a combination of the structural unit (a1-1) and the structural unit (a1-2), and a combination of the structural unit (a1-1) and the structural unit (a1-5).

<Structural Unit (s)>

The structural unit (s) is derived from a monomer having no acid-labile group which monomer is sometimes referred to as "monomer (s)".

For the monomer (s) from which a structural unit (s) is derived, a known monomer having no acid-labile group can be used.

As the structural unit (s), preferred is a structural unit having a hydroxy group or a lactone ring but having no acid-labile group. When the resist composition contains a resin which has a structural unit (s) having a hydroxy group (such structural unit is sometimes referred to as "structural unit (a2)") and/or a structural unit (s) having a lactone ring (such structural unit is sometimes referred to as "structural unit (a3)"), the adhesiveness of resist obtained therefrom to a substrate and resolution of resist pattern tend to be improved.

<Structural Unit (a2)>

A hydroxy group which the structural unit (a2) has may be an alcoholic hydroxy group or a phenolic hydroxy group.

When KrF excimer laser lithography (248 nm), or high-energy irradiation such as electron beam or EUV (extreme ultraviolet) is used for the resist composition, the structural unit having a phenolic hydroxy group is preferably used as structural unit (a2).

When ArF excimer laser lithography (193 nm) is used, the structural unit having an alcoholic hydroxy group is preferably used as structural unit (a2), and the structural represented by formula (a2-1) is more preferred.

The structural unit (a2) may be used as one kind of the structural unit or as a combination of two or more kinds of the structural units.

Examples of the structural unit (a2) having a phenolic hydroxy group include the structural unit represented by formula (a2-0) (which structural unit is sometimes referred to as "structural unit (a2-0)").

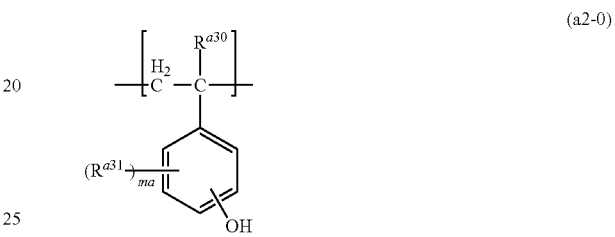

(a2-0)

In the formula, $R^{a30}$ represents a hydrogen atom, a halogen atom or a $C_1$ to $C_6$ alkyl group that may have a halogen atom, $R^{a31}$ in each occurrence independently represents a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyl group or methacryloyl group, and ma represents an integer 0 to 4.

Examples of the halogen atom include a chlorine atom, a fluorine atom and bromine atom.

Examples of the alkyl group include methyl, ethyl, propyl, isopropyl, butyl, n-pentyl and n-hexyl groups.

Examples of a $C_1$ to $C_6$ alkyl group that may have a halogen atom for $R^{a30}$ include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups. $R^{a30}$ is preferably a hydrogen atom or a $C_1$ to $C_4$ alkyl group, and more preferably a hydrogen atom, a methyl group or an ethyl group, and still more preferably a hydrogen atom or a methyl group.

Examples of a $C_1$ to $C_6$ alkoxy group for $R^{a31}$ include methoxy, ethoxy, propoxy, t-butoxy, pentyloxy and hexyloxy groups. $R^{a31}$ is preferably a $C_1$ to $C_4$ alkoxy group, more preferably a methoxy group and an ethoxy group, and still more preferably a methoxy group.

Examples of the acyl group for $R^{a31}$ include acetyl, propanonyl and butylyl groups.

Examples of the acyloxy group for $R^{a31}$ include acetyloxy, propanonyloxy and butylyloxy groups.

ma is preferably 0, 1 or 2, more preferably 0 or 1, still more preferably 0.

Examples of a monomer from which the structural unit (a2-0) is derived include monomers described in JP2010-204634A.

The structural unit (a2-0) is preferably a structural unit represented below. Among them, structural units represented by formula (a2-0-1), formula (a2-0-2), formula (a2-0-3) and formula (a2-0-4) are preferred, and structural units represented by formula (a2-0-1) and formula (a2-0-2) are more preferred.

(a2-0-1)
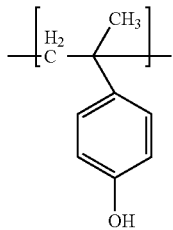

(a2-0-2)
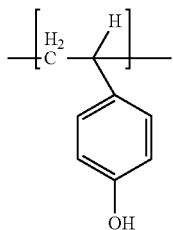

(a2-0-3)
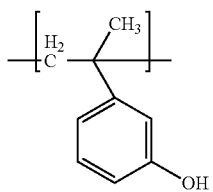

(a2-0-4)
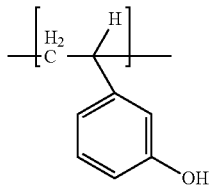

The resin (A) which contains the structural unit (a2-0) can be produced, for example, by polymerizing a monomer where its phenolic hydroxy group has been protected with a suitable protecting group, followed by deprotection. The deprotection is carried in such a manner that an acid-labile group in the structural unit (a1) is significantly impaired. Examples of the protecting group for a phenolic hydroxy group include an acetyl group.

When the resin (A) contains the structural unit (a2-0) having the phenolic hydroxy group, the proportion thereof is generally 5% by mole to 95% by mole, preferably 10% by mole to 80% by mole, more preferably 15% by mole to 80% by mole, with respect to the total structural units (100% by mole) constituting the resin (A).

Examples of the structural unit (a2) having alcoholic hydroxy group include the structural unit represented by formula (a2-1) (which is sometimes referred to as "structural unit (a2-1)").

(a2-1)
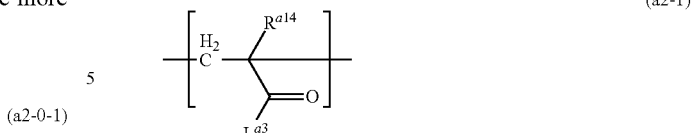

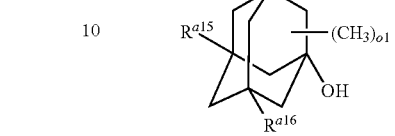

In the formula, $L^{a3}$ represents —O— or *—O—$(CH_2)_{k2}$—CO—O—, k2 represents an integer of 1 to 7,

* represents a binding position to —CO—, $R^{a14}$ represents a hydrogen atom or a methyl group, $R^{a15}$ and $R^{a16}$ each independently represent a hydrogen atom, a methyl group or a hydroxy group, and o1 represents an integer of 0 to 10.

In formula (a2-1), $L^{a3}$ is preferably —O—, —O—$(CH_2)_{f1}$—CO—O—, here f1 represents an integer of 1 to 4, and more preferably —O—.

$R^{a14}$ is preferably a methyl group.

$R^{a15}$ is preferably a hydrogen atom.

$R^{a16}$ is preferably a hydrogen atom or a hydroxy group.

o1 is preferably an integer of 0 to 3, and more preferably an integer of 0 or 1.

Examples of the monomer from which the structural unit (a2-1) is derived include monomers described in JP 2010-204646A. Among them, the monomers are preferably monomers represented by formula (a2-1-1) to formula (a2-1-6), more preferably structural units represented by formula (a2-1-1) to formula (a2-1-4), and still more preferably structural units represented by formula (a2-1-1) and formula (a2-1-3) below.

(a2-1-1)
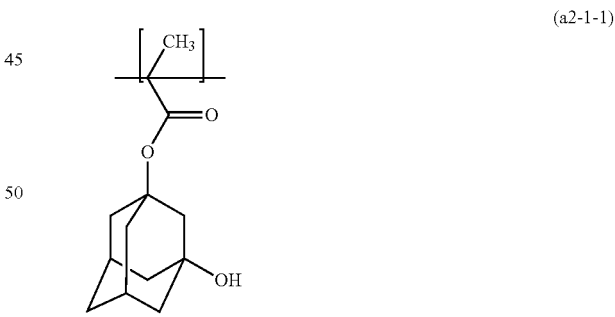

(a2-1-2)
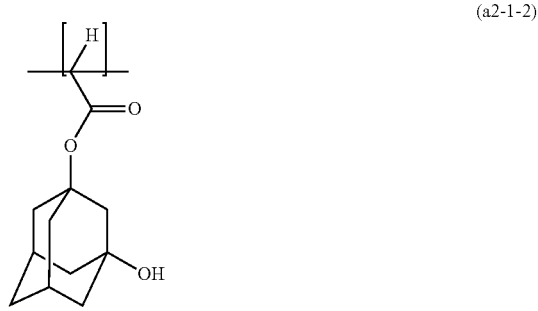

-continued (a2-1-3)
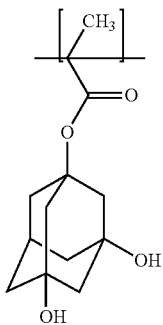

(a2-1-4)
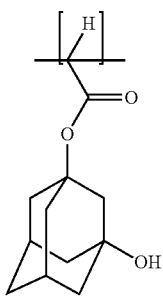

(a2-1-5)
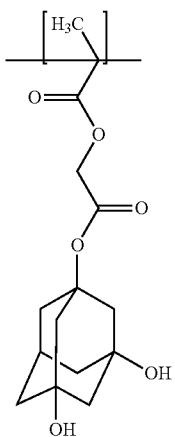

(a2-1-6)
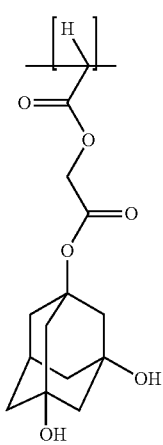

When the resin (A) contains the structural unit (a2-1), the proportion thereof is generally 1% by mole to 45% by mole, preferably 1% by mole to 40% by mole, more preferably 1% by mole to 35% by mole, and still more preferably 2% by mole to 20% by mole, with respect to the total structural units (100% by mole) constituting the resin (A).

<Structural Unit (a3)>

The lactone ring included in the structural unit (a3) may be a monocyclic compound such as β-propiolactone, γ-butyrolactone, δ-valerolactone, or a condensed ring of monocyclic lactone ring with another ring. Examples of the lactone ring preferably include γ-butyrolactone, amadantane lactone, or bridged ring with γ-butyrolactone.

Examples of the structural unit (a3) include structural units represented by any of formula (a3-1), formula (a3-2), formula (a3-3) and formula (a3-4). These structural units may be used as one kind of the structural unit or as a combination of two or more kind of the structural units.

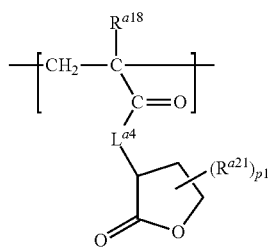
(a3-1)

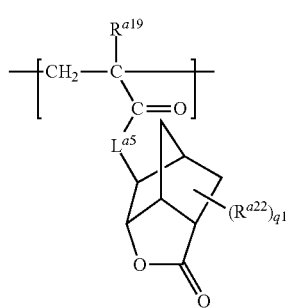
(a3-2)

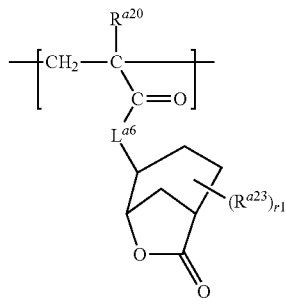
(a3-3)

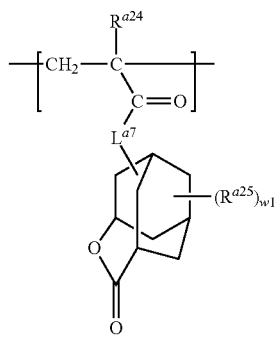
(a3-4)

In the formula, $L^{a4}$ represents *—O— or *—O—$(CH_2)_{k3}$—CO—O—, k3 represents an integer of 1 to 7, * represents a binding position to a carbonyl group, $R^{a18}$ represents a hydrogen atom or a methyl group, $R^{a21}$ in each occurrence represents a $C_1$ to $C_4$ aliphatic hydrocarbon group, and p1 represents an integer of 0 to 5, $L^{a5}$ represents *—O— or *—O—$(CH_2)_{k3}$—CO—O—, k3 represents an integer of 1 to 7, * represents a binding position to a carbonyl group, $R^{a19}$ represents a hydrogen atom or a methyl group, $R^{a22}$ in each occurrence represents a carboxy group, a cyano group or a $C_1$ to $C_4$ aliphatic hydrocarbon group, q1 represents an integer of 0 to 3, $L^{a6}$ represents *—O— or *—O—$(CH_2)_{k3}$—CO—O—, k3 represents an integer of 1 to 7, * represents a binding position to a carbonyl group, $R^{a20}$ represents a hydrogen atom or a methyl group, $R^{23}$ in each occurrence represents a carboxy group, a cyano group or a $C_1$ to $C_4$ aliphatic hydrocarbon group, and r1 represents an integer of 0 to 3, $R^{a24}$ represents a hydrogen atom, a halogen atom or a $C_1$ to $C_6$ alkyl group that may have a halogen atom, $R^{a25}$ in each occurrence represents a carboxy group, a cyano group or a $C_1$ to $C_4$ aliphatic hydrocarbon group, $L^{a7}$ represents a single bond, *-$L^{a8}$-O—, *-$L^{a8}$-CO—O—, *-$L^{a8}$-CO—O-$L^{a9}$-CO—O—, or *-$L^{a8}$-O—CO—$L^{a9}$-O—; * represents a binding position to a carbonyl group, $L^{a8}$ and $L^{a9}$ independently represents a $C_1$ to $C_6$ alkanediyl group, and w1 represents an integer of 0 to 8.

Examples of the aliphatic hydrocarbon group for $R^{a21}$, $R^{a2}$, $R^{a23}$ and $R^{a25}$ include an alkyl group such as methyl, ethyl, n-propyl, isopropyl, n-butyl, sec-butyl, tert-butyl, n-pentyl and n-hexyl groups.

Examples of the halogen atom for $R^{a24}$ include fluorine, chlorine, bromine or iodine atom.

Examples of the alkyl group of $R^{a24}$ include methyl, ethyl, n-propyl, isopropyl, n-butyl, sec-butyl, tert-butyl, n-pentyl and n-hexyl groups, preferably a $C_1$ to $C_4$ alkyl group, more preferably a methyl group or an ethyl group.

Examples of the alkyl group having a halogen atom for $R^{a24}$ include trifluoromethyl, perfluoroethyl, perfluoropropyl, perfluoro-isopropyl, perfluorobutyl, perfluoro-sec-butyl, perfluoro-tert-butyl, perfluoropentyl, perfluorohexyl, tricloromethyl, tribromomethyl and triiodomethyl groups.

Examples of the alkanediyl group for $L^{a8}$ and $L^{a9}$ include methylene, ethylene, propane-1,3-diyl, propane-1,2-diyl, butane-1,4-diyl, pentane-1,5-diyl, hexane-1,6-diyl, butane-1,3-diyl, 2-methylpropane-1,3-diyl, 2-methylpropane-1,2-diyl, pentane-1,4-diyl and 2-methylbutane-1,4-diyl groups.

In formulae (a3-1) to (a3-3), $L^{a4}$ to $L^{a6}$ is independently preferably —O—, *—O—$(CH_2)_{k3'}$—CO—O—, here k3' represents an integer of 1 to 4, more preferably —O— or *—O—$CH_2$—CO—O—, and still more preferably —O—.

$R^{a18}$ to $R^{a21}$ are preferably a methyl group.

$R^{a22}$ and $R^{a23}$ are independently preferably a carboxy group, a cyano group or a methyl group.

p1, q1 and r1 are independently preferably an integer of 0 to 2, and more preferably 0 or 1.

In formula (a3-4), $R^{a24}$ is preferably a hydrogen atom or a $C_1$ to $C_4$ alkyl group, more preferably a hydrogen atom, a methyl group or an ethyl group, and still more preferably a hydrogen atom or a methyl group.

$R^{a25}$ is preferably a carboxy group, a cyano group or a methyl group.

$L^{a7}$ is preferably a single bond or *-$L^{a8}$-CO—O—, and more preferably a single bond, —$CH_2$—CO—O— or —$C_2H_4$—CO—O—.

w1 is preferably an integer of 0 to 2, and more preferably 0 or 1.

In particular, the structural unit represented by formula (a3-4) is preferably a structural unit represented by formula (a3-4') below.

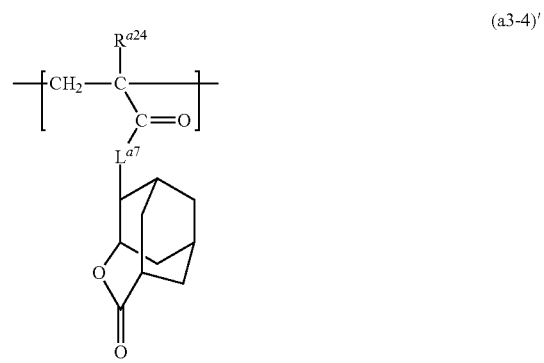

(a3-4)'

In the formula, all symbols are as defined above.

Examples of the monomer from which the structural unit (a3) is derived include monomers described in JP 2010-204646A, monomers described in JP2000-122294A and monomers described in JP2012-41274A. The structural units are preferably structural units represented by formula (a3-1-1) to formula (a3-1-4), formula (a3-2-1) to formula (a3-2-4), formula (a3-3-1) to formula (a3-3-4), formula (a3-4-1) to formula (a3-4-12), more preferably structural units represented by formula (a3-1-1) to formula (a3-1-2), formula (a3-2-3), formula (a3-2-4), formula (a3-4-1) and formula (a3-4-6), and still more preferably structural units represented by formula (a3-1-1), formula (a3-2-3) or formula (a3-4-2) below.

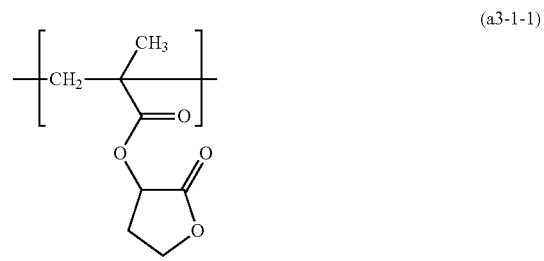

(a3-1-1)

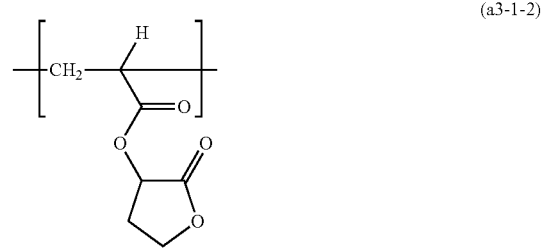

(a3-1-2)

(a3-1-3)
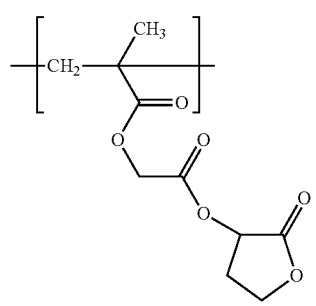
(a3-1-4)
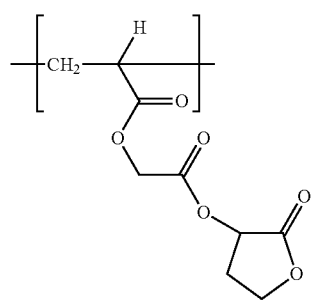
(a3-2-1)
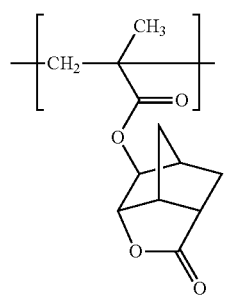
(a3-2-2)
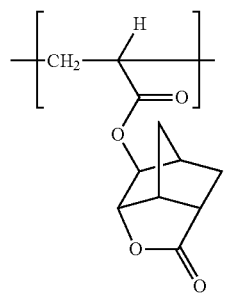
(a3-2-3)
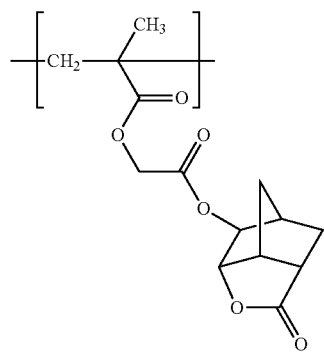
(a3-2-4)
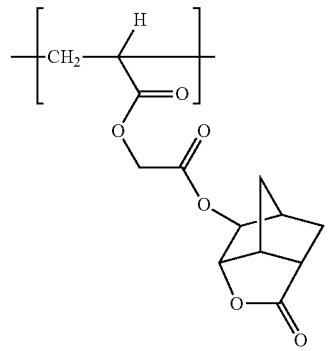
(a3-3-1)
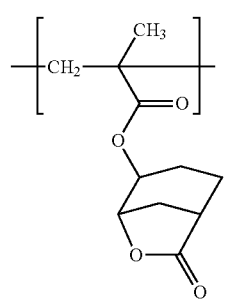
(a3-3-2)
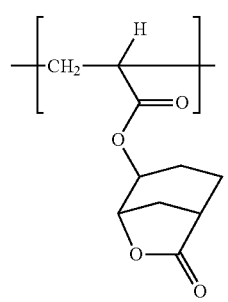
(a3-3-3)
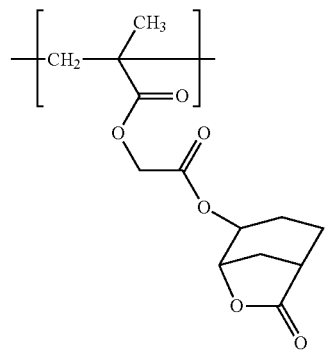
(a3-3-4)
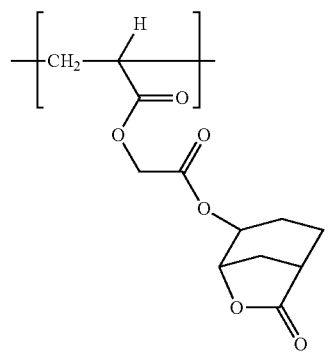

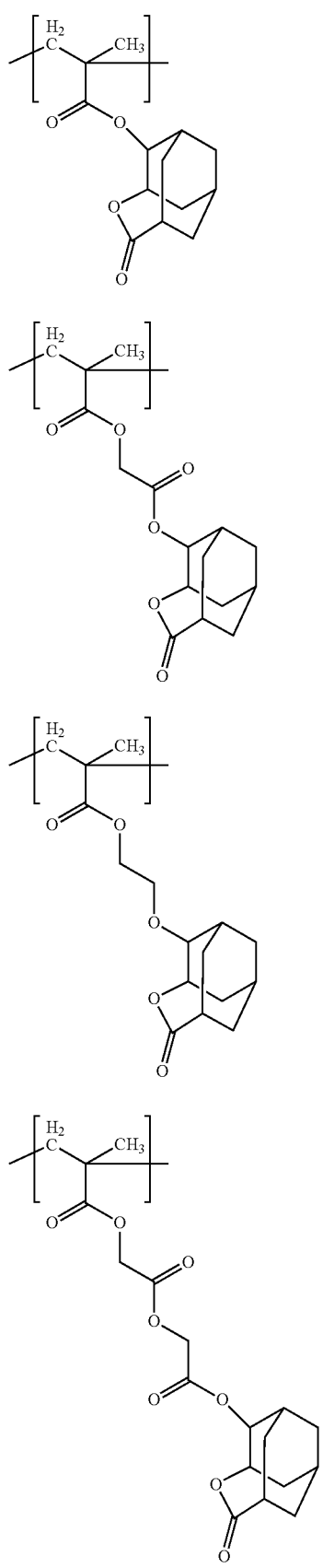
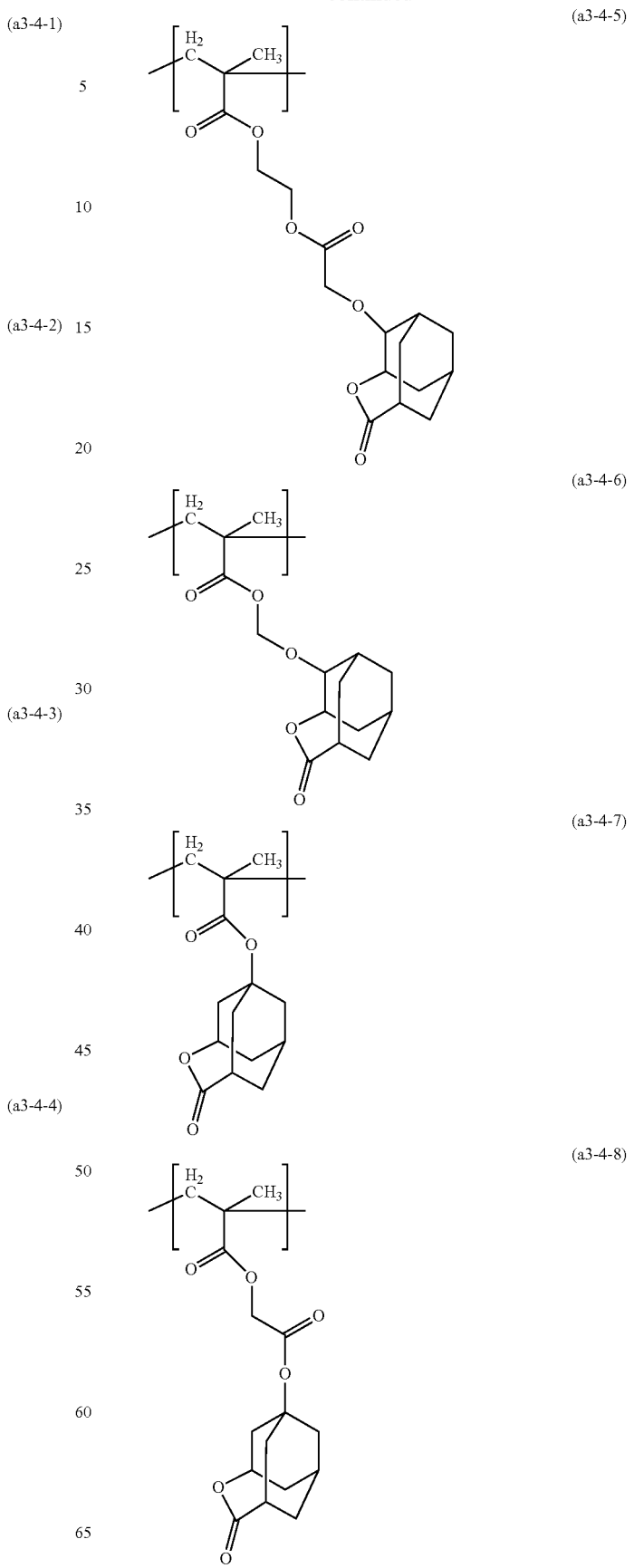

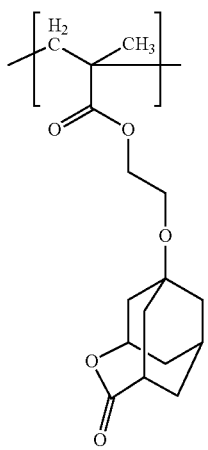
(a3-4-9)

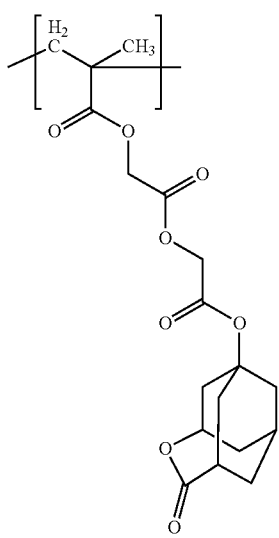
(a3-4-10)

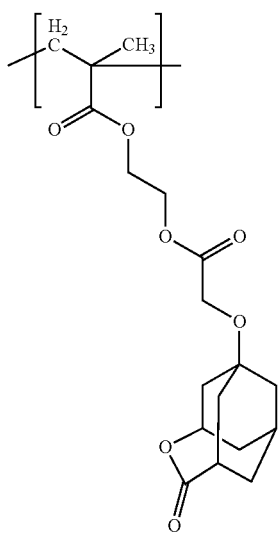
(a3-4-11)

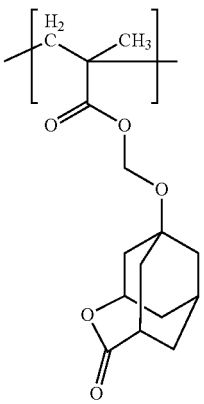
(a3-4-12)

Examples of the structural units (a3) include the structural units represented by the formula (a3-4-1) to formula (a3-4-12) in which a methyl group corresponding to $R^{24}$ has been replaced by a hydrogen atom.

When the resin (A) contains the structural unit (a3), the total proportion thereof is preferably 5% by mole to 70% by mole, more preferably 10% by mole to 65% by mole, still more preferably 10% by mole to 60% by mole, with respect to the total structural units (100% by mole) constituting the resin (A).

The proportion of each structural unit represented by formula (a3-1), formula (a3-2), formula (a3-3) and formula (a3-4) is preferably 5% by mole to 60% by mole, more preferably 5% by mole to 50% by mole, still more preferably 10% by mole to 50% by mole, with respect to the total structural units (100% by mole) constituting the resin (A).

<Other Structural Unit (t)>

The resin (A) may further contain structural unit (s) other than the structural units (a2) and (a3). The structural unit (s) other than the structural units (a2) and (a3) is sometimes referred to as "structural unit (t)". Examples of the structural unit (t) include a structural unit which may have a halogen atom (which is sometimes referred to as "structural unit (a4)") other than the structural unit (a2) and the structural unit (a3), and a structural unit having a non-leaving hydrocarbon group (which is sometimes referred to as "structural unit (a5)"). The structural unit having a halogen atom preferably has a fluorine atom.

<Structural Unit (a4)>

Examples of the structural unit (a4) include the structural units represented by formula (a4-0).

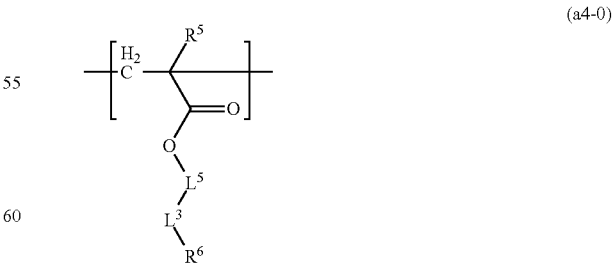
(a4-0)

In the formula, $R^5$ represents a hydrogen atom or a methyl group, $L^5$ represent a single bond or a $C_1$ to $C_4$ saturated aliphatic hydrocarbon group, $L^3$ represents a $C_1$ to $C_8$ perfluoroalkanediyl group or a $C_3$ to $C_{12}$ perfluorocycloalkanediyl group, and $R^6$ represents a hydrogen atom or a fluorine atom.

Examples of the saturated aliphatic hydrocarbon group for $L^5$ include a liner alkanediyl group such as methylene, ethylene, propane-1,3-diyl, butane-1,4-diyl, and a branched alkanediyl group such as ethane-1,1-diyl, propane-1,2-diyl, butane-1,3-diyl, 2-methylpropane-1,3-diyl and 2-methylpropane-1,2-diyl groups.

Examples of the perfluoroalkanediyl group for $L^3$ include difluoromethylene, perfluoroethylene, perfluoroethylmethylene, perfluoropropane-1,3-diyl, a perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluorocycloalkanediyl group for $L^3$ include perfluorocyclohexanediyl, perfluorocyclopentanediyl, perfluorocycloheptanediyl and perfluoroadamantanediyl groups.

$L^5$ is preferably a single bond, a methylene or an ethylene group, and more preferably a single bond or a methylene group.

$L^3$ is preferably a $C_1$ to $C_6$ perfluoroalkanediyl group, more preferably a $C_1$ to $C_3$ perfluoroalkanediyl group.

Examples of the structural unit (a4-0) include structural units represented by formula (a4-0-1) to formula (a4-0-32).

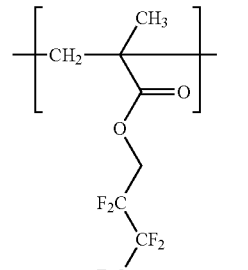

(a4-0-1)

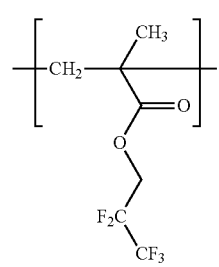

(a4-0-2)

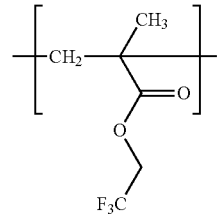

(a4-0-3)

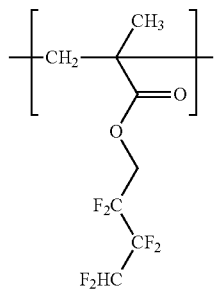

(a4-0-4)

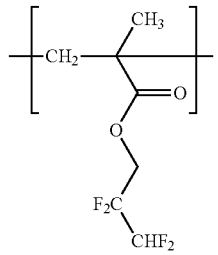

(a4-0-5)

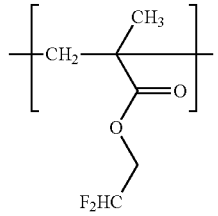

(a4-0-6)

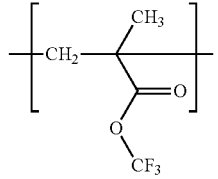

(a4-0-7)

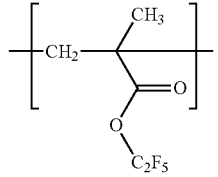

(a4-0-8)

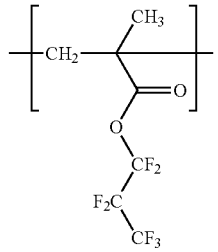

(a4-0-9)

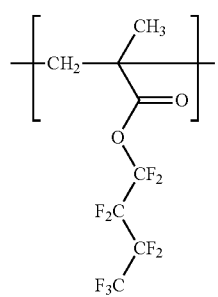 (a4-0-10)
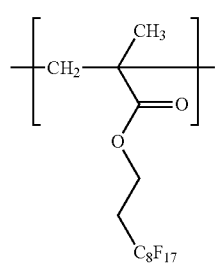 (a4-0-11)
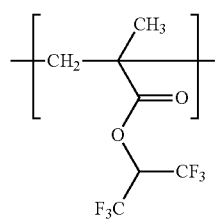 (a4-0-12)
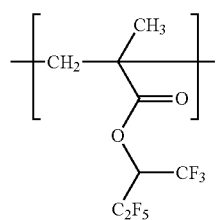 (a4-0-13)
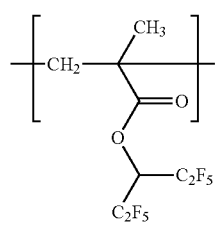 (a4-0-14)
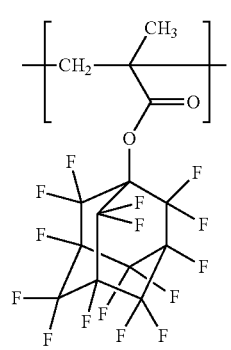 (a4-0-15)
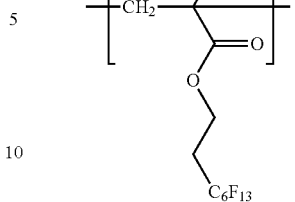 (a4-0-16)
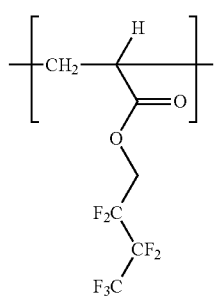 (a4-0-17)
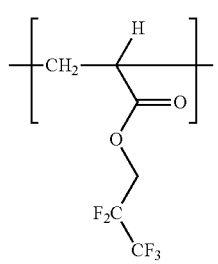 (a4-0-18)
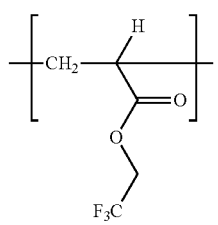 (a4-0-19)
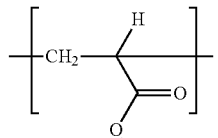 (a4-0-20)
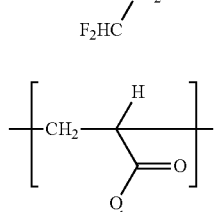 (a4-0-21)
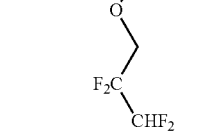

(a4-0-22)
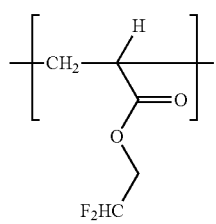
(a4-0-23)
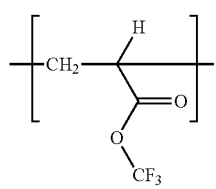
(a4-0-24)
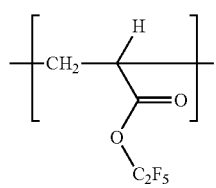
(a4-0-25)
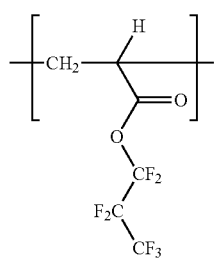
(a4-0-26)
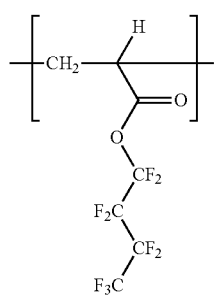
(a4-0-27)
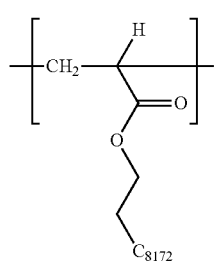
(a4-0-28)
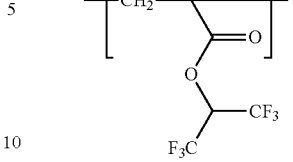
(a4-0-29)
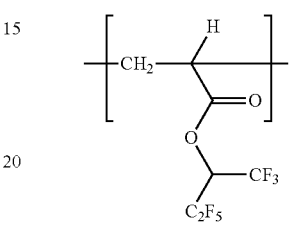
(a4-0-30)
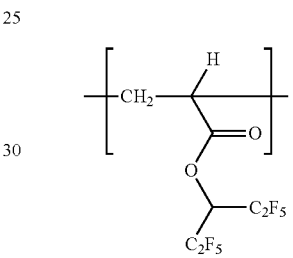
(a4-0-31)
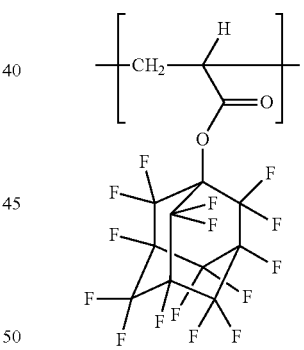
(a4-0-32)
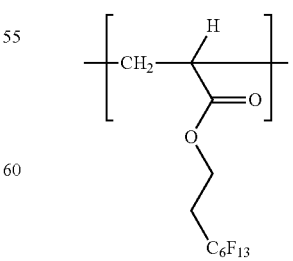
Examples of the structural unit (a4) include the structural units represented by formula (a4-1).

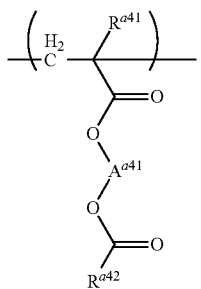

(a4-1)

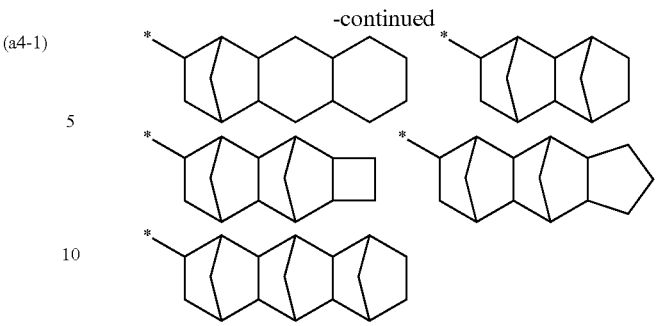

-continued

In the formula, $R^{a41}$ represents a hydrogen atom or a methyl group, $R^{a42}$ represents an optionally substituted $C_1$ to $C_{20}$ hydrocarbon group where a methylene group may be replaced by an oxygen atom or a carbonyl group, and $A^{a41}$ represents an optionally substituted $C_1$ to $C_6$ alkanediyl group or a group represented by formula (a-g1):

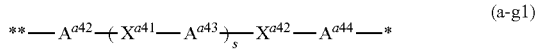

(a-g1)

wherein s represents 0 or 1, $A^{a42}$ and $A^{a44}$ independently represent an optionally substituted $C_1$ to $C_5$ aliphatic hydrocarbon group, $A^{a43}$ in occurrence represents a single bond or an optionally substituted $C_1$ to $C_5$ aliphatic hydrocarbon group, and $X^{a41}$ and $X^{a42}$ independently represent —O—, —CO—, —CO—O— or —O—CO—, provided that the total carbon number contained in the group of $A^{a42}$, $A^{a43}$, $A^{a44}$, $X^{a41}$ and $X^{a42}$ is 7 or less, and at least one of $A^{a41}$ and $R^{a42}$ has a halogen atom as a substituent, and

* and ** represent a binding position, and * represents a binding position to —O—CO— $R^{a42}$.

The hydrocarbon group for $R^{a42}$ includes a chain aliphatic hydrocarbon group, a cyclic aliphatic hydrocarbon group, an aromatic hydrocarbon group and a combination thereof.

The hydrocarbon group may have a carbon-carbon unsaturated bond, is preferably a chain aliphatic hydrocarbon group, a cyclic saturated aliphatic hydrocarbon group, and a combination thereof.

The saturated aliphatic hydrocarbon group is preferably a liner or a branched alkyl group, a monocyclic or a polycyclic alicyclic hydrocarbon group, and an aliphatic hydrocarbon group combining an alkyl group with an alicyclic hydrocarbon group.

Examples of the chain aliphatic hydrocarbon group include an alkyl group such as methyl, ethyl, n-propyl, n-butyl, n-pentyl, n-hexyl, n-heptyl, n-octyl, n-decyl, n-dodecyl, n-pentadecyl, n-hexadecyl, n-heptadecyl and n-octadecyl groups. Examples of the cyclic aliphatic hydrocarbon group include a monocyclic hydrocarbon group, i.e., cycloalkyl group such as cyclopentyl, cyclohexyl, cycloheptyl, cyclooctyl groups; and polycyclic hydrocarbon groups such as decahydronaphtyl, adamantyl and norbornyl groups as well as groups below. * represents a binding position.

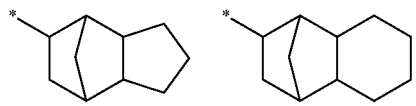

Examples of the aromatic hydrocarbon group include an aryl group such as phenyl, naphthyl, anthryl, biphenyl, phenanthryl and fluorenyl groups.

Examples of the substituent of $R^{a42}$ include a halogen atom or a group represented by formula (a-g3).

(a-g3)

In the formula, $X^{a43}$ represent an oxygen atom, a carbonyl group, a carbonyloxy group or an oxycarbonyl group, $A^{a45}$ represents a $C_1$ to $C_{17}$ aliphatic hydrocarbon group that has a halogen atom, and

* represents a binding position.

Examples of the halogen atom include fluorine, chlorine, bromine and iodine atom, and a fluorine atom is preferred.

Examples of the aliphatic hydrocarbon group for $A^{a45}$ are the same examples as the group of $R^{a42}$.

$R^{a42}$ is preferably an aliphatic hydrocarbon group that may have a halogen atom, and more preferably an alkyl group having a halogen atom and/or an aliphatic hydrocarbon group having the group represented by formula (a-g3).

When $R^{a42}$ is an aliphatic hydrocarbon group having a halogen atom, an aliphatic hydrocarbon group having a fluorine atom is preferred, a perfluoroalkyl group or a perfulorocycloalkyl group are more preferred, a $C_1$ to $C_6$ perfluoroalkyl group is still more preferred, a $C_1$ to $C_3$ perfluoroalkyl group is particularly preferred.

Examples of the perfluoroalkyl group include perfluoromethyl, perfluoroethyl, perfluoropropyl, perfluorobutyl, perfluoropentyl, perfluorohexyl, perfluoroheptyl and perfluorooctyl groups. Examples of the perfluorocycloalkyl group include perfluorocyclohexyl group.

When $R^{a42}$ is an aliphatic hydrocarbon group having the group represented by formula (a-g3), the total carbon number contained in the aliphatic hydrocarbon group including the group represented by formula (a-g3) is preferably 15 or less, more preferably 12 or less. The number of the group represented by formula (a-g3) is preferably one when the group represented by formula (a-g3) is the substituent.

The aliphatic hydrocarbon having the group represented by formula (a-g3) is more preferably a group represented by formula (a-g2):

(a-g2)

wherein $A^{a46}$ represents a $C_1$ to $C_{17}$ aliphatic hydrocarbon group that may have a halogen atom, $X^{a44}$ represent a carbonyloxy group or an oxycarbonyl group, $A^{a47}$ represents a $C_1$ to $C_{17}$ aliphatic hydrocarbon group that may have a halogen atom, provided that the total carbon number contained in the group of $A^{a46}$, $X^{a44}$ and $A^{a47}$ is 18 or less, at least one of $A^{a46}$ and $A^{a47}$ has a halogen atom, and

* represents a binding position to carbonyl group.

The carbon number of the aliphatic hydrocarbon group of $A^{a46}$ is preferably 1 to 6, and more preferably 1 to 3.

The carbon number of the aliphatic hydrocarbon group of $A^{a47}$ is preferably 4 to 15, and more preferably 5 to 12, and cyclohexyl and adamantyl groups are still more preferred as the aliphatic hydrocarbon group.

Preferred structure represented by formula (a-g2), *-$A^{a46}$-$X^{a44}$-$A^{a47}$, include the following ones.

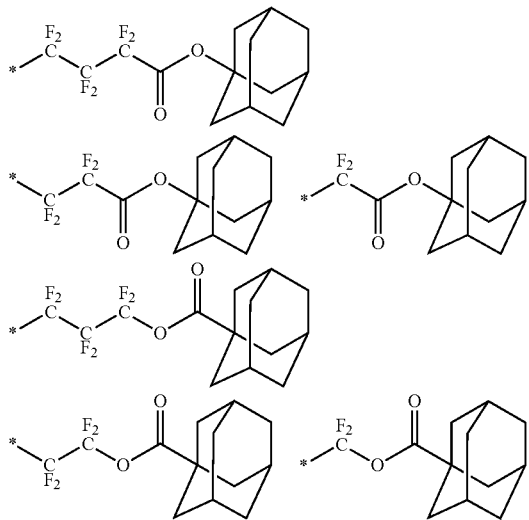

Examples of the alkanediyl group for $A^{a41}$ include a liner alkanediyl group such as methylene, ethylene, propane-1,3-diyl, butane-1,4-diyl, pentane-1,5-diyl and hexane-1,6-diyl groups;

a branched alkanediyl group such as propane-1,2-diyl, butan-1,3-diyl, 2-methylpropane-1,2-diyl, 1-methylpropane-1,4-diyl, 2-methylbutane-1,4-diyl groups.

Examples of the substituent of the alkanediyl group of $A^{a41}$ include a hydroxy group and a $C_1$ to $C_6$ alkoxy group.

Examples of the substituent of the alkanediyl of $A^{a41}$ include a hydroxy group and a $C_1$ to $C_6$ alkoxy group.

$A^{a41}$ is preferably a $C_1$ to $C_4$ alkanediyl group, more preferably a $C_2$ to $C_4$ alkanediyl group, and still more preferably an ethylene group.

In the group represented by formula (a-g1) (which is sometimes referred to as "group (a-g1)"), the aliphatic hydrocarbon group for $A^{a42}$, $A^{a43}$ and $A^{a44}$ may have a carbon-carbon unsaturated bond, is preferably a saturated aliphatic hydrocarbon group.

The saturated aliphatic hydrocarbon group is preferably a liner or a branched alkyl group, a monocyclic or a polycyclic alicyclic hydrocarbon group, and an aliphatic hydrocarbon group combining an alkyl group with an alicyclic hydrocarbon group.

Examples of the aliphatic hydrocarbon group for $A^{a42}$, $A^{a43}$ and $A^{a44}$ include methylene, ethylene, propane-1,3-diyl, propane-1,2-diyl, butane-1,4-diyl, 1-methylpropane-1,3-diyl, 2-methylpropane-1,3-diyl and 2-methylpropane-1,2-diyl groups.

Examples of the substituent of the aliphatic hydrocarbon group of $A^{a42}$, $A^{a43}$ and $A^{a44}$ include a hydroxy group and a $C_1$ to $C_6$ alkoxy group.

s is preferably 0.

Examples of the group (a-g1) in which $X^{a42}$ represents an oxygen atom, a carbonyl group, a carbonyloxy group or an oxycarbonyl group include the following ones. In the formula, * and  each represent a binding position, and  represents a binding position to —O—CO—$R^{a42}$.

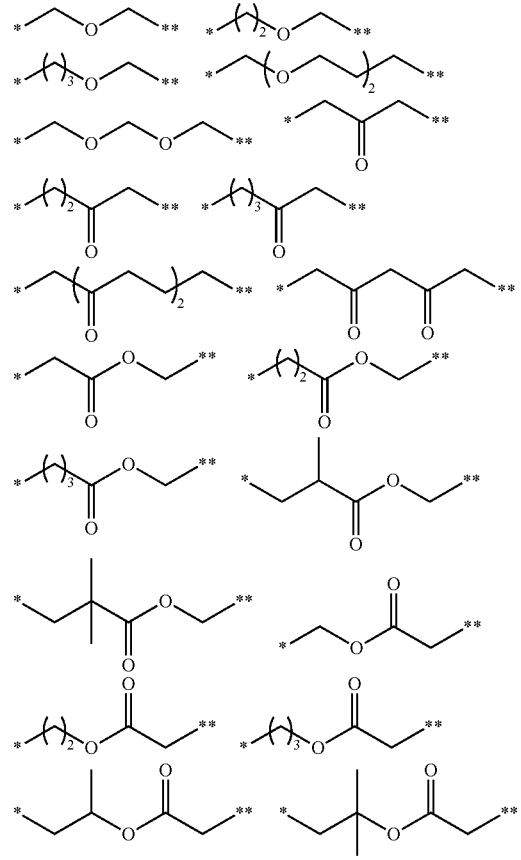

The structural unit represented by formula (a4-1) is preferably structural units represented by formula (a4-2) and formula (a4-3):

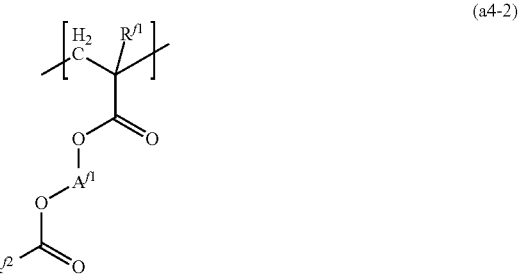

(a4-2)

wherein $R^{f1}$ represents a hydrogen atom or a methyl group, $A^{f1}$ represent a $C_1$ to $C_6$ alkanediyl group, and $R^{f2}$ represents a $C_1$ to $C_{10}$ hydrocarbon group that has a fluorine atom.

Examples of the alkanediyl group for $A^{f1}$ include a chain alkanediyl group such as methylene, ethylene, propane-1,3-diyl, butane-1,4-diyl, pentane-1,5-diyl and hexane-1,6-diyl groups;

a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups.

The hydrocarbon group for $R^{f2}$ includes an aliphatic hydrocarbon group and an aromatic hydrocarbon group. The aliphatic hydrocarbon group includes a chain and a cyclic groups, and a combination thereof. The aliphatic hydrocarbon group is preferably an alkyl group and an alicyclic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the alicyclic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, cycloheptyl, cyclooctyl, and cyclodecyl groups. Examples of the polycyclic hydrocarbon groups include decahydronaphthyl, adamantyl, 2-alkyladamantane-2-yl, 1-(adamantane-1-yl) alkane-1-yl, norbornyl, methylnorbornyl and isobornyl groups.

Examples of the hydrocarbon group having a fluorine atom for $R^{f2}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, 1-(trifluoromethyl)-2,2,2-trifluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoromethyl) methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)2,2,3,3,3-pentafluoropropyl, 2-(perfluorobutyl)ethyl, 1,1,2,2,3,3,4,4,5,5-decafluorohexyl, 1,1,2,2,3,3,4,4,5,5,6,6-dodecafluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In formula (a4-2), $A^{f1}$ is preferably a $C_2$ to $C_4$ alkanediyl group, and more preferably ethylene group.

$R^{f2}$ is preferably a $C_1$ to $C_6$ fluorinated alkyl group:

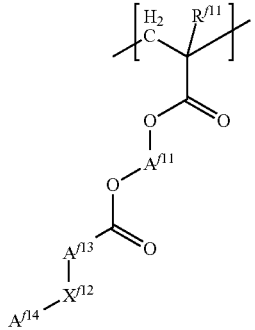

(a4-3)

In the formula, $R^{f11}$ represents a hydrogen atom or a methyl group, $A^{f11}$ represent a $C_1$ to $C_6$ alkanediyl group, $A^{f13}$ represents a $C_1$ to $C_{18}$ aliphatic hydrocarbon group that may has a fluorine atom, $X^{f12}$ represents an oxycarbonyl group or a carbonyloxy group, $A^{f14}$ represents a $C_1$ to $C_{17}$ aliphatic hydrocarbon group that may has a fluorine atom, and provided that at least one of $A^{f13}$ and $A^{f14}$ represents an aliphatic hydrocarbon group having a fluorine atom.

Examples of the alkanediyl group for $A^{f11}$ are the same examples as the alkanediyl group of $A^{f1}$.

Examples of the aliphatic hydrocarbon group for $A^{f13}$ include a divalent chain or cyclic aliphatic hydrocarbon group, and a combination thereof. The aliphatic hydrocarbon group may have a carbon-carbon unsaturated bond, and is preferably a saturated aliphatic hydrocarbon group.

The aliphatic hydrocarbon group that may has a fluorine atom for $A^{f13}$ preferably include the saturated aliphatic hydrocarbon group that may has a fluorine atom, and more preferably a perfuloroalkandiyl group.

Examples of the divalent chain aliphatic hydrocarbon that may have a fluorine atom include an alkanediyl group such as methylene, ethylene, propanediyl, butanediyl and pentanediyl groups; a perfluoroalkanediyl group such as difluoromethylene, perfluoroethylene, perfluoropropanediyl, perfluorobutanediyl and perfluoropentanediyl groups.

The divalent cyclic aliphatic hydrocarbon group that may have a fluorine atom may be a group having a monocyclic or polycyclic group.

Examples of the monocyclic aliphatic hydrocarbon group include cyclohexanediyl and perfluorocyclohexanediyl groups.

Examples of the polycyclic aliphatic hydrocarbon group include adamantanediyl, norbornanediyl, and perfluoroadamantanediyl groups.

Examples of the aliphatic hydrocarbon group for $A^{f14}$ include a chain or cyclic hydrocarbon group, and a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f14}$ is preferably the saturated aliphatic hydrocarbon group that may have a fluorine atom.

Examples of the chain aliphatic hydrocarbon group that may have a fluorine atom include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, pentyl, hexyl, perfluorohexyl, hepthyl, perfluoroheptyl, octyl and perfluorooctyl groups.

The cyclic aliphatic hydrocarbon group that may have a halogen atom may be a monocyclic or polycyclic group. Examples of the group containing the monocyclic aliphatic hydrocarbon group include cyclopropylmethyl, cyclopropyl, cyclobutylmethyl, cyclopentyl, cyclohexyl and perfluorocyclohexyl groups. Examples of the group containing the polycyclic aliphatic hydrocarbon group include adamantyl, adamantylmethyl, norbornyl, norbornylmethyl, perfluoroadamantyl and perfluoroadamantylmethyl groups In the formula (a4-3), $A^{f11}$ is preferably an ethylene group.

The aliphatic hydrocarbon group for $A^{f13}$ is preferably a $C_1$ to $C_6$ aliphatic hydrocarbon group, more preferably a $C_2$ to $C_3$ aliphatic hydrocarbon group.

The aliphatic hydrocarbon group of $A^{f14}$ is preferably a $C_3$ to $C_{12}$ aliphatic hydrocarbon group, more preferably a $C_3$ to $C_{10}$ aliphatic hydrocarbon group. Among them, $A^{f14}$ is preferably a group containing a $C_3$ to $C_{12}$ alicyclic hydrocarbon group, more preferably cyclopropylmethyl, cyclopentyl, cyclohexyl, norbornyl and adamantyl groups.

Examples of the structural unit (a4-2) include structural units represented by formula (a4-1-1) to formula (a4-1-22).

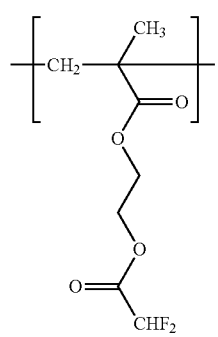 (a4-1-1)
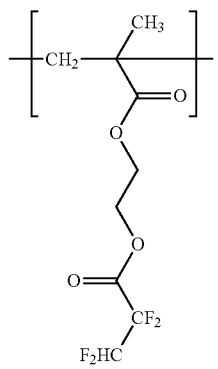 (a4-1-5)
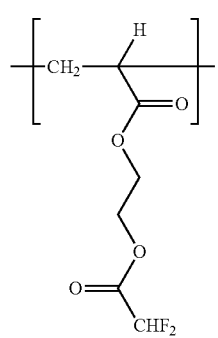 (a4-1-2)
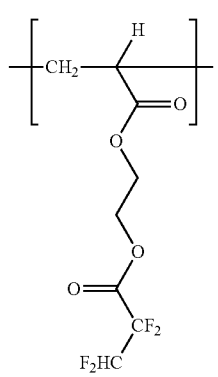 (a4-1-6)
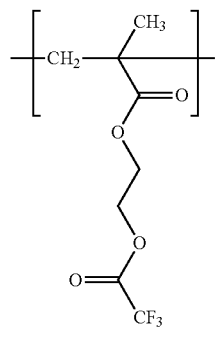 (a4-1-3)
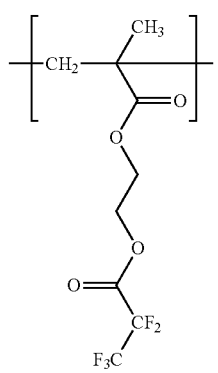 (a4-1-7)
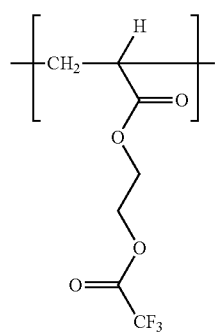 (a4-1-4)
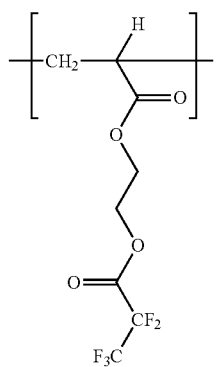 (a4-1-8)

(a4-1-9)
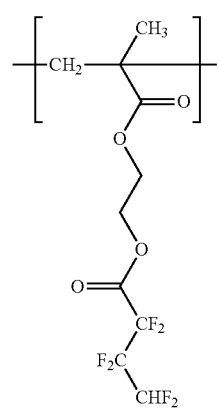
(a4-1-10)
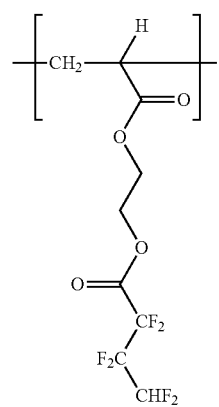
(a4-1-11)
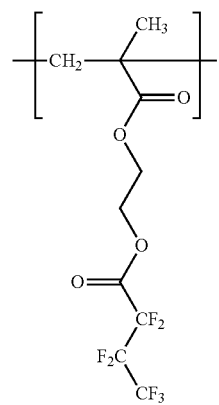
(a4-1-12)
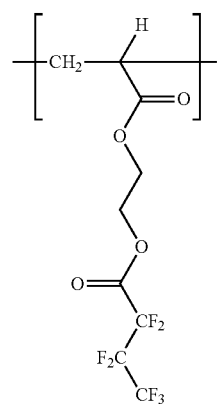
(a4-1-13)
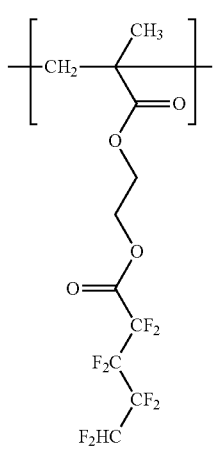
(a4-1-14)
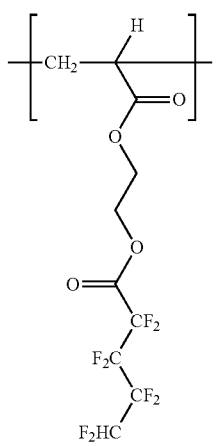
(a4-1-15)
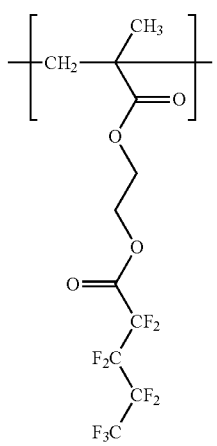

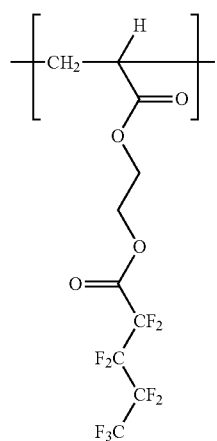
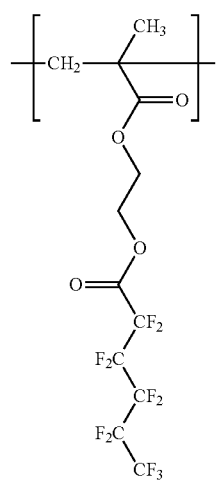

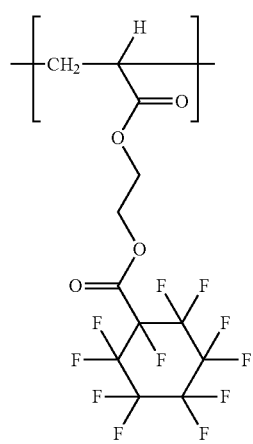
(a4-1-22)
Examples of the structural unit (a4-3) include structural units presented by formula (a4-1'-1) to formula (A4-1'-22).
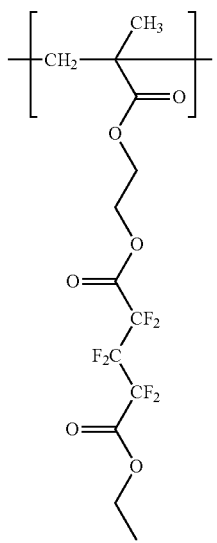
(a4-1'-1)
(a4-1'-2)
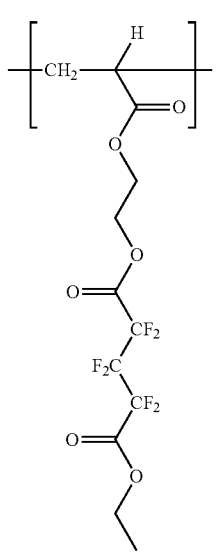
(a4-1'-3)
(a4-1'-4)
(a4-1'-5)
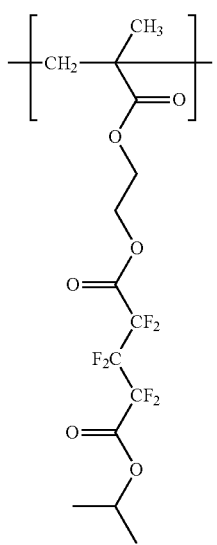

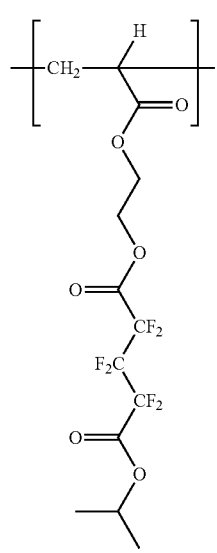
(a4-1'-6)
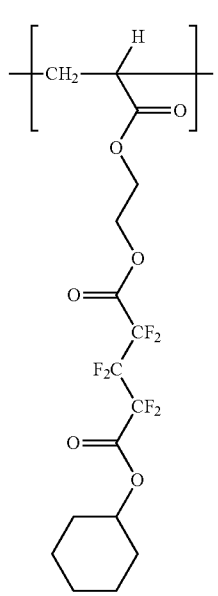
(a4-1'-8)
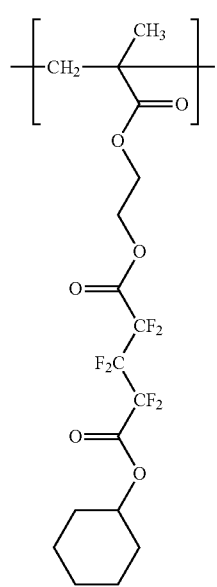
(a4-1'-7)
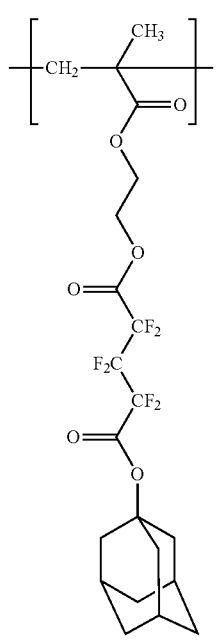
(a4-1'-9)

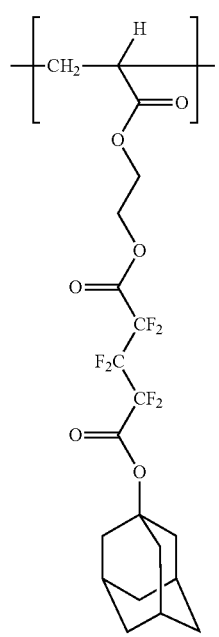
(a4-1'-10)
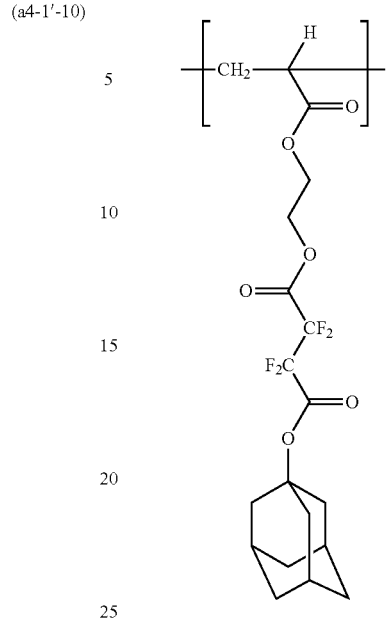
(a4-1'-12)
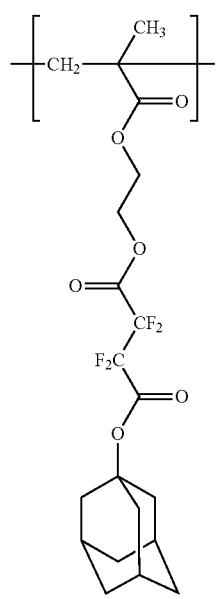
(a4-1'-11)
(a4-1'-13)

(a4-1'-14)
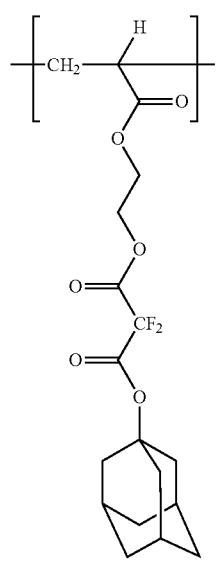
(a4-1'-16)
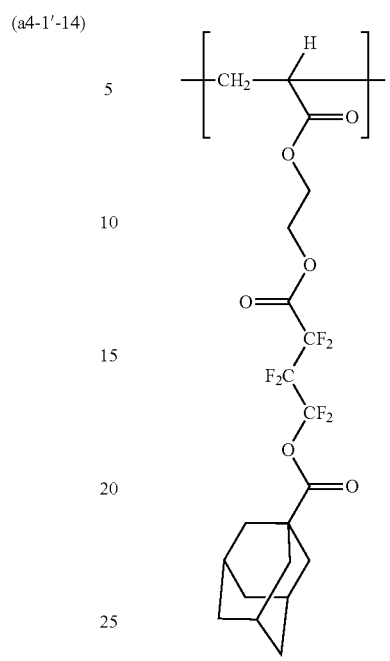
(a4-1'-15)
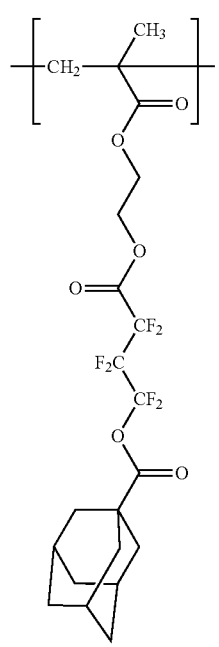
(a4-1'-17)
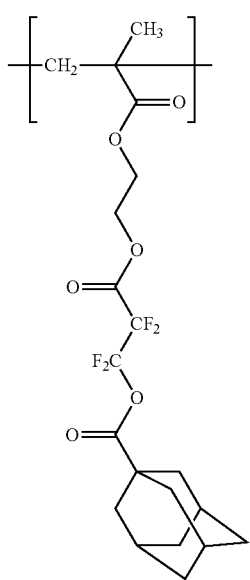

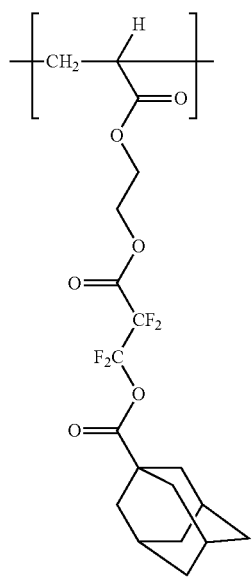
(a4-1'-18)
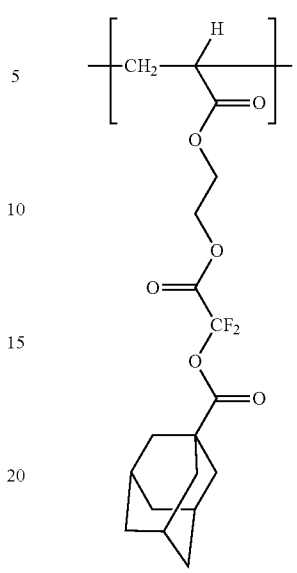
(a4-1'-20)
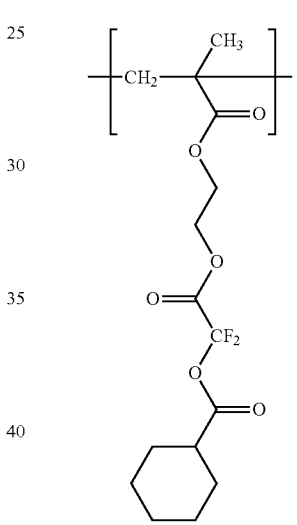
(a4-1'-21)
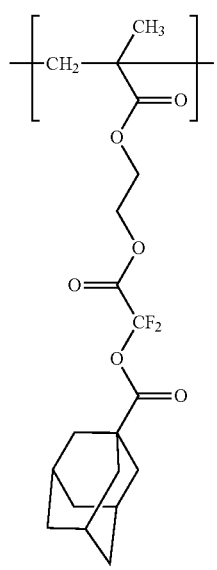
(a4-1'-19)
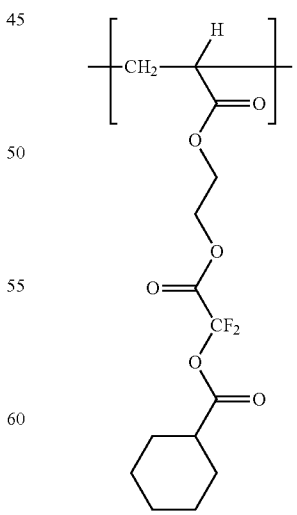
(a4-1'-22)
Examples of the structural unit (a4) include a structural unit presented by formula (a4-4):

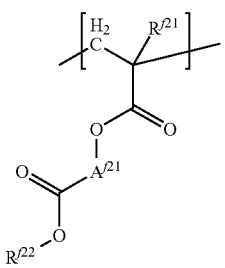
(a4-4)

wherein $R^{f21}$ represents a hydrogen atom or a methyl group, $A^{f21}$ represents $-(CH_2)_{j1}-$, $-(CH_2)_{j2}-O-(CH_2)_{j3}-$ or $-(CH_2)_{j4}-CO-O-(CH_2)_{j5}-$, j1 to j5 independently represents an integer of 1 to 6, and $R^{f22}$ represents a $C_1$ to $C_{10}$ hydrocarbon group having a fluorine atom.

Examples of the hydrocarbon group having a fluorine atom for $R^{f22}$ are the same examples as the hydrocarbon group described in $R^{f2}$ in formula (a4-2). $R^{f22}$ is preferably a $C_1$ to $C_{10}$ alkyl group having a fluorine atom or a $C_3$ to $C_{10}$ alicyclic hydrocarbon group having a fluorine atom, more preferably a $C_1$ to $C_{10}$ alkyl group having a fluorine atom, and still more preferably a $C_1$ to $C_6$ alkyl group having a fluorine atom.

In the formula (a4-4), $A^{f21}$ is preferably $-(CH_2)_{j1}-$, more preferably a methylene group or an ethylene group, and still more preferably a methylene group.

Examples of the structural unit represented by formula (a4-4) include the following ones.

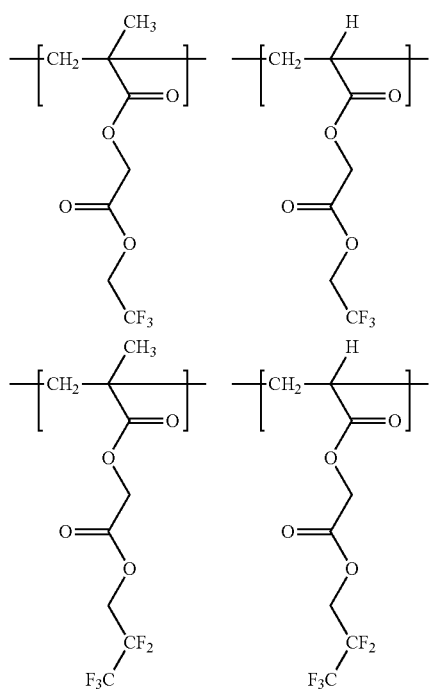

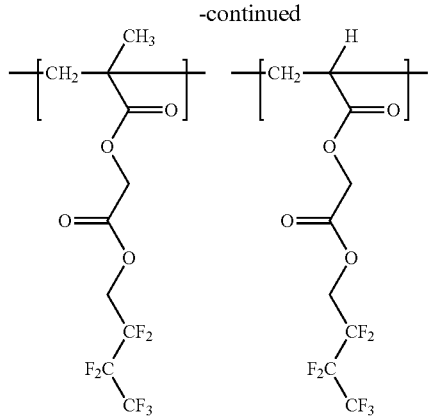

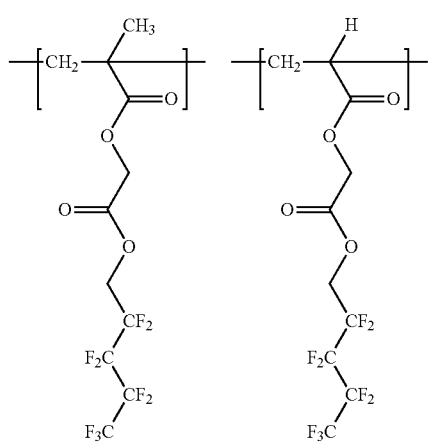

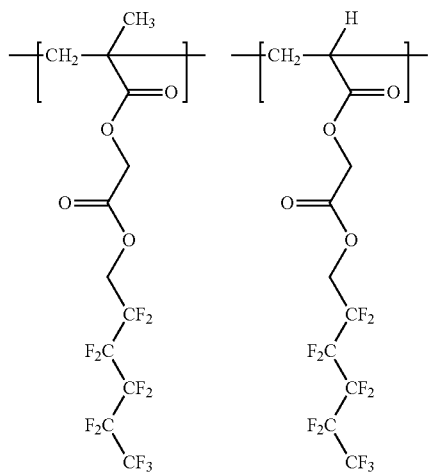

85
-continued
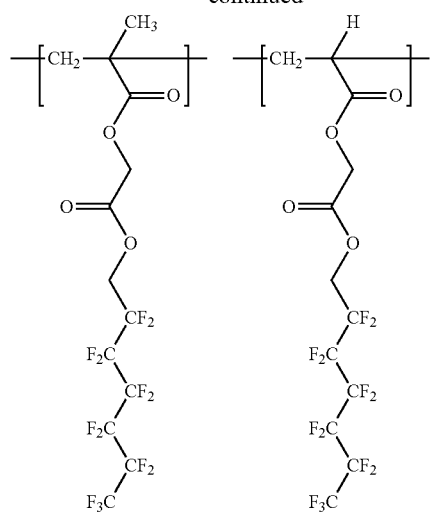
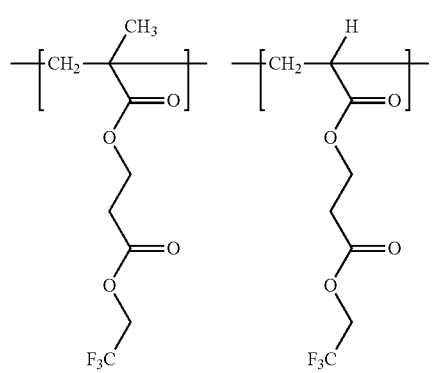
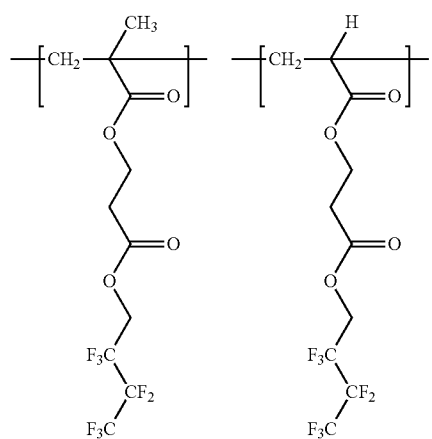
86
-continued
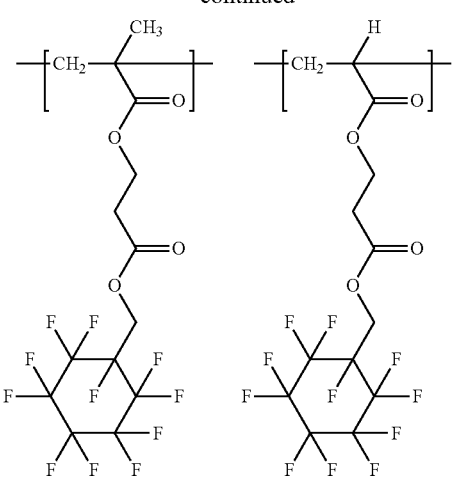
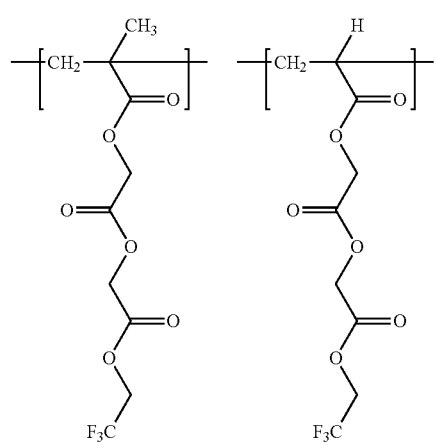
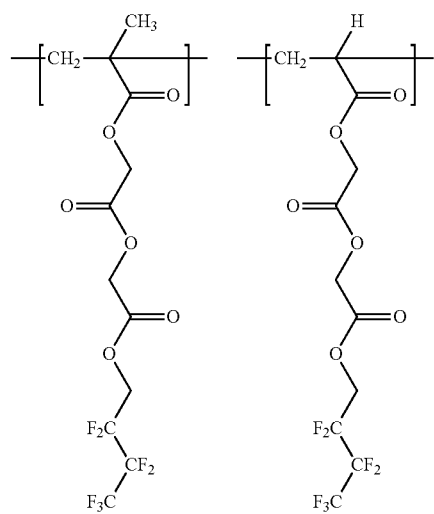

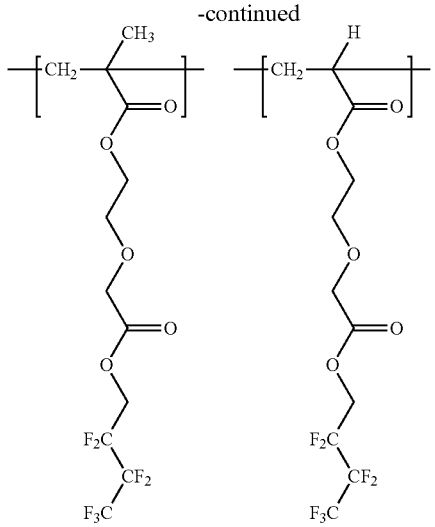

When the resin (A) contains the structural unit (a4), the proportion thereof is preferably 1 to 20% by mole, more preferably 2 to 15% by mole, still more preferably 3 to 10% by mole, with respect to the total structural units (100% by mole) of the resin (A).

<Structural Unit (a5)>

Examples of the non-leaving hydrocarbon group in the structural unit (a5) include a chain, branched or cyclic hydrocarbon group. Among them, the structural unit (a5) is preferably a structural unit containing an alicyclic hydrocarbon group.

The structural unit (a5) is, for example, a structural unit represented by formula (a5-1):

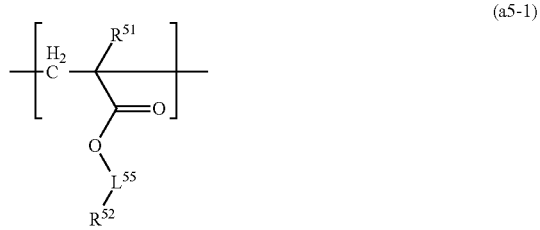

(a5-1)

wherein $R^{51}$ represents a hydrogen atom or a methyl group, $R^{52}$ represents a $C_3$ to $C_{18}$ alicyclic hydrocarbon group where a hydrogen atom may be replaced by a $C_1$ to $C_8$ aliphatic hydrocarbon group or a hydroxy group, provided that a hydrogen atom contained in the carbon atom bonded to $L^{55}$ is not replaced by the $C_1$ to $C_8$ aliphatic hydrocarbon group, and $L^{55}$ represents a single bond or a $C_1$ to $C_{18}$ divalent saturated hydrocarbon group where a methylene group may be replaced by an oxygen atom or a carbonyl group.

Examples of the alicyclic hydrocarbon group of $R^{52}$ include a monocyclic group or polycyclic group. Examples of the monocyclic alicyclic hydrocarbon group include cyclopropyl, cyclobutyl, cyclopentyl and cyclohexyl groups. Examples of the polycyclic alicyclic hydrocarbon group include adamantyl and norbornyl groups.

Examples of the $C_1$ to $C_8$ aliphatic hydrocarbon group include an alkyl group such as methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group having a substituent include 3-hydroxyadamantyl and 3-methyladamantyl.

$R^{52}$ is preferably an unsubstituted $C_3$ to $C_{18}$ alicyclic hydrocarbon group, and more preferably adamantyl, norbornyl and cyclohexyl groups.

Examples of the divalent saturated hydrocarbon group of $L^{55}$ include a divalent aliphatic saturated hydrocarbon group and a divalent alicyclic saturated hydrocarbon group, and a divalent aliphatic saturated hydrocarbon group is preferred.

Examples of the divalent aliphatic saturated hydrocarbon group include an alkanediyl group such as methylene, ethylene, propanediyl, butanediyl and pentanediyl groups.

Examples of the divalent alicyclic saturated hydrocarbon group include a monocyclic group and a polycyclic group. Examples of the monocyclic alicyclic saturated hydrocarbon groups include cycloalkanediyl such as cyclopentanediyl and cyclohexanediyl groups. Examples of the polycyclic saturated hydrocarbon groups include adamantanediyl and norbornanediyl groups.

Examples of the saturated hydrocarbon group in which a methylene group has been replaced by an oxygen atom or a carbonyl group include groups represented by formula (L1-1) to formula (L1-4). In the formula (L1-1) to formula (L1-4), * represents a binding position to an oxygen atom.

(L1-1)

(L1-2)

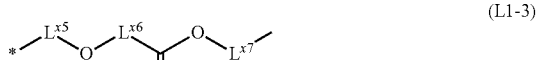

(L1-3)

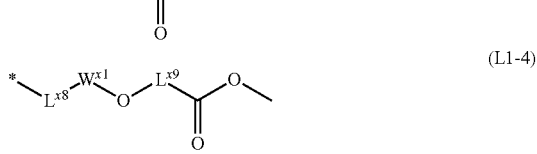

(L1-4)

In the formula, $X^{X1}$ represents an oxycarbonyl group or a carbonyloxy group, $L^{X1}$ represents a $C_1$ to $C_{16}$ divalent saturated aliphatic hydrocarbon group, $L^{X1}$ represents a single bond or a $C_1$ to $C_{15}$ divalent saturated hydrocarbon group, provided that the total carbon number contained in the group of $L^{X1}$ and $L^{X2}$ is 16 or less;

$L^{X3}$ represents a single bond or a $C_1$ to $C_{17}$ divalent saturated aliphatic hydrocarbon group, $L^{X4}$ represents a single bond or a $C_1$ to $C_{16}$ divalent saturated hydrocarbon group, provided that the total carbon number contained in the group of $L^{X3}$ and $L^{X4}$ is 17 or less;

$L^{X5}$ represents a $C_1$ to $C_{15}$ divalent saturated aliphatic hydrocarbon group, $L^{X6}$ and $L^{X7}$ independently represent a single bond or a $C_1$ to $C_{14}$ divalent saturated hydrocarbon group, provided that the total carbon number contained in the group of $L^{X5}$, $L^{X6}$ and $L^{X7}$ is 15 or less, $L^{X8}$ and $L^{X9}$ independently represent a single bond or a $C_1$ to $C_{12}$ divalent saturated hydrocarbon group, $W^{X1}$ represents a $C_3$ to $C_{15}$ divalent saturated alicyclic hydrocarbon group, provided that the total carbon number contained in the group of $L^{X8}$, $L^{X9}$ and $W^{X1}$ is 15 or less.

$L^{X1}$ is preferably a $C_1$ to $C_8$ divalent saturated aliphatic hydrocarbon group, and more preferably a methylene group or an ethylene group.

$L^{X2}$ is preferably a single bond or a $C_1$ to $C_8$ divalent saturated aliphatic hydrocarbon group, and more preferably a single bond.

$L^{X3}$ is preferably a $C_1$ to $C_8$ divalent saturated aliphatic hydrocarbon group.

$L^{X4}$ is preferably a single bond or a $C_1$ to $C_8$ divalent saturated aliphatic hydrocarbon group.

$L^{X5}$ is preferably a $C_1$ to $C_8$ divalent saturated aliphatic hydrocarbon group, and more preferably a methylene group or an ethylene group.

$L^{X6}$ is preferably a single bond or a $C_1$ to $C_8$ divalent saturated aliphatic hydrocarbon group, and more preferably a methylene group or an ethylene group.

$L^{X7}$ is preferably a single bond or a $C_1$ to $C_8$ divalent saturated aliphatic hydrocarbon group.

$L^{X8}$ is preferably a single bond or a $C_1$ to $C_8$ divalent saturated aliphatic hydrocarbon group, and more preferably a single bond or a methylene group.

$L^{X9}$ is preferably a single bond or a $C_1$ to $C_8$ divalent saturated aliphatic hydrocarbon group, and more preferably a single bond or a methylene group.

$W^{X1}$ is preferably a $C_3$ to $C_{10}$ divalent saturated alicyclic hydrocarbon group, and more preferably a cyclohexanediyl group or an adamantanediyl group.

Examples of the group represented by formula (L1-1) include the following ones.

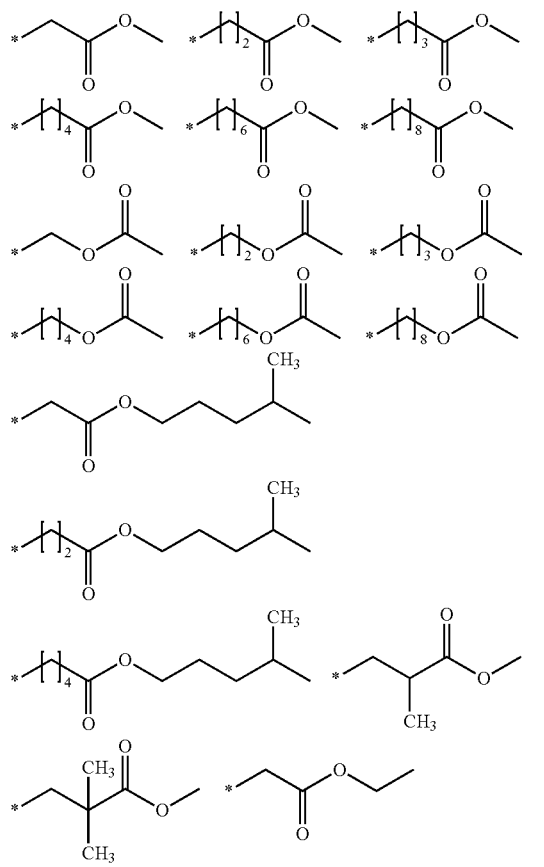

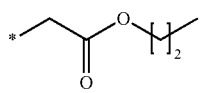

Examples of the group represented by formula (L1-2) include the following ones.

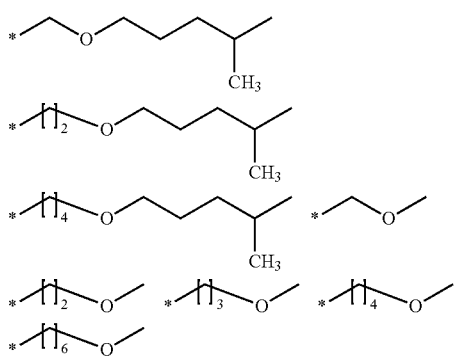

Examples of the group represented by formula (L1-3) include the following ones.

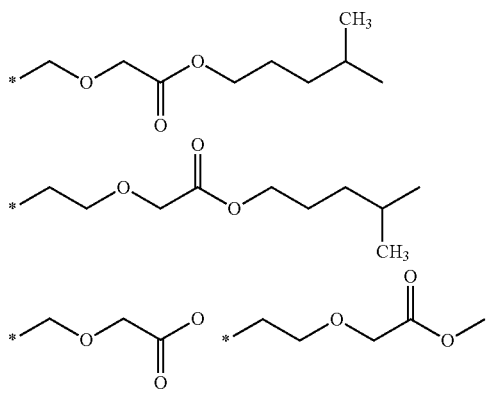

Examples of the group represented by formula (L1-4) include the following ones.

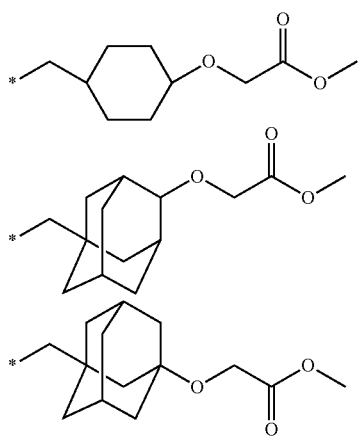

-continued
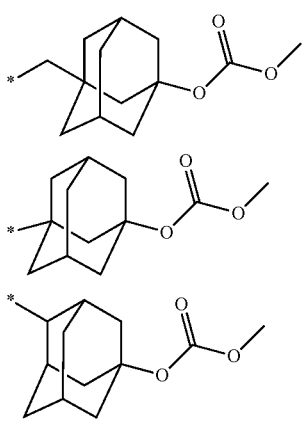
$L^{55}$ is preferably a single bond, methylene group, ethylene group or the groups represented by formula (L1-1), and more preferably a single bond or the groups represented by formula (L1-1).
Examples of the structural unit (a5-1) include the following ones.
(a5-1-1)
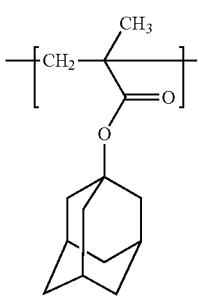
(a5-1-2)
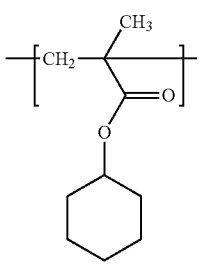
(a5-1-3)
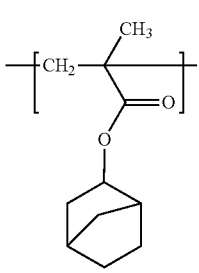
-continued
(a5-1-4)
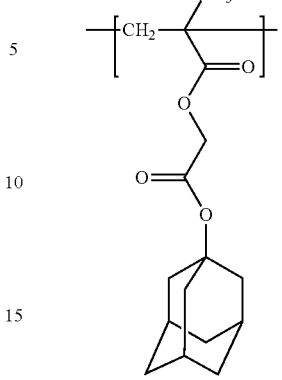
(a5-1-5)
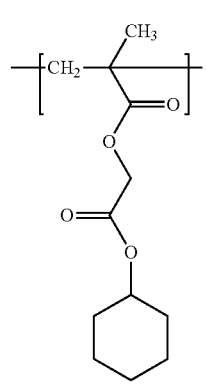
(a5-1-6)
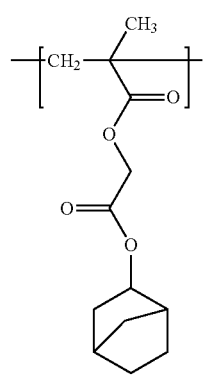
(a5-1-7)
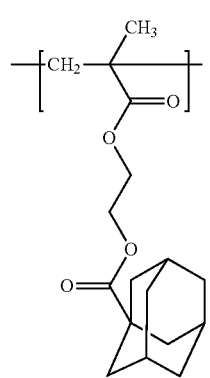

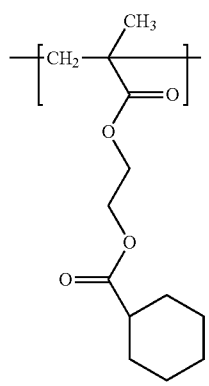 (a5-1-8)
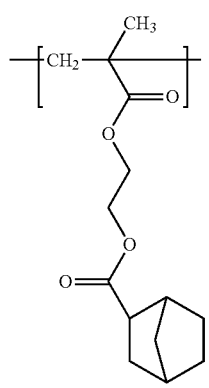 (a5-1-9)
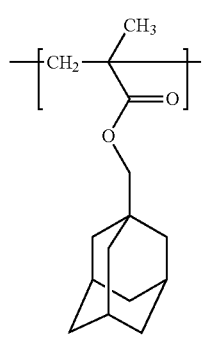 (a5-1-10)
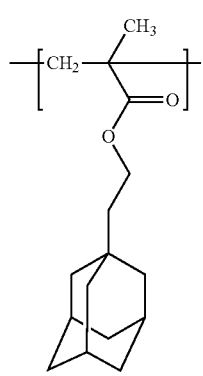 (a5-1-11)
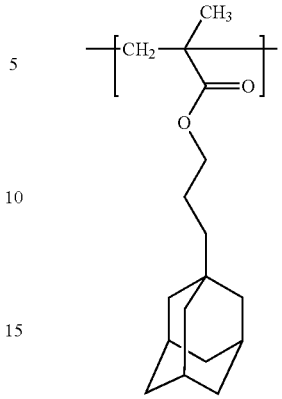 (a5-1-12)
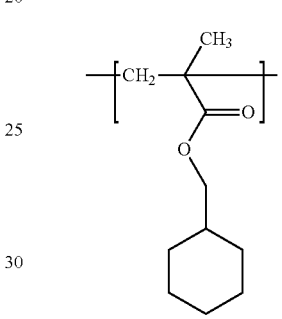 (a5-1-13)
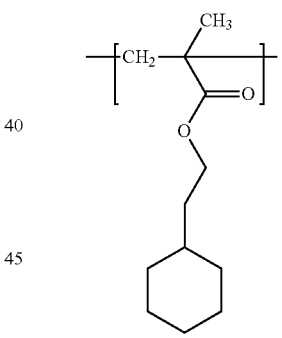 (a5-1-14)
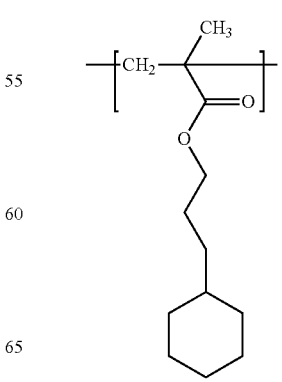 (a5-1-15)

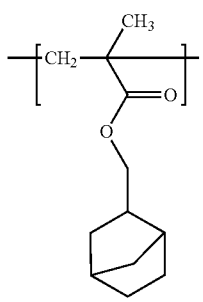
(a5-1-16)

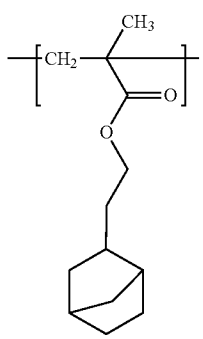
(a5-1-17)

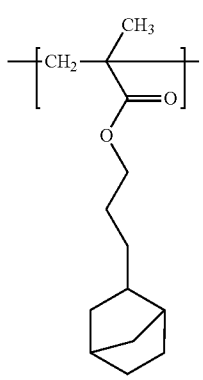
(a5-1-18)

Examples of the structural unit (a5) include the structural units of the formulae (a5-1-1) to (a5-1-18) in which a methyl group corresponding to $R^{55}$ has been replaced by a hydrogen atom.

When the resin (A) contains the structural unit (a5), the proportion thereof is preferably 1 to 30% by mole, more preferably 2 to 20% by mole, and still more preferably 3 to 15% by mole, with respect to the total structural units (100% by mole) of the resin (A).

The resin (A) may further have a known structural unit other than the structural unit described above.

The resin (A) preferably is a resin having the structural unit (1), the structural unit (a1) and the structural unit (s). In this resin, the structural unit (a1) is preferably at least one of the structural unit (a1-1) and the structural unit (a1-2) (preferably the structural unit having a cyclohexyl group or a cyclopentyl group), and more preferably is at least two of the structural unit (a1-1) and the structural unit (a1-2) (preferably the structural unit having a cyclohexyl group or a cyclopentyl group).

The structural unit (s) is preferably at least one of the structural unit (a2) or the structural unit (a3). The structural unit (a2) is preferably the structural unit represented by formula (a2-1). The structural unit (a3) is preferably at least one of the structural units (a3-1), (a3-2) or (a3-4).

The proportion of the structural unit derived from the monomer having an adamantyl group (in particular, the structural unit (a1-1)) in the resin (A) is preferably 15% by mole or more with respect to the structural units (a1). As the mole ratio of the structural unit derived from the monomer having an adamantyl group increases within this range, the dry etching resistance of the resulting resist improves.

The resin (A) can be produced by a known polymerization method, for example, radical polymerization method, using one or more kind(s) of monomers as described above. The proportions of the structural units in the resin (A) can be adjusted by changing the amount of a monomer used in polymerization.

The weight average molecular weight of the resin (A) is preferably 2,000 or more (more preferably 2,500 or more, and still more preferably 3,000 or more), and 50,000 or less (more preferably 30,000 or less, and still more preferably 15,000 or less).

The weight average molecular weight is a value determined by gel permeation chromatography using polystyrene as the standard product. The detailed condition of this analysis is described in Examples.

<Resist Composition>

The resist composition of the present disclosure contains a resin and an acid generator. The resist composition preferably contains at least one of resin (A) and the salt (I). The resist composition may preferably contain resin (A), more preferably the resin (A) further having a structural unit (a1). The resist composition more preferably contains resin (A) and the salt (I).

The resist composition preferably further contains a quencher (which is sometimes referred to as "quencher (C)") and/or a solvent (which is sometimes referred to as "solvent (E)").

<Resin for the Resist Composition>

The resist composition of the present disclosure contains a resin which has a structural unit having an acid-labile group. Examples of the resin include the resin (A), a resin having the structural unit (a1) but no structural unit (1). The resin having the structural unit (a1) but no structural unit (1) is sometimes referred to as "resin (AA)".

The resin (AA) may further have the structural unit (s) including the structural unit (t). Among them, the resin (A) is preferred.

The resist composition may further contain a resin which has no acid-labile group.

Examples of the resin which has no acid-labile group include a resin consisting of the structural unit (s) such as the structural unit (a2), the structural unit (a3), and the structural unit (t), preferably a resin consisting of the structural unit (t) such as a resin having the structural unit (a4) and having no the structural unit (a1). The resin having the structural unit (a4) and having no the structural unit (a1) is sometimes referred to as "resin (X)". Among them, the resin (X) is preferred.

The resin (X) may further have the structural unit (a2), the structural unit (a3) and other structural unit derived from a known monomer.

In the resin (X), the proportion of the structural unit (a4) is preferably 40% by mole or more, and more preferably 45% by mole or more, and still more preferably 50% by mole with respect to the total structural units (100% by mole) constituting the resin (X).

When the resist composition contains the resin (X), the proportion thereof is preferably 1 to 60 parts by mass, more preferably 1 to 50 parts by mass, and still more preferably 2 to 40 parts by mass, in particular preferably 2 to 30 parts by mass, with respect to 100 parts by mass of the resin having an acid-labile group, i.e., that of the resins (A) and (AA).

The weight average molecular weight of the resin (X) is preferably 5,000 or more (more preferably 6,000 or more), and 80,000 or less (more preferably 60,000 or less). The method of measuring of the weight average molecular weight of the resin (X) is the same as the resin (A).

The total proportion of the resins is preferably 80% by mass to 99% by mass, more preferably 90% by mass to 99% by mass, with respect to the total amount of solid components of the resist composition.

The proportion of the solid components in the resist composition and that of the resins in the solid components can be measured with a known analytical method such as liquid chromatography and gas chromatography.

<Acid Generator>

The resist composition of the present disclosure may contain an acid generator consisting of the salt (I), an acid generator consisting of an acid generator (B) other than the salt (I), both of them. The resist composition preferably contains the acid generator (B). The acid generator is a compound which can be decomposed by light to generate an acid. The acid acts catalytically to the resin (A) or the resin (AA), resulting in removing a leaving group from the resin.

When the salt (I) is used as the acid generator, the content of the salt (I) is preferably 1 parts by mass to 20 parts by mass, and preferably 2 parts by mass to 15 parts by mass, with respect to 100 parts by mass of the resins (A) and (AA).

<Acid Generator (B)>

The acid generator (B) may be any an ionic acid generator and a non-ionic acid generator, and preferably an ionic acid generator.

Examples of the nonionic compounds for the acid generator include organic halogenated compounds; sulfonate esters, e.g. 2-nitrobenzylester, aromatic sulfonates, oxime-sulfonate, N-sulfonyloxyimide, sulfonyloxyketone, and diazonaphtoquione 4-sulfonate; sulfones, e.g., disulfone, ketosulfone, and sulfonium diazomethane. The ionic compounds for the acid generator include onium salts having an onium cation, e.g., diazonium salts, phosphonium salts, sulfonium salts and iodonium salts. Examples of the anions of onium salt include a sulfonic acid anion, a sulfonylimide anion, sulfonylmethide anion.

As the acid generator, the compounds giving an acid by radiation can be used, which are mentioned in JP63-26653A1, JP55-164824A1, JP62-69263A1, JP63-146038A1, JP63-163452A1, JP62-153853A1, JP63-146029A1, U.S. Pat. Nos. 3,779,778B1, 3,849,137B1, DE3914407 and EP126,712A1. The acid generator for the photoresist composition can be produced by the method described in the above-mentioned documents.

The acid generator is preferably a fluorine-containing compound, more preferably salt represented by formula (B1) (which is sometimes referred to as "acid generator (B1)"):

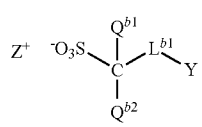

(B1)

wherein $Q^{b1}$ and $Q^{b2}$ respectively represent a fluorine atom or a $C_1$ to $C_6$ perfluoroalkyl group, $L^{b1}$ represents a divalent $C_1$ to $C_{24}$ saturated hydrocarbon group where a methylene group may be replaced by an oxygen atom or a carbonyl group and where a hydrogen atom may be replaced by a hydroxyl group or fluorine atom, and Y represents an optionally substituted methyl group, or an optionally substituted $C_3$ to $C_{18}$ alicyclic hydrocarbon group where a methylene group may be replaced by an oxygen atom, a carbonyl group or a sulfonyl group, or an optionally substituted methyl group, and $Z^+$ represents an organic cation.

Examples of the perfluoroalkyl group of $Q^{b1}$ and $Q^{b2}$ include trifluoromethyl, perfluoroethyl, perfluoropropyl, perfluoro-isopropyl, perfluorobutyl, perfluoro-sec-butyl, perfluoro-tert-butyl, perfluoropentyl and perfluorohexyl groups.

$Q^{b1}$ and $Q^{b2}$ independently are preferably trifluoromethyl or fluorine atom, and both of $Q^{b1}$ and $Q^{b2}$ are preferably a fluorine atom.

Examples of the divalent saturated hydrocarbon group of $L^{b1}$ include any of a chain or a branched alkanediylgroup, a divalent mono- or a poly-alicyclic saturated hydrocarbon group, and a combination thereof.

Specific examples of the chain alkanediyl group include methylene, ethylene, propane-1,3-diyl, propane-1,2-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl groups.

Specific examples of the branched chain alkanediyl group include ethane-1,1-diyl, propane-1,1-diyl, propane-1,2-diyl, propane-2,2-diyl, pentane-1,4-diyl, pentane-2,4-diyl, 2-methylpropane-1,3-diyl, 2-methylpropane-1,2-diyl and 2-methylbutane-1,4-diyl groups.

Specific examples of the mono-alicyclic saturated hydrocarbon group include a cycloalkanediyl group such as cyclobutan-1,3-diyl, cyclopentan-1,3-diyl, cyclohexane-1,4-diyl and cyclooctan-1,5-diyl groups.

Specific examples of the poly-alicyclic saturated hydrocarbon group include norbornane-1,4-diyl, norbornane-2,5-diyl, adamantane-1,5-diyl and adamantane-2,6-diyl groups.

Examples of the saturated hydrocarbon group of $L^{b1}$ in which a methylene group has been replaced by oxygen atom or a carbonyl group include groups represented by formula (b1-1) to formula (b1-3) below:

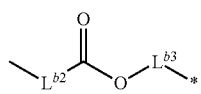

(b1-1)

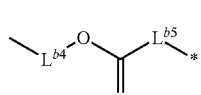

(b1-2)

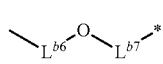

(b1-3)

wherein $L^{b2}$ represents a single bond or a $C_1$ to $C_{22}$ divalent saturated hydrocarbon group where a hydrogen atom may be replaced by a fluorine atom;

$L^{b3}$ represents a single bond or a $C_1$ to $C_{22}$ divalent saturated hydrocarbon group where a hydrogen atom may be replaced by a fluorine atom or a hydroxy group, and a methylene group may be replaced by an oxygen atom or a carbonyl group;

provided that the total carbon number contained in the group of $L^{b2}$ and $L^{b3}$ is 22 or less;

$L^{b4}$ represents a single bond or a $C_1$ to $C_{22}$ divalent saturated hydrocarbon group where a hydrogen atom may be replaced by a fluorine atom;

$L^{b5}$ represents a single bond or a $C_1$ to $C_{22}$ divalent saturated hydrocarbon group where a hydrogen atom may be replaced by a fluorine atom or a hydroxy group, and a methylene group may be replaced by an oxygen atom or a carbonyl group;

provided that the total carbon number contained in the group of $L^{b4}$ and $L^{b5}$ is 22 or less;

$L^{b6}$ represents a single bond or a $C_1$ to $C_{23}$ divalent saturated hydrocarbon group where a hydrogen atom may be replaced by a fluorine atom or a hydroxy group;

$L^{b7}$ represents a single bond or a $C_1$ to $C_{23}$ divalent saturated hydrocarbon group where a hydrogen atom may be replaced by a fluorine atom or a hydroxy group, and a methylene group may be replaced by an oxygen atom or a carbonyl group;

provided that the total carbon number contained in the group of $L^{b6}$ and $L^{b7}$ is 23 or less, and

* represents a binding position to —Y.

In formula (b1-1) to formula (b1-3), when a methylene group has been replaced by an oxygen atom or a carbonyl group, the carbon number of the saturated hydrocarbon group corresponds to the number of the carbon atom before replacement.

Examples of the divalent saturated hydrocarbon group are the same examples as the divalent saturated hydrocarbon group of $L^{b1}$.

$L^{b2}$ is preferably a single bond.

$L^{b3}$ is preferably a $C_1$ to $C_4$ divalent saturated hydrocarbon group.

$L^{b4}$ is preferably a $C_1$ to $C_8$ divalent saturated hydrocarbon group where a hydrogen atom may be replaced by a fluorine atom.

$L^{b5}$ is preferably a single bond or a $C_1$ to $C_8$ divalent saturated hydrocarbon group.

$L^{b6}$ is preferably a single bond or a $C_1$ to $C_4$ divalent saturated hydrocarbon group where a hydrogen atom may be replaced by a fluorine atom.

$L^{b7}$ is preferably a single bond or a $C_1$ to $C_{18}$ divalent saturated hydrocarbon group where a hydrogen atom may be replaced by a fluorine atom or a hydroxy group, and where a methylene group may be replaced by an oxygen atom or a carbonyl group.

Among them, the group represented by formula (b1-1) or formula (b1-3) is preferred as the divalent saturated hydrocarbon group in which a methylene group has been replaced by an oxygen atom or carbonyl group for $L^{b1}$.

Examples of the divalent group represented by formula (b1-1) include groups represented by formula (b1-4) to formula (b1-8) described below:

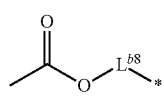

(b1-4)

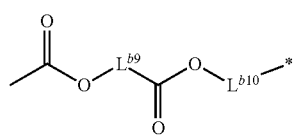

(b1-5)

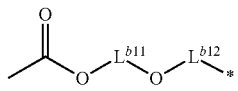

(b1-6)

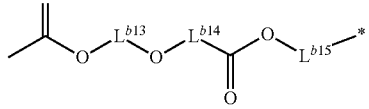

(b1-7)

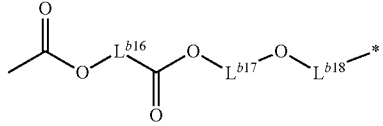

(b1-8)

wherein $L^{b8}$ represents a single bond or a $C_1$ to $C_{22}$ divalent saturated hydrocarbon group where a hydrogen atom may be replaced by a fluorine atom or a hydroxy group;

$L^{b9}$ represents a $C_1$ to $C_{20}$ divalent saturated hydrocarbon group;

$L^{b10}$ represents a single bond or a $C_1$ to $C_{19}$ divalent saturated hydrocarbon group where a hydrogen atom may be replaced by a fluorine atom or a hydroxy group;

provided that the total carbon number contained in the group of $L^{b9}$ and $L^{b10}$ is 20 or less;

$L^{b11}$ represents a $C_1$ to $C_{21}$ divalent saturated hydrocarbon group;

$L^{b12}$ represents a single bond or a $C_1$ to $C_{20}$ divalent saturated hydrocarbon group where a hydrogen atom may be replaced by a fluorine atom or a hydroxy group;

provided that the total carbon number contained in the group of $L^{b11}$ and $L^{b12}$ is 21 or less;

$L^{b13}$ represents a $C_1$ to $C_{19}$ divalent saturated hydrocarbon group;

$L^{b14}$ represents a single bond or a $C_1$ to $C_{18}$ divalent saturated hydrocarbon group;

$L^{b15}$ represents a single bond or a $C_1$ to $C_{18}$ divalent saturated hydrocarbon group where a hydrogen atom may be replaced by a fluorine atom or a hydroxy group;

provided that the total carbon number contained in the group of $L^{b3}$, $L^{b4}$ and $L^{b15}$ is 19 or less;

$L^{b6}$ represents a $C_1$ to $C_{18}$ divalent saturated hydrocarbon group;

$L^{b7}$ represents a $C_1$ to $C_{18}$ divalent saturated hydrocarbon group;

$L^{b18}$ represents a single bond or a $C_1$ to $C_{17}$ divalent saturated hydrocarbon group where a hydrogen atom may be replaced by a fluorine atom or a hydroxy group;

provided that the total carbon number contained in the group of $L^{b16}$, $L^{b17}$ and $L^{b18}$ is 19 or less.

$L^{b8}$ is preferably a $C_1$ to $C_4$ divalent saturated hydrocarbon group.

$L^{b9}$ is preferably a $C_1$ to $C_8$ divalent saturated hydrocarbon group.

$L^{b10}$ is preferably a single bond or a $C_1$ to $C_{19}$ divalent saturated hydrocarbon group, and more preferably a single bond or a $C_1$ to $C_8$ divalent saturated hydrocarbon group.

$L^{b11}$ is preferably a $C_1$ to $C_8$ divalent saturated hydrocarbon group.

$L^{b12}$ is preferably a single bond or a $C_1$ to $C_8$ divalent saturated hydrocarbon group.

$L^{b13}$ is preferably a $C_1$ to $C_{12}$ divalent saturated hydrocarbon group.

$L^{b14}$ is preferably a single bond or a $C_1$ to $C_6$ divalent saturated hydrocarbon group.

$L^{b15}$ is preferably a single bond or a $C_1$ to $C_{18}$ divalent saturated hydrocarbon group, and more preferably a single bond or a $C_1$ to $C_8$ divalent saturated hydrocarbon group.

$L^{b16}$ is preferably a $C_1$ to $C_{12}$ divalent saturated hydrocarbon group.

$L^{b17}$ is preferably a $C_1$ to $C_6$ divalent saturated hydrocarbon group.

$L^{b18}$ is preferably a single bond or a $C_1$ to $C_{17}$ divalent saturated hydrocarbon group, and more preferably a single bond or a $C_1$ to $C_4$ divalent saturated hydrocarbon group.

Examples of the divalent group represented by formula (b1-3) include groups represented by formula (b1-9) to formula (b1-11) described below:

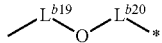  (b1-9)

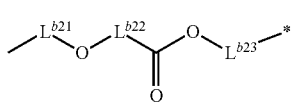  (b1-10)

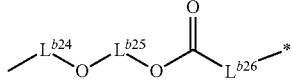  (b1-11)

wherein $L^{b19}$ represents a single bond or a $C_1$ to $C_{23}$ divalent saturated hydrocarbon group where a hydrogen atom may be replaced by a fluorine atom;

$L^{b20}$ represent a single bond or a $C_1$ to $C_{23}$ divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total carbon number contained in the group of $L^{b19}$ and $L^{b20}$ is 23 or less;

$L^{b21}$ represents a single bond or a $C_1$ to $C_{21}$ divalent saturated hydrocarbon group where a hydrogen atom may be replaced by a fluorine atom;

$L^{b22}$ represents a single bond or a $C_1$ to $C_{21}$ divalent saturated hydrocarbon group;

$L^{b23}$ represents a single bond or a $C_1$ to $C_{21}$ divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total carbon number contained in the group of $L^{b21}$, $L^{b22}$ and $L^{b23}$ is 21 or less;

$L^{b24}$ represents a single bond or a $C_1$ to $C_{20}$ divalent saturated hydrocarbon group where a hydrogen atom may be replaced by a fluorine atom;

$L^{b25}$ represents a single bond or a $C_1$ to $C_{21}$ divalent saturated hydrocarbon group;

$L^{b26}$ represents a single bond or a $C_1$ to $C_{20}$ divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total carbon number contained in the group of $L^{b24}$, $L^{b25}$ and $L^{b26}$ is 21 or less.

In formula (b1-9) to formula (b1-11), when a hydrogen atom has been replaced by an acyloxy group, the carbon number of the saturated hydrocarbon group corresponds to the number of the carbon atom, CO and O in addition to the carbon number of the saturated hydrocarbon group.

For formula (b1-9) to formula (b1-11), examples of the divalent saturated hydrocarbon group include an alkanediyl and a monocyclic or polycyclic divalent saturated hydrocarbon group, and a combination of two or more such groups.

Examples of the acyloxy group include acetyloxy, propionyloxy, butyryloxy, cyclohexyl carbonyloxy and adamantyl carbonyloxy groups.

Examples of the acyloxy group having a substituent include oxoadamantyl carbonyloxy, hydroxyadamantyl carbonyloxy, oxocyclohexyl carbonyloxy and hydroxycyclohexyl carbonyloxy groups.

Examples of the group represented by formula (b1-4) include the following ones.

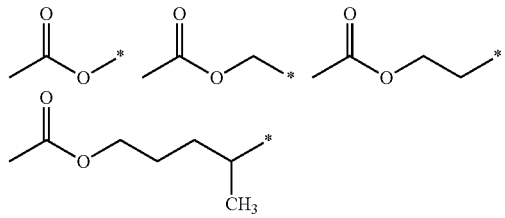

Examples of the group represented by formula (b1-5) include the following ones.

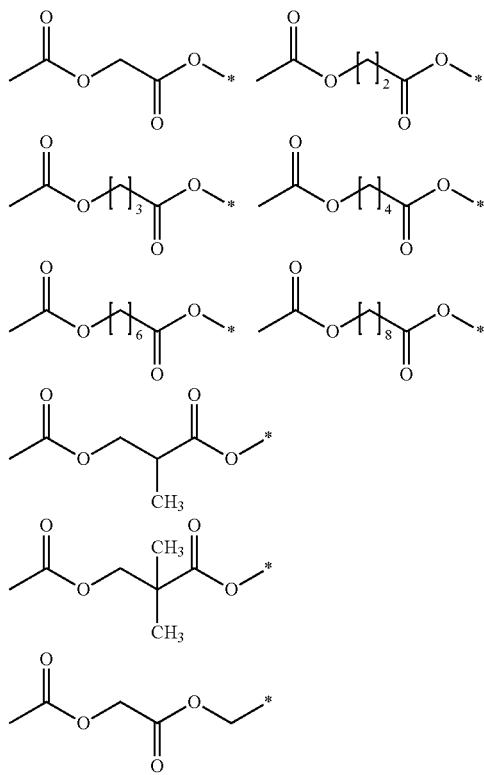

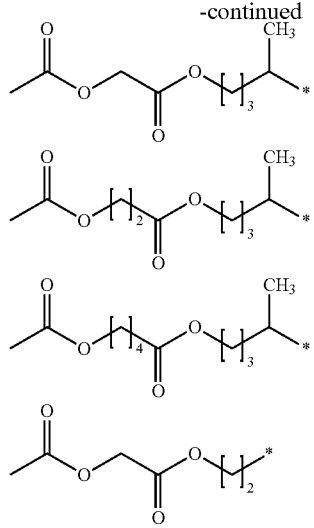
Examples of the group represented by formula (b1-6) include the following ones.
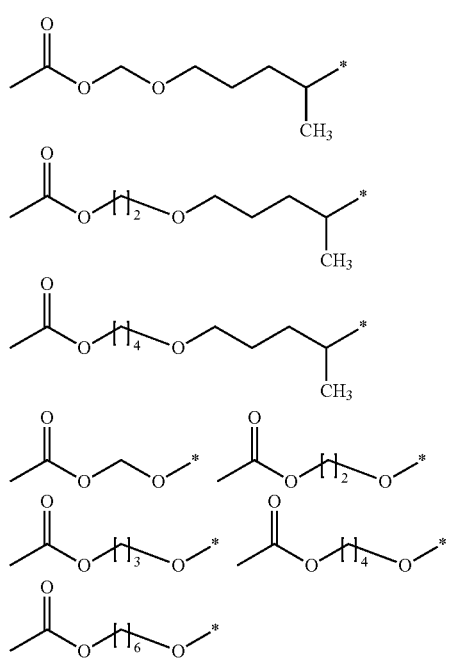
Examples of the group represented by formula (b1-7) include the following ones.
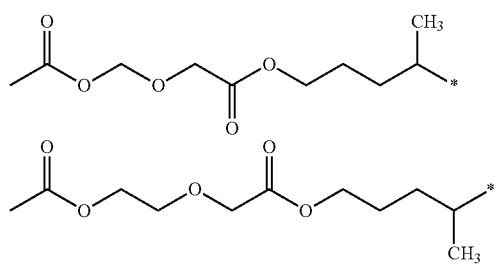
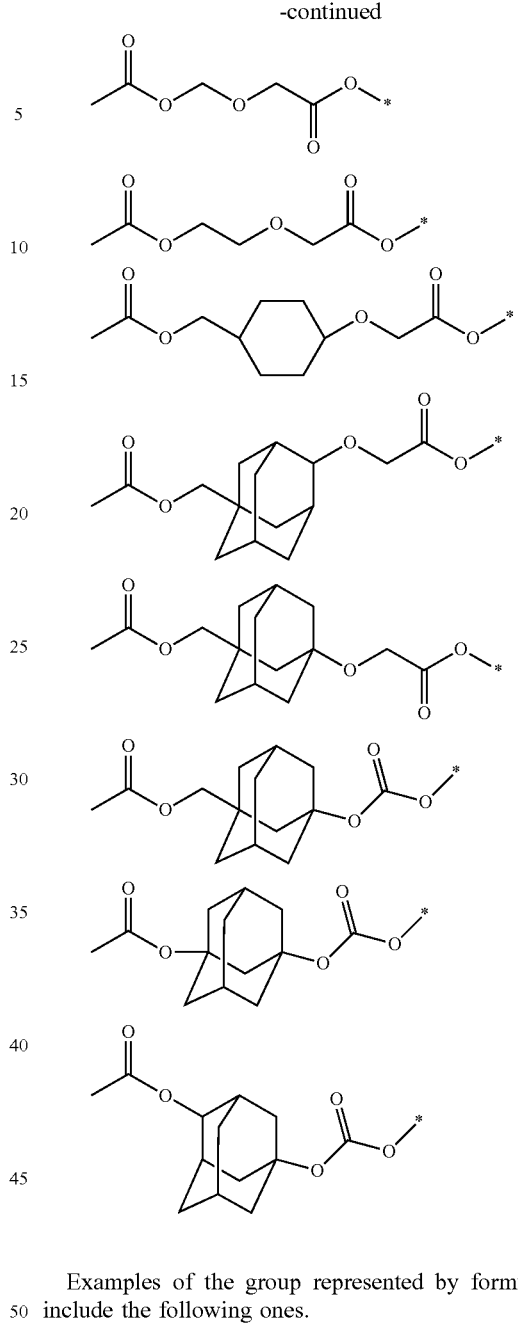
Examples of the group represented by formula (b1-8) include the following ones.
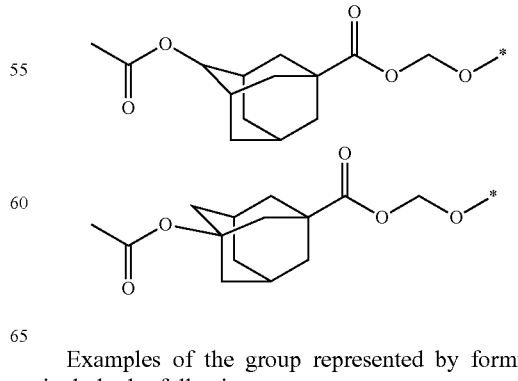
Examples of the group represented by formula (b1-2) include the following ones.

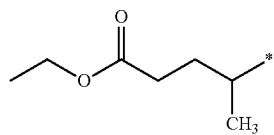
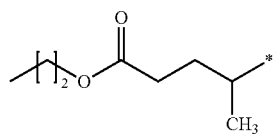
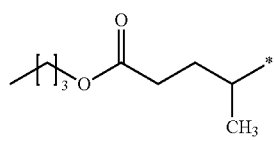
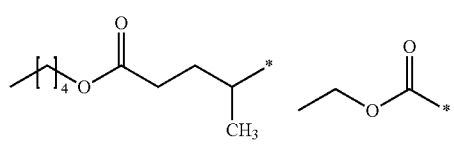
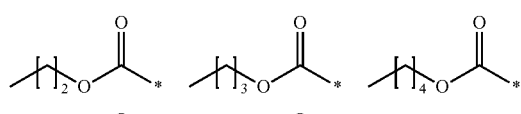
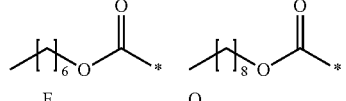
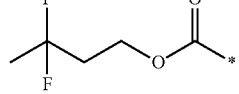
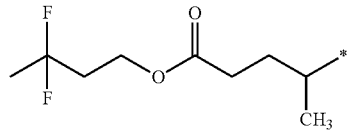
Examples of the group represented by formula (b1-9) include the following ones.
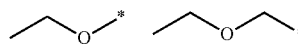
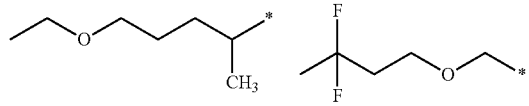
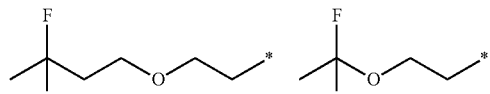
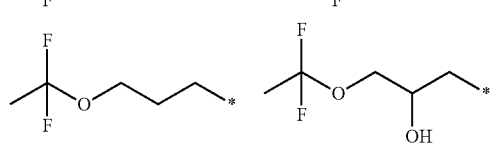
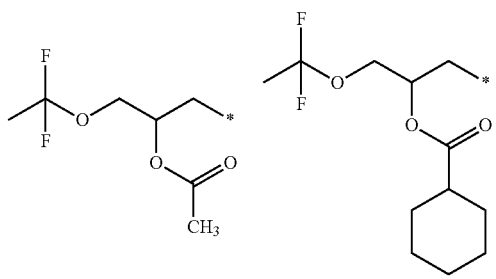
Examples of the group represented by formula (b1-10) include the following ones.
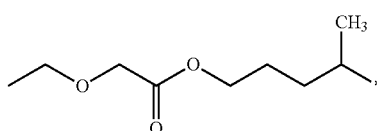
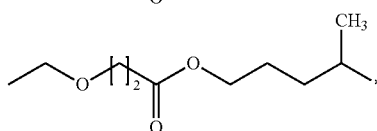
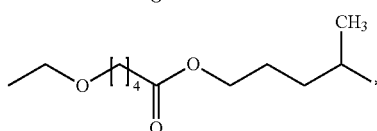
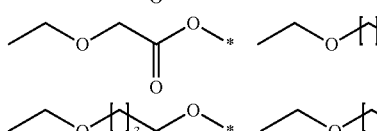
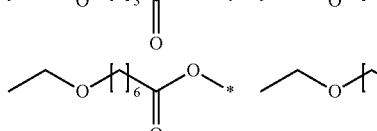
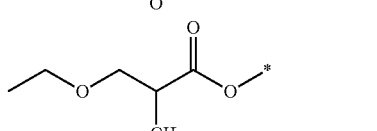
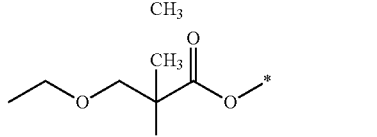
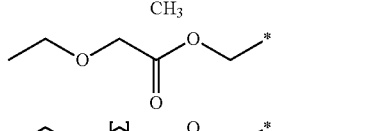
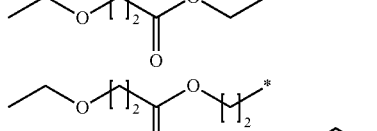
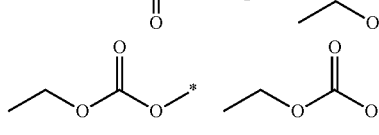

107
-continued
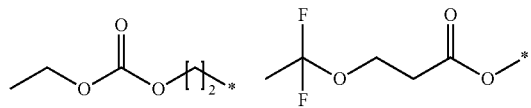
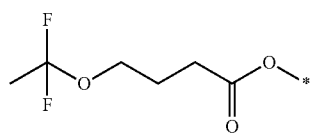
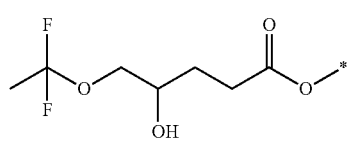
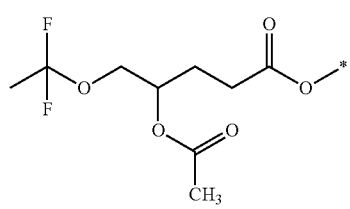
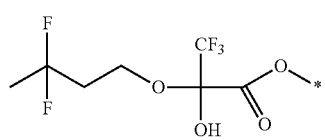
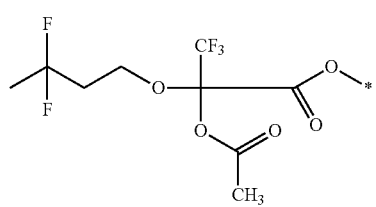
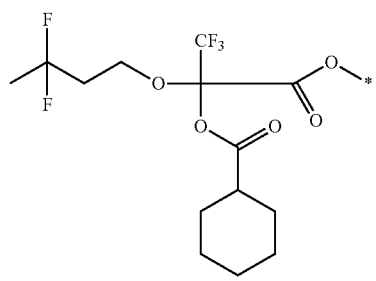
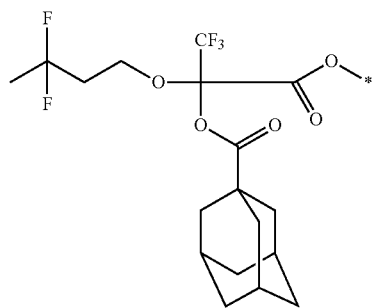
108
-continued
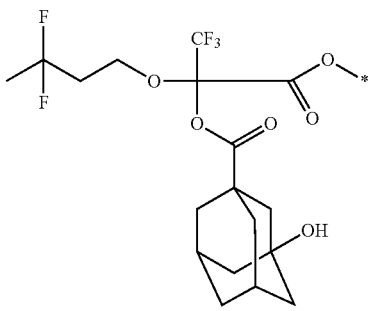
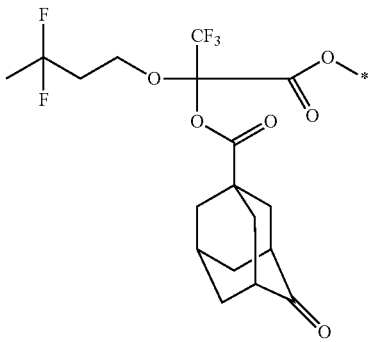 [SMILES: *OC(=O)C(OCCC(C)(F)F)(OC(=O)C12CC3CC(C1)C(=O)C(C3)C2)C(F)(F)F]
Examples of the group represented by formula (b1-1) include the following ones.
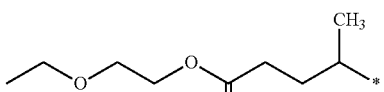
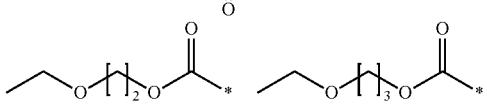
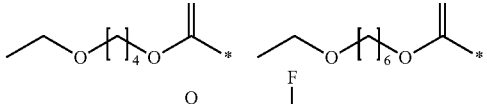
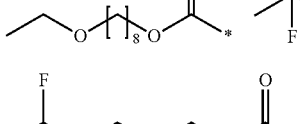
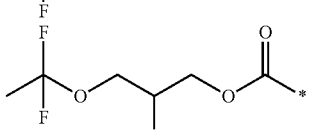
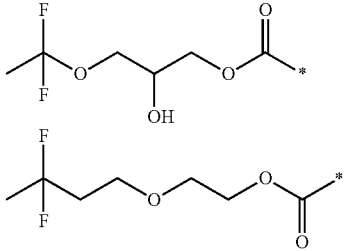

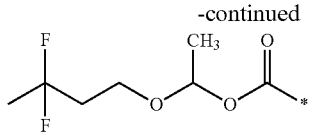
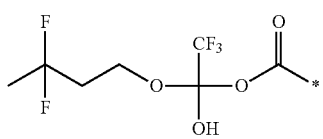
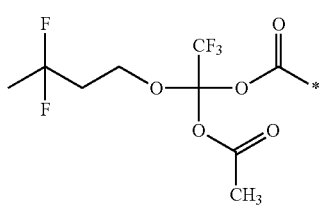
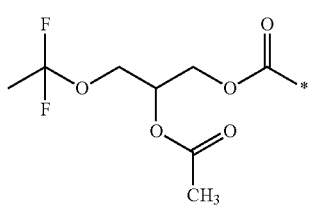
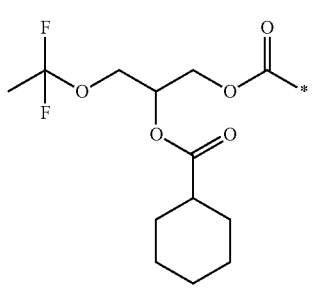
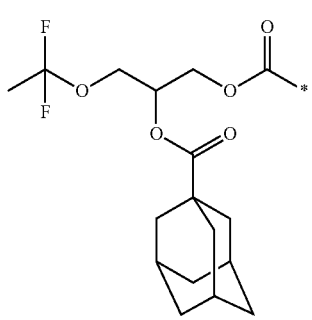
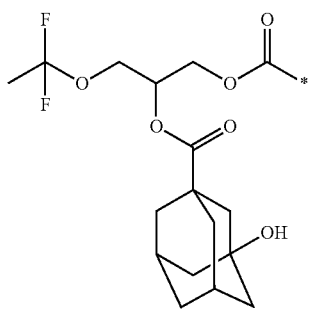
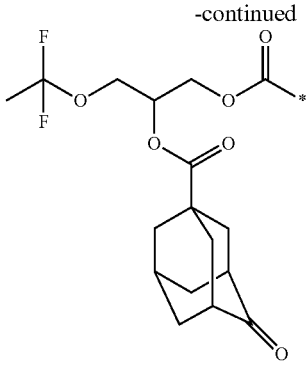
Examples of the monovalent alicyclic hydrocarbon group of Y include groups represented by formula (Y1) to formula (Y11).
Examples of the monovalent alicyclic hydrocarbon group of Y in which a methylene group has been replaced by an oxygen atom, a carbonyl group or a sulfonyl group include groups represented by formula (Y12) to formula (Y38).
 (Y1)
 (Y2)
 (Y3)
 (Y4)
 (Y5)
 (Y6)
 (Y7)
 (Y8)
 (Y9)

-continued
(Y10) 
(Y11) 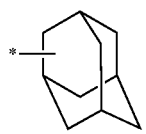
(Y12) 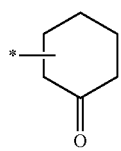
(Y13) 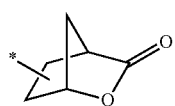
(Y14) 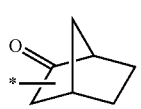
(Y15) 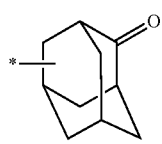
(Y16) 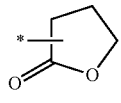
(Y17) 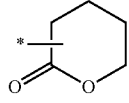
(Y18) 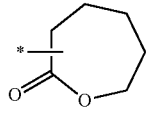
(Y19) 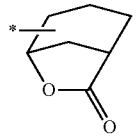
(Y20) 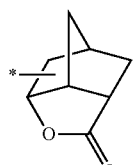
(Y21) 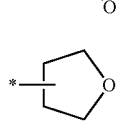
-continued
(Y22) 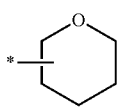
(Y23) 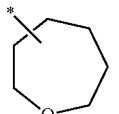
(Y24) 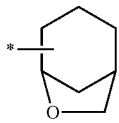
(Y25) 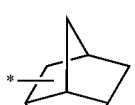
(Y26) 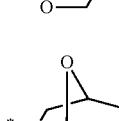
(Y27) 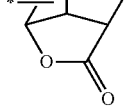
(Y28) 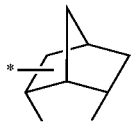
(Y29) 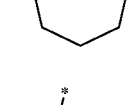
(Y30) 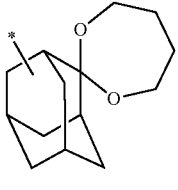

(Y31) 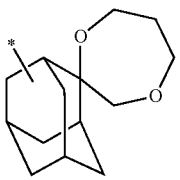

(Y32) 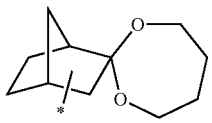

(Y33) 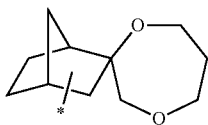

(Y34) 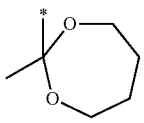

(Y35) 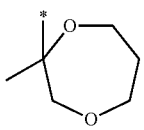

(Y36) 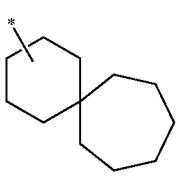

(Y37)

(Y38) 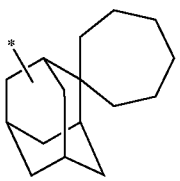

Y may have a ketal ring which is formed by a $C_1$ to $C_8$ alkanediyl group together with two oxygen atoms which have been replaced from two hydrogen atom contained in the alicyclic hydrocarbon group, or a structure in which two oxygen atoms are bonded to different carbon atoms respectively. When Y is a spiro ring represented by any of formula (Y28) to (Y33), the alkanediyl group between two oxygen atoms preferably has at least one of fluorine atom, and/or a methylene group contained in the alkanediyl group of the ketal ring and bonded to the oxygen atom preferably have no fluorine atom.

Among them, the alicyclic hydrocarbon group is preferably any one of groups represented by formulae (Y1) to (Y20) and formulae (Y30) and (Y31), more preferably any one of groups represented by formulae (Y11), (Y15), (Y16), (Y20), (Y30) and (Y31), and still more preferably a group represented by formula (Y11), (Y15) or (Y30).

Examples of the substituent of methyl group for Y include a halogen atom, a hydroxyl group, a $C_3$ to $C_{16}$ monovalent alicyclic hydrocarbon group, a $C_6$ to $C_{18}$ monovalent aromatic hydrocarbon group, a glycidyloxy group and —$(C_2)_{j2}$—O—CO—$R^{b1}$ in which $R^{b1}$ represents an $C_1$ to $C_{16}$ alkyl group, a $C_3$ to $C_{16}$ monovalent alicyclic hydrocarbon group, or a $C_6$ to $C_{18}$ monovalent aromatic hydrocarbon group, and j2 represents an integer of 0 to 4.

Examples of the substituent of the alicyclic hydrocarbon group for Y include a halogen atom, a hydroxyl group, a $C_1$ to $C_{12}$ alkyl group, a hydroxy group-containing $C_1$ to $C_{12}$ alkyl group, a $C_3$ to $C_{16}$ monovalent alicyclic hydrocarbon group, a $C_1$ to $C_{12}$ alkoxy group, a $C_6$ to $C_{18}$ monovalent aromatic hydrocarbon group, a $C_7$ to $C_{21}$ aralkyl group, a $C_2$ to $C_4$ acyl group, a glycidyloxy group and —$(CH_2)_{j2}$—O—CO—$R^{b1}$— in which $R^{b1}$ represents an $C_1$ to $C_{16}$ alkyl group, a $C_3$ to $C_{16}$ monovalent alicyclic hydrocarbon group, or a $C_6$ to $C_{18}$ monovalent aromatic hydrocarbon group, and j2 represents an integer of 0 to 4.

Examples of the hydroxy group-containing alkyl group include hydroxymethyl and hydroxyethyl groups Examples of the alkoxyl group include methoxy, ethoxy, propoxy, butoxy, pentyloxy, hexyloxy, heptyloxy, octyloxy, decyloxy and dodecyloxy groups.

Examples of the monovalent aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the aralkyl group include benzyl, phenethyl, phenylpropyl, naphthylmethyl and naphthylethyl groups.

Examples of the acyl group include acetyl, propionyl and butyryl groups.

Examples of the halogen atom include fluorine, chlorine, bromine and iodine atoms.

Examples of Y include the groups below. * represents a binding position to $L^{b1}$.

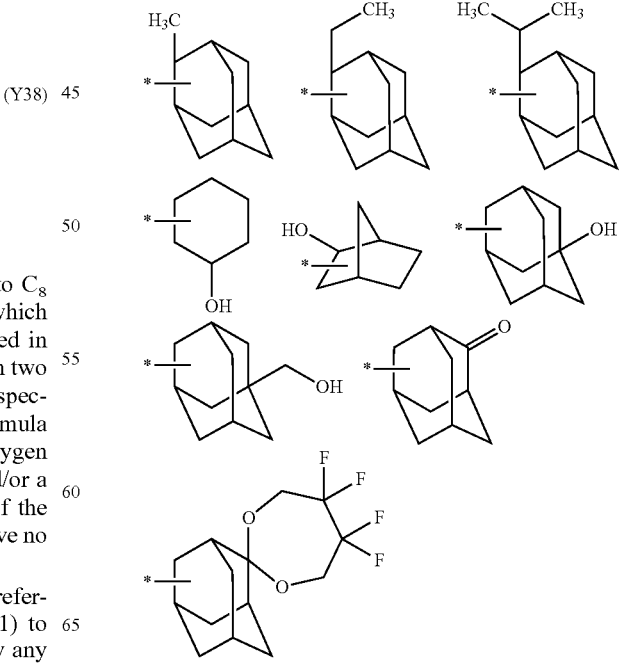

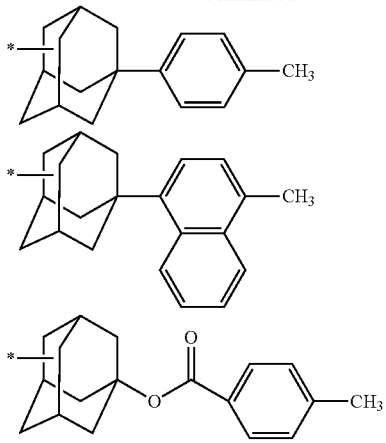

When Y is a methyl group and $L^{b1}$ is a $C_1$ to $C_{17}$ divalent chain or branched saturated hydrocarbon group, a —$CH_2$— which is bonded to Y and is in the divalent chain or branched saturated hydrocarbon group is preferably replaced by an oxygen atom or a carbonyl group.

Y is preferably a $C_3$ to $C_{18}$ monovalent alicyclic hydrocarbon group that may have a substituent, more preferably an adamantyl group that may have a substituent and one or more methylene group contained in the adamantyl group may be replaced by an oxygen atom, a carbonyl group or a sufonyl group, and still more preferably an adamantyl group, a hydroxyadamantyl group, an oxoadamantyl group or a group below.

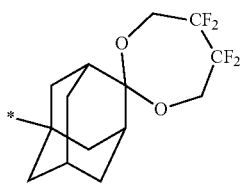 [SMILES: *C12CC3CC(C1)C1(OCC(F)(F)C(F)(F)CO1)C(C3)C2]

The sulfonic acid anion in the salt represented by formula (B1) is preferably an anions represented by formula (B1-A-1) to formula (B1-A-46), and more preferably an anions represented by formula (B1-A-1) to formula (B1-A-4), formula (B1-A-9), formula (B1-A-10), formulae (B1-A-24) to (B1-A-33) and formulae (B1-A-36) to (B1-A-40), below.

(B1-A-1)
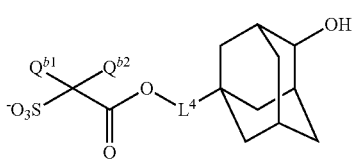

(B1-A-2)
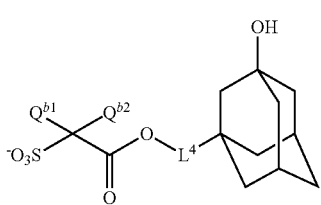

(B1-A-3)
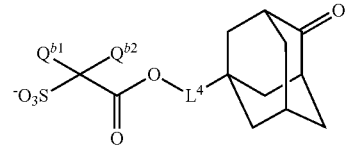

(B1-A-4)
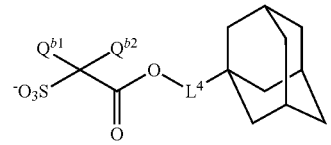

(B1-A-5)
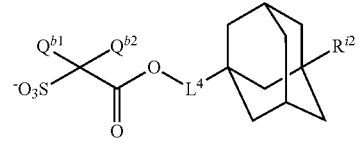

(B1-A-6)
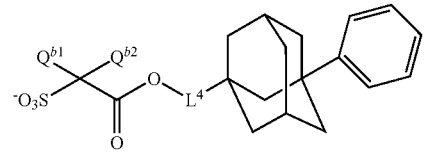

(B1-A-7)
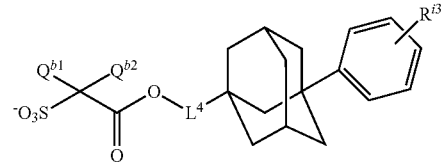

(B1-A-8)
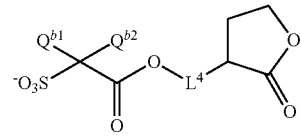

(B1-A-9)
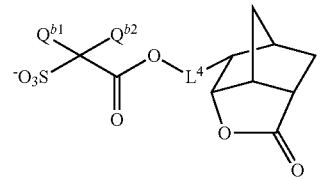

(B1-A-10)
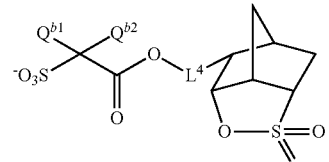

(B1-A-11)
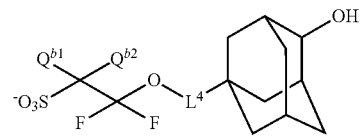

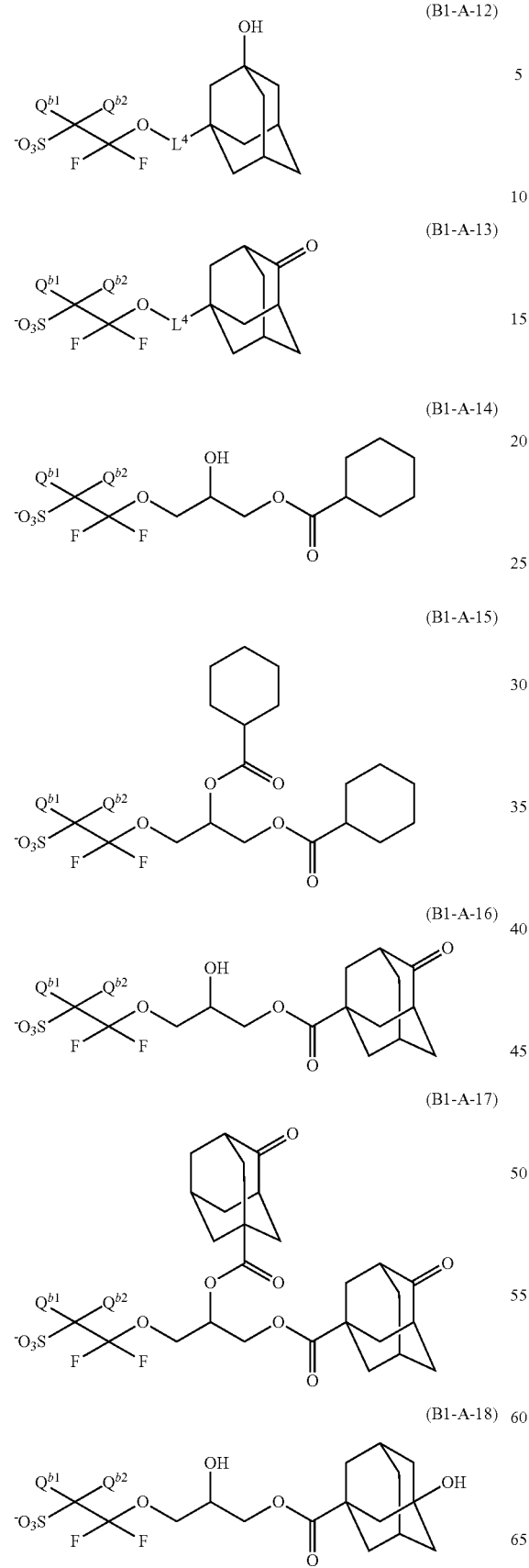
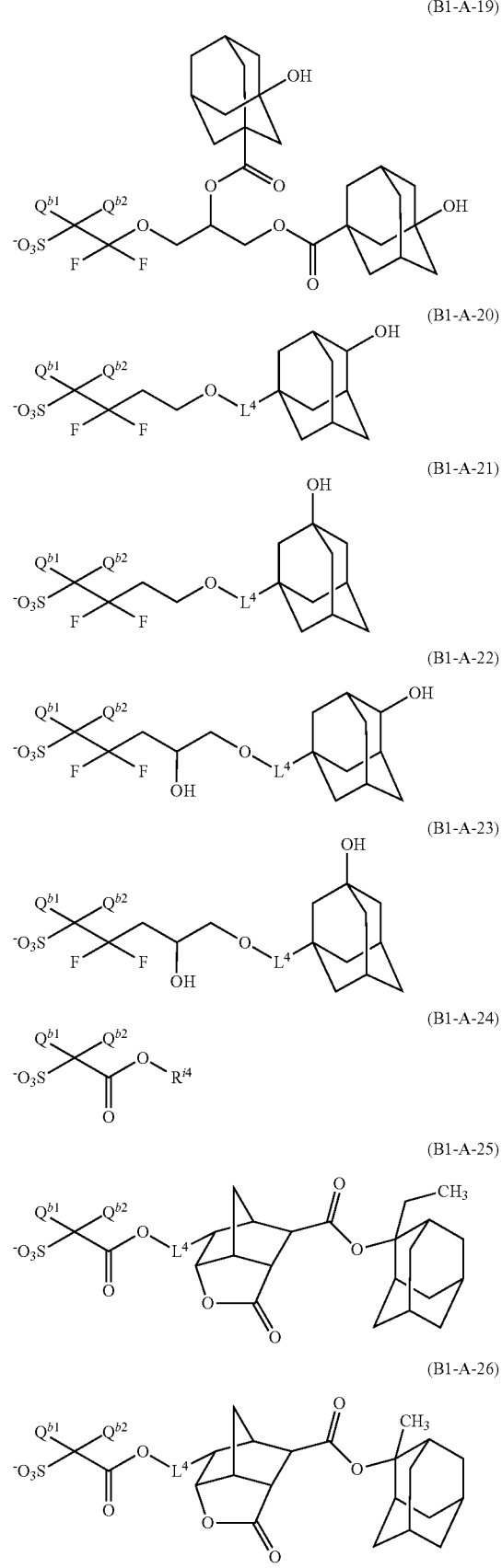

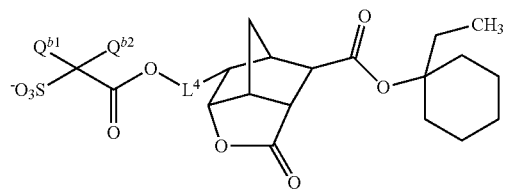 (B1-A-27)
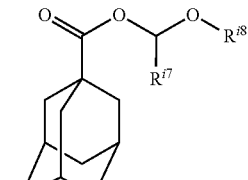 (B1-A-33)
 (B1-A-28)
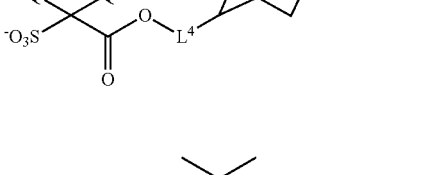 (B1-A-34)
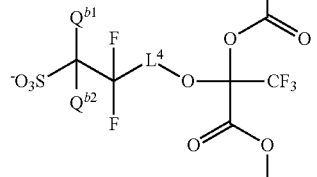 (B1-A-29)
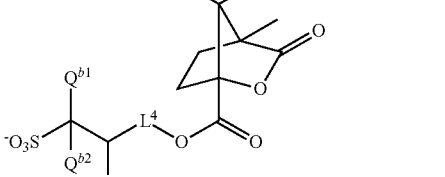 (B1-A-35)
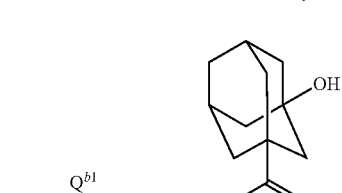 (B1-A-30)
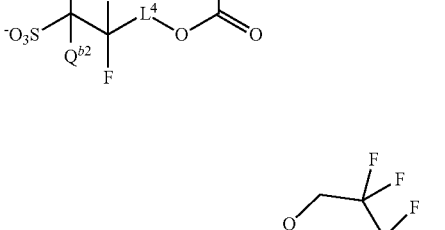 (B1-A-36)
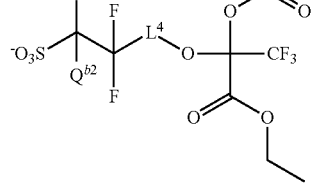 (B1-A-31)
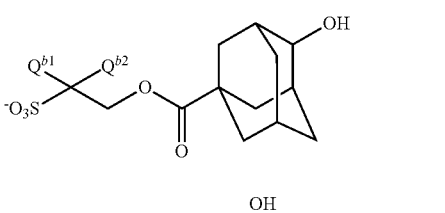 (I-A-37)
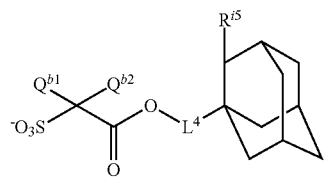 (B1-A-32)
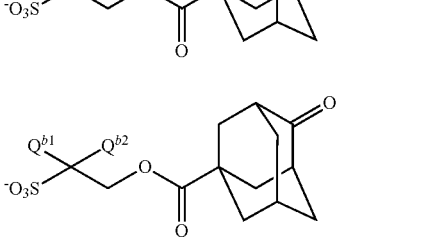 (I-A-38)
(I-A-39)

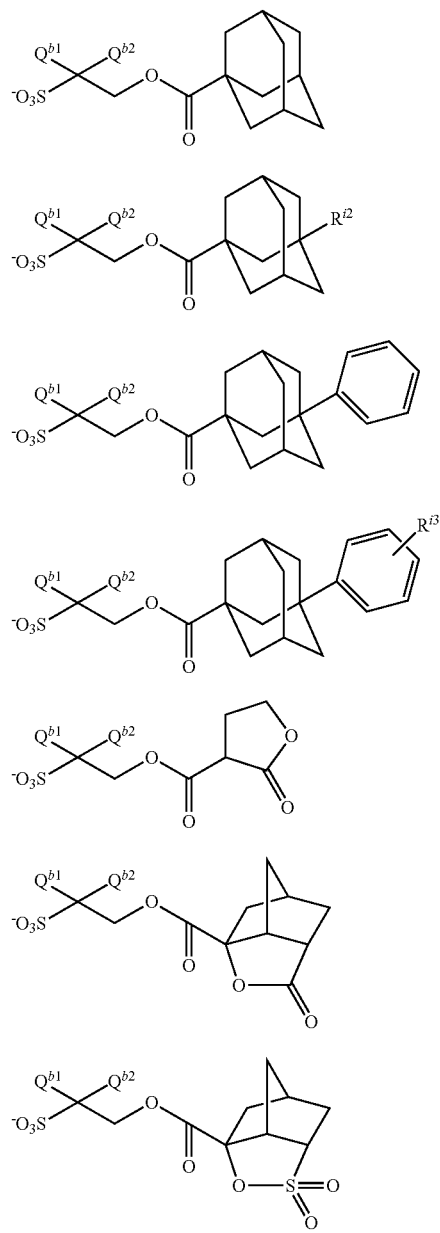

In formula (B1-A-1) to formula (B1-A-46), $R^{i2}$ to $R^{i7}$ independently represent a $C_1$ to $C_4$ alkyl group, and preferably a methyl group or an ethyl group. $R^{i8}$ represent a $C_1$ to $C_{12}$ aliphatic hydrocarbon group, preferably a $C_1$ to $C_4$ alkyl group, a $C_5$ to $C_{12}$ monovalent alicyclic hydrocarbon group or a group formed by a combination thereof, more preferably a methyl group, an ethyl group, a cyclohexyl group or an adamantyl group. $L^4$ represents a single bond or a $C_1$ to $C_4$ alkanediyl group. $Q^{b1}$ and $Q^{b2}$ represent the same meaning as defined above.

Specific examples of the sulfonic acid anion in the salt represented by formula (B1) include anions mentioned in JP2010-204646A1.

Among them, preferred examples of the sulfonic acid anion for the salt represented by formula (B1) include anions represented by formulae (B1a-1) to (B1a-22).

(B1a-10) 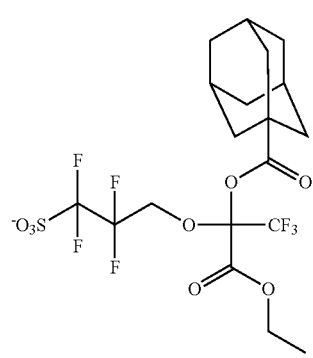
(B1a-11) 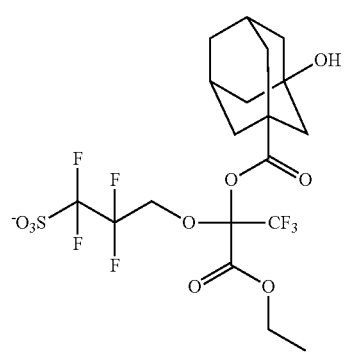
(B1a-12) 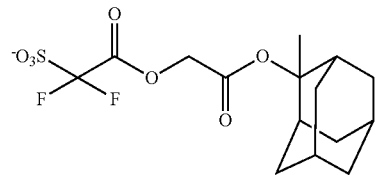
(B1a-13) 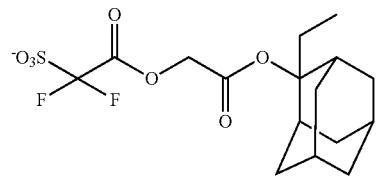
(B1a-14) 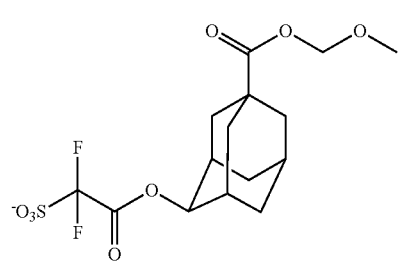
(B1a-15) 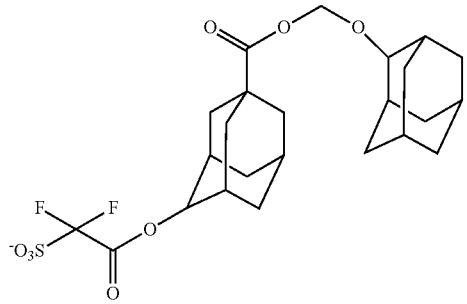
(B1a-16) 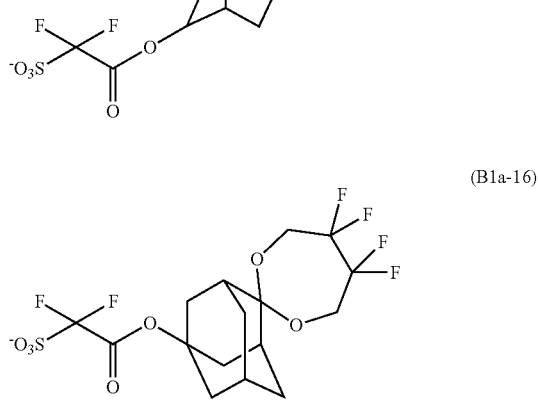
(B1a-17) 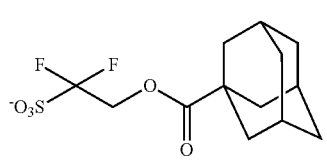
(B1a-18) 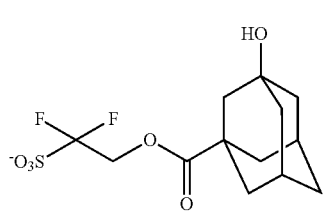
(B1a-19) 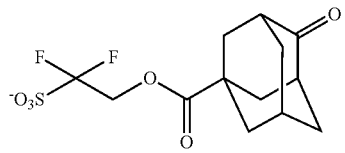
(B1a-20) 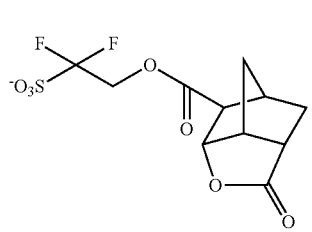
(B1a-21) 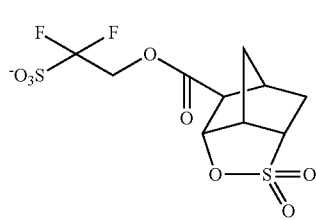

(B1a-22)

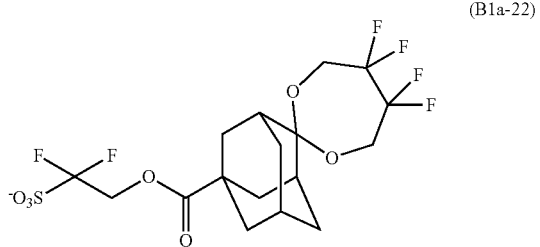

Among them, preferred examples of the sulfonic acid anion include anions represented by formulae (B1a-1) to (B1a-3), (B1a-7) to (B1a-16), (B1a-18), (B1a-19) and (B1a-22).

Examples of the organic cation represented by $Z^+$ include an organic onium cation such as an organic sulfonium cation, an organic iodonium cation, an organic ammonium cation, a benzothiazolium cation and an organic phosphonium cation, and an organic sulfonium cation and an organic iodonium cation are preferred, and an arylsulfonium cation is more preferred.

$Z^+$ of formula (B1) is preferably represented by any of the formulae (b2-1) to (b2-4) described above.

The acid generator (B1) is a combination of the above sulfonic acid anion and an organic cation. These anions and cations can be optionally combined with each other.

Preferred acid generator (B1) is a combination of any of the anion represented by formulae (B1a-1) to (B1a-3), formulae (B1a-7) to (B1a-16) and the cation represented by the formulae (b2-1) or (b2-3).

Preferred acid generators (B1) are represented by formulae (B1-1) to (B1-32). Among them, the formulae (B1-1), (B1-2), (B1-3), (B1-5), (B1-6), (B1-7), (B1-11), (B1-12), (B1-13), (B1-14), (B1-17), (B1-20), (B1-21), (B1-23), (B1-24), (B1-25), (B1-26), (B1-29), (B1-31) and (B1-32) which contain arylsulfonium cation are preferred.

(B1-1)

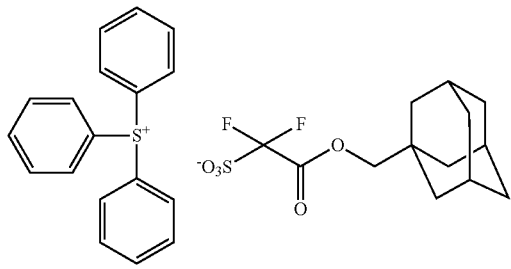

(B1-2)

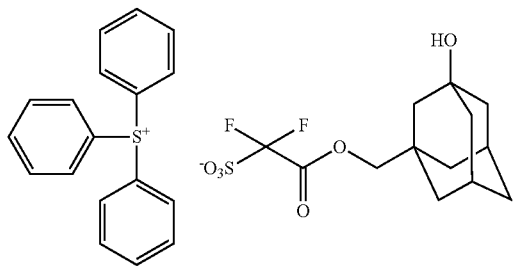

(B1-3)

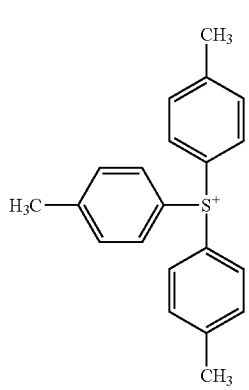

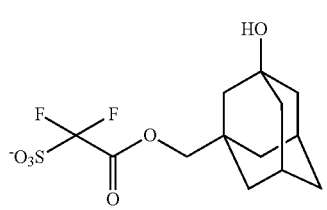

(B1-4)

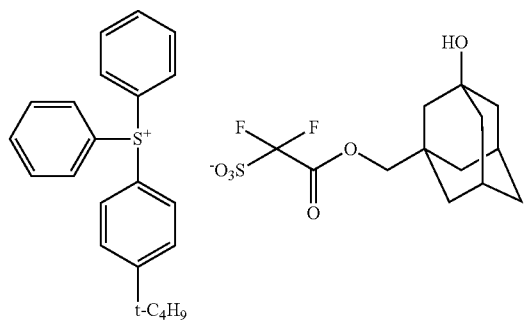

(B1-5)

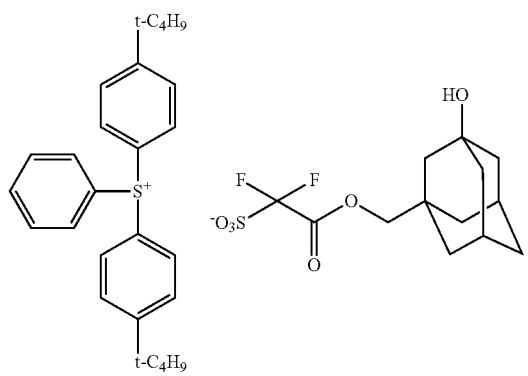

(B1-6)

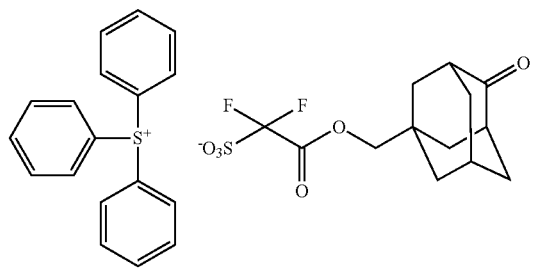

(B1-7)
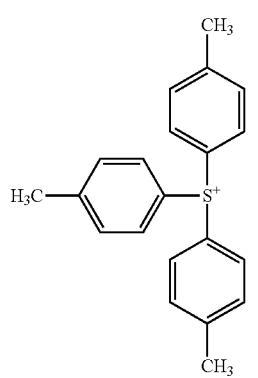
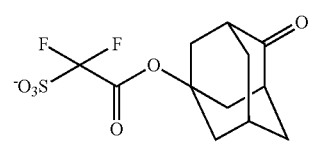
(B1-8)
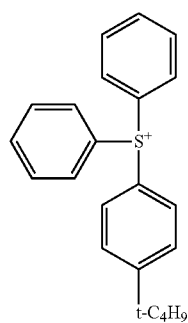
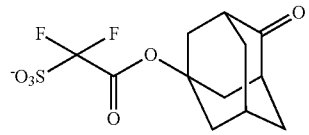
(B1-9)
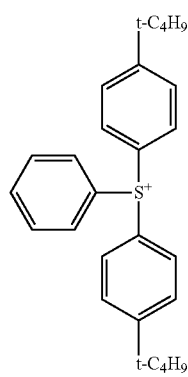
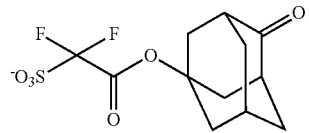
(B1-10)
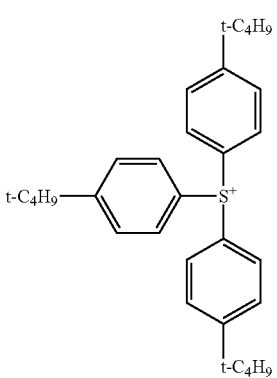
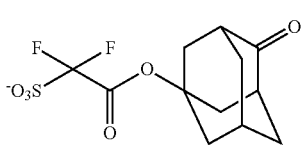
(B1-11)
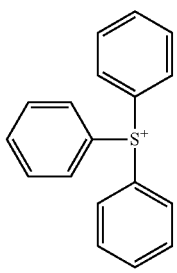
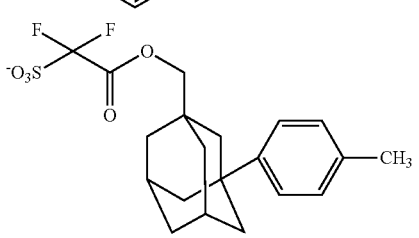
(B1-12)
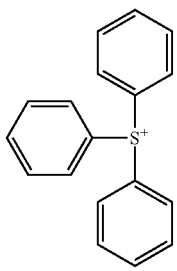 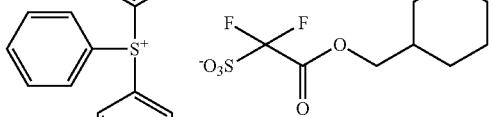
(B1-13)
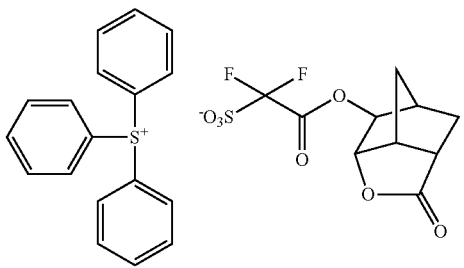

(B1-14) 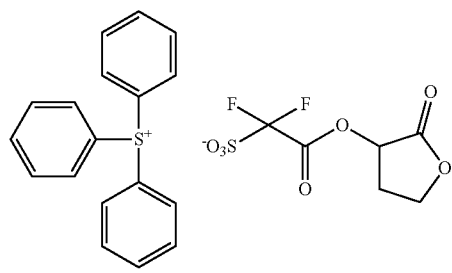
(B1-15) 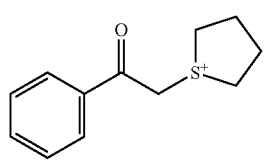
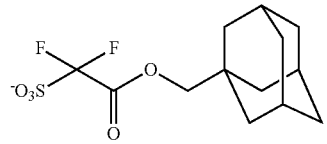
(B1-16) 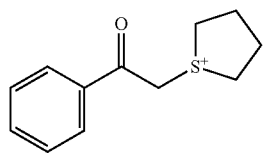
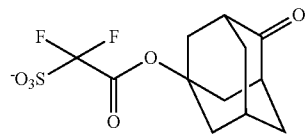
(B1-17) 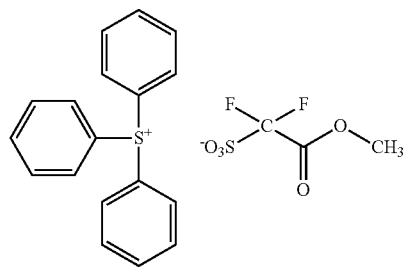
(B1-18) 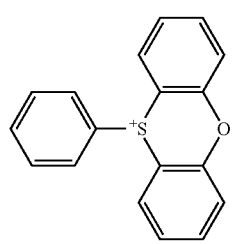
(B1-19) 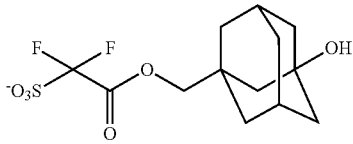
(B1-20) 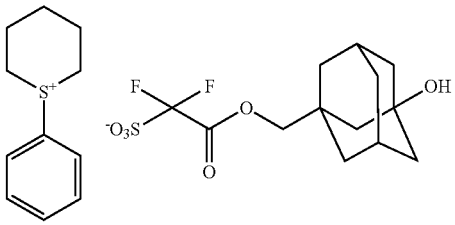
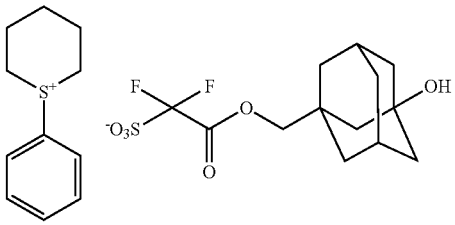
(B1-21) 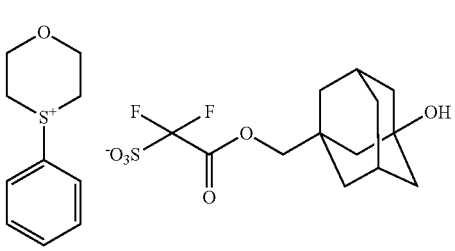
(B1-22) 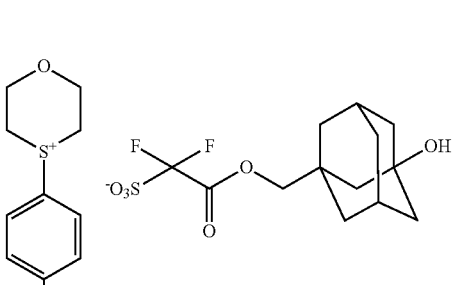
(B1-23) 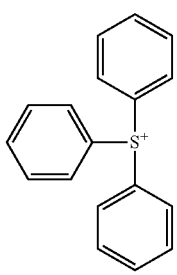

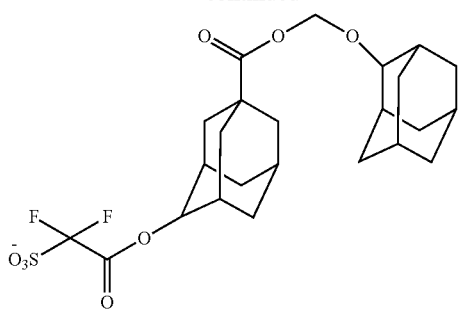
(B1-24)
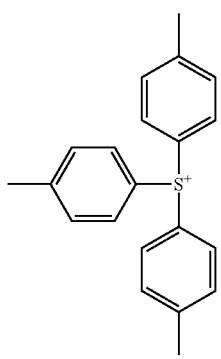
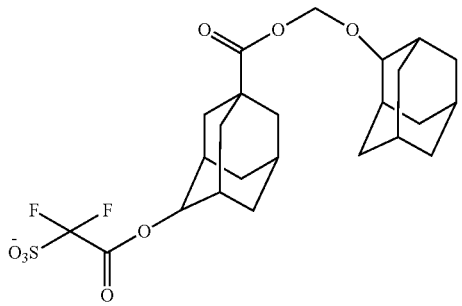
(B1-25)
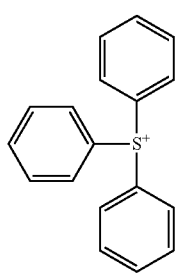
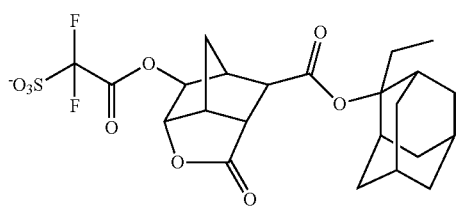
(B1-26)
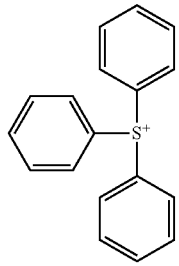
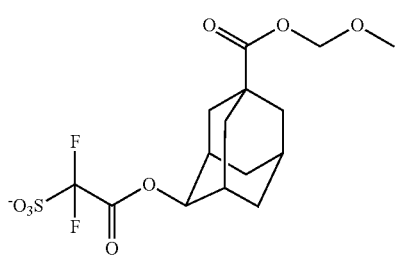
(B1-27)
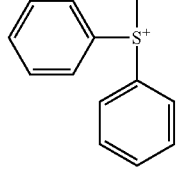
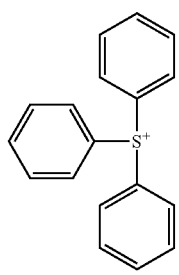
(B1-28)
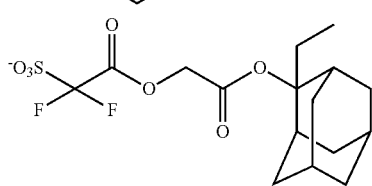

(B1-29)

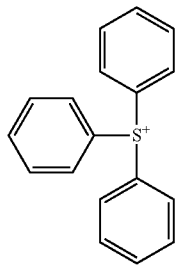

(B1-30)

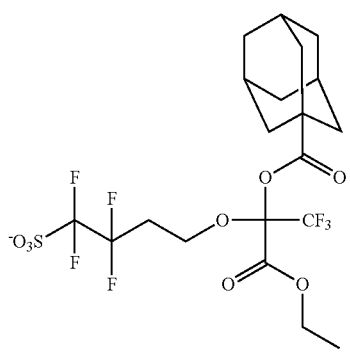

(B1-31)

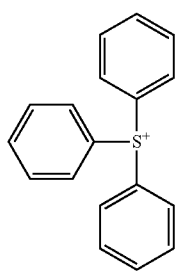

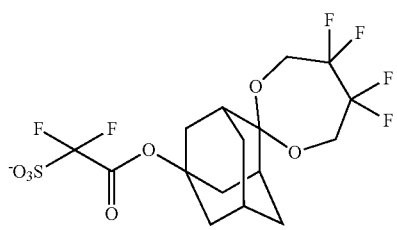

(B1-32)

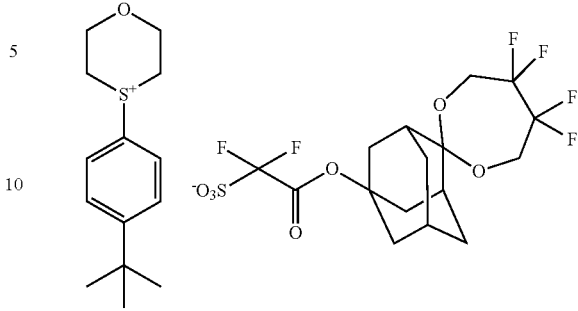

The acid generator (B) can be used as one kind of the salt or as two or more kinds of them.

The content of the acid generator (B) is preferably 1 to 30% by mass, preferably 3 to 25% by mass with respect to 100 parts by mass of the resin having an acid-labile group.

When both the salt (I) and the acid generator (B) are used as the acid generator in the resist composition of the present disclosure, the total content of the salt (I) and the acid generator (B) is preferably 1 parts by mass or more, and more preferably 3 parts by mass or more, and preferably 40 parts by mass or less, and more preferably 30 parts by mass or less, with respect to 100 parts by mass of the resin having an acid-labile group.

<Solvent (E)>

The proportion of a solvent (E) is 90% by mass or more, preferably 92% by mass or more, and more preferably 94% by mass or more, and also preferably 99% by mass or less and more preferably 99.9% by mass or less of the total amount of the resist composition. The proportion of the solvent (E) can be measured with a known analytical method such as, for example, liquid chromatography and gas chromatography.

Examples of the solvent (E) include glycol ether esters such as ethylcellosolve acetate, methylcellosolve acetate and propylene glycol monomethyl ether acetate; glycol ethers such as propylene glycol monomethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. These solvents may be used as a single solvent or as a mixture of two or more solvents.

<Quencher>

The resist composition of the present disclosure may contain a quencher such as a basic nitrogen-containing organic compound and a salt which generates an acid lower in acidity than an acid generated from the acid generators and which is sometimes referred to as "weak acid salt".

The proportion of the quencher is preferably 0.01% by mass to 5% by mass with respect to the total amount of solid components of the resist composition.

Examples of the basic nitrogen-containing organic compound include an amine and ammonium salts. The amine may be an aliphatic amine or an aromatic amine. The aliphatic amine includes any of a primary amine, secondary amine and tertiary amine.

Specific examples of the amine include 1-naphtylamine, 2-naphtylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylaminc, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylene diamine, tetramethylene diamine, hexamethylene diamine, 4,4'-diamino-1,2-diphenylethane, 4,4'-diamino-3,3'-dimethyldiphenylmethane, 4,4'-diamino-3,3'-diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine and bipyridine. Among them, diisopropylaniline is preferred, particularly 2,6-diisopropylaniline is more preferred.

Specific examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethyl ammonium hydroxide, 3-(trifluoromethyl)phenyltrimethylammonium hydroxide, tetra-n-butyl ammonium salicylate and choline.

The "acidity" for the weak acid salt can be represented by acid dissociation constant, pKa, of an acid generated from a weak acid salt. Examples of the weak acid salt include a salt generating an acid of pKa represents generally more than −3, preferably −1 to 7, and more preferably 0 to 5.

Specific examples of the weak acid salt include the following salts, the weak acid inner salt of formula (D), and salts as disclosed in JP2012-229206A, JP2012-6908A1, JP2012-72109A1, JP2011-39502A1 and JP2011-191745A1, preferably the salt of formula (D).

(D)

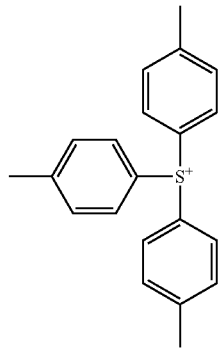

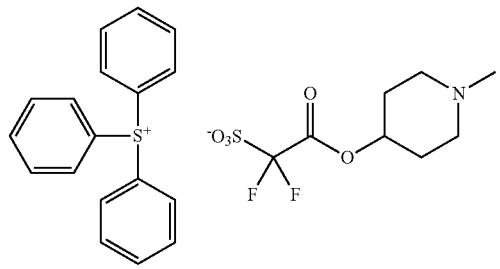

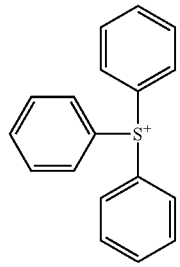

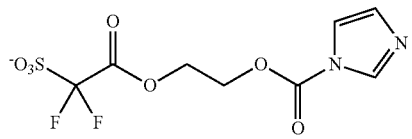

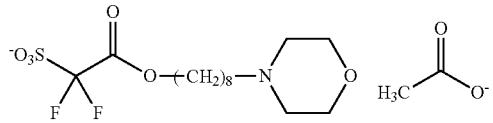

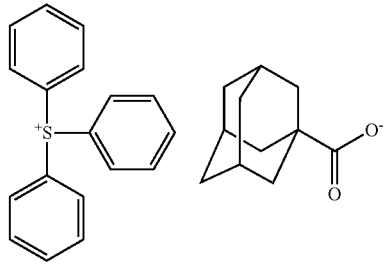

-continued

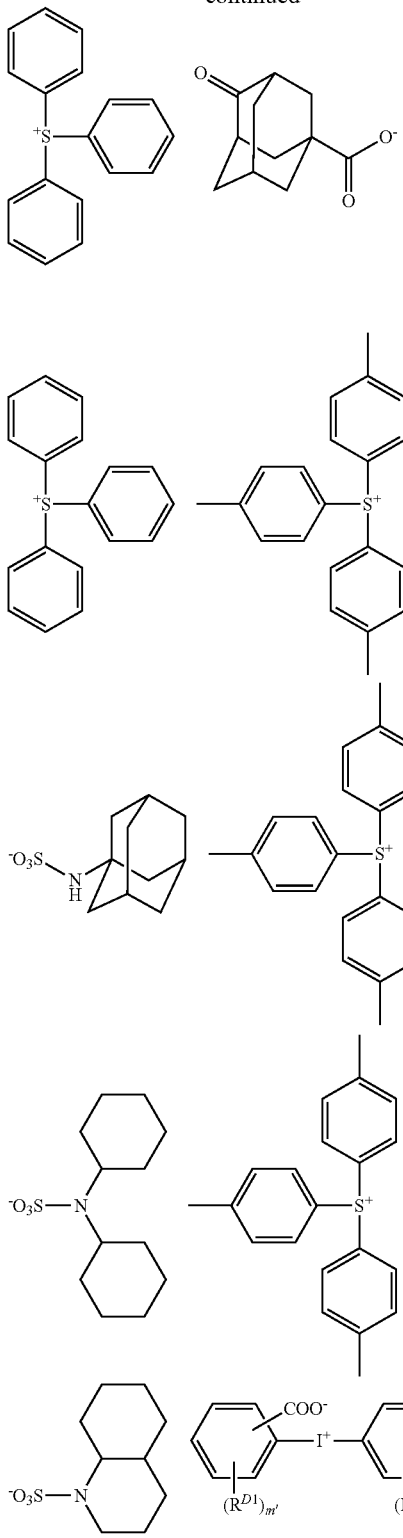

wherein $R^{D1}$ and $R^{D2}$ in each occurrence independently represent a $C_1$ to $C_{12}$ hydrocarbon group, a $C_1$ to $C_6$ alkoxy group, a $C_2$ to $C_7$ acyl group, a $C_2$ to $C_7$ acyloxy group, a $C_2$ to $C_7$ alkoxycarbonyl group, a nitro group or a halogen atom, and m' and n' independently represent an integer of 0 to 4.

The hydrocarbon group for $R^{D1}$ and $R^{D2}$ includes any of an aliphatic hydrocarbon group, an alicyclic hydrocarbon group, an aromatic hydrocarbon group and a combination thereof.

Examples of the aliphatic hydrocarbon group include an alkyl group such as methyl, ethyl, propyl, isopropyl, butyl, sec-butyl, tert-butyl, pentyl, hexyl and nonyl groups.

The alicyclic hydrocarbon group is any one of monocyclic or polycyclic hydrocarbon group, and saturated or unsaturated hydrocarbon group. Examples thereof include a cycloalkyl group such as cyclopropyl, cyclobutyl, cyclopentyl, cyclohexyl, cyclononyl and cyclododecyl groups; adamantyl and norbornyl groups. The alicyclic hydrocarbon group is preferably saturated hydrocarbon group.

Examples of the aromatic hydrocarbon group include an aryl group such as phenyl, 1-naphthyl, 2-naphthyl, 2-methylphenyl, 3-methylphenyl, 4-methylphenyl, 4-ethylphenyl, 4-propylphenyl, 4-isopropylphenyl, 4-butylphenyl, 4-tert-butylphenyl, 4-hexylphenyl, 4-cyclohexylphenyl, anthryl, p-adamantylphenyl, tolyl, xylyl, cumenyl, mesityl, biphenyl, phenanthryl, 2,6-diethylphenyl and 2-methyl-6-ethylphenyl groups.

Examples of the combination thereof include an alkyl-cycloalkyl, a cycloalkyl-alkyl, aralkyl (e.g., phenylmethyl, 1-phenylethyl, 2-phenylethyl, 1-phenyl-1-propyl, 1-phenyl-2-propyl, 2-phenyl-2-propyl, 3-phenyl-1-propyl, 4-phenyl-1-butyl, 5-phenyl-1-pentyl and 6-phenyl-1-hexyl groups) groups.

Examples of the alkoxy group include methoxy and ethoxy groups.

Examples of the acyl group include acetyl, propanonyl, benzoyl and cyclohexanecarbonyl groups.

Examples of the acyloxy group include a group in which oxy group (—O—) bonds to an acyl group.

Examples of the alkoxycarbonyl group include a group in which the carbonyl group (—CO—) bonds to the alkoxy group.

Examples of the halogen atom include a chlorine atom, a fluorine atom and bromine atom.

In the formula (D), $R^{D1}$ and $R^{D2}$ in each occurrence independently preferably represent a $C_1$ to $C_8$ alkyl group, a $C_3$ to $C_{10}$ cycloalkyl group, a $C_1$ to $C_6$ alkoxy group, a $C_2$ to $C_4$ acyl group, a $C_2$ to $C_4$ acyloxy group, a $C_2$ to $C_4$ alkoxycarbonyl group, a nitro group or a halogen atom.

m' and n' independently preferably represent an integer of 0 to 3, more preferably an integer of 0 to 2, and more preferably 0.

Specific examples of the weak acid inner salt include the following ones.

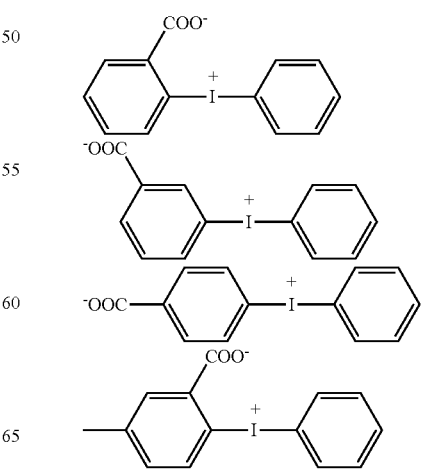

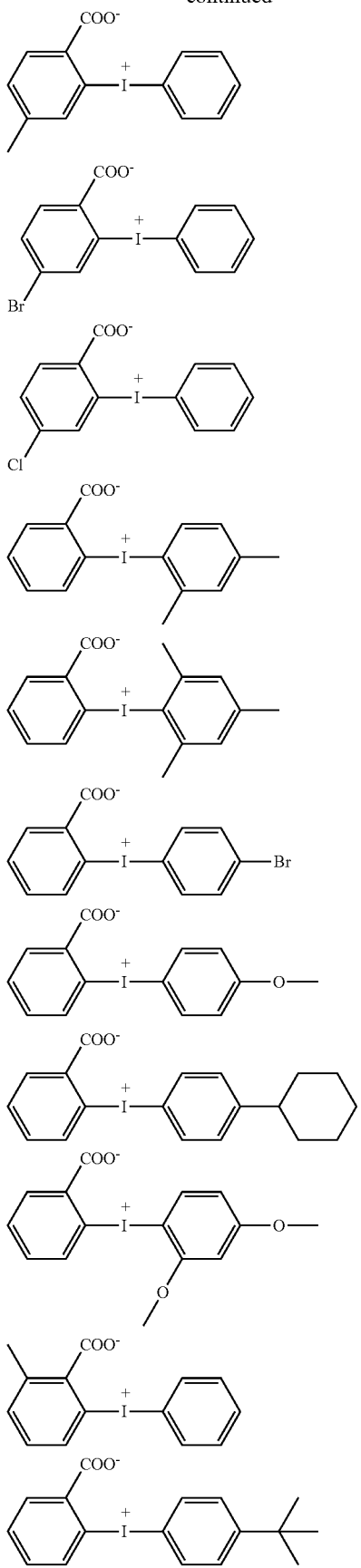
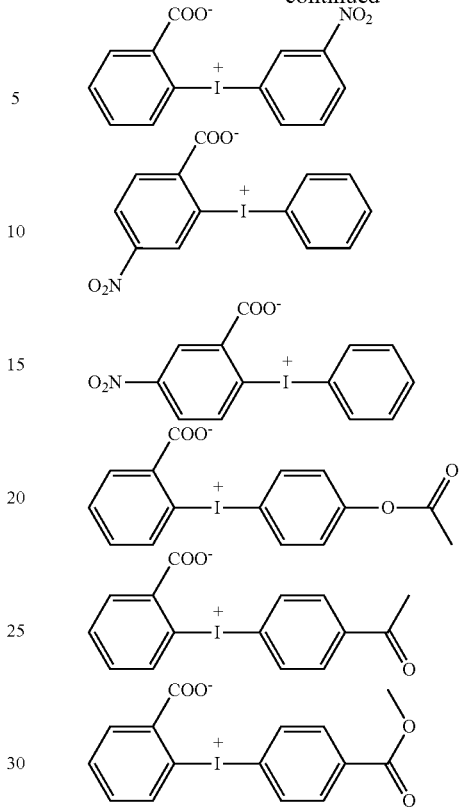

The weak acid inner salt of formula (D) can be produced by a method described in "Tetrahedron Vol. 45, No. 19, p 6281-6296". Also, commercially available compounds can be used as the compound (D).

In the resist composition of the present disclosure, the proportion of the salt which generates an acid weaker in acidity than an acid generated from the acid generator, for example, the weak acid inner salt (D) is preferably 0.01% by mass to 5% by mass, more preferably 0.01% by mass to 4% by mass, and still more preferably 0.01% by mass to 3% by mass with respect to total amount of solid components of the resist composition.

<Other Ingredient>

The resist composition can also include other ingredient (which is sometimes referred to as "other ingredient (F)"). The other ingredient (F) includes various additives such as sensitizers, dissolution inhibitors, surfactants, stabilizers, and dyes, as needed.

<Preparing the Resist Composition>

The present resist composition can be prepared by mixing at least one of the resin (A) and salt (I) as well as the other resin, acid generator (B), the quencher, the weak acid inner salt (D), the solvent (E) and the other ingredient (F), as needed. There is no particular limitation on the order of mixing. The mixing may be performed in an arbitrary order. The temperature of mixing may be adjusted to an appropriate temperature within the range of 10 to 40° C., depending on the kinds of the resin and solubility in the solvent (E) of the resin. The time of mixing may be adjusted to an appropriate time within the range of 0.5 to 24 hours, depending on the mixing temperature. There is no particular limitation to the tool for mixing. An agitation mixing may be adopted.

After mixing the above ingredients, the present resist compositions can be prepared by filtering the mixture through a filter having about 0.003 to 0.2 µm of its pore diameter.

<Method for Producing Resist Pattern>

The method for producing a resist pattern of the present disclosure includes the steps of:

(1) applying the resist composition of the present disclosure onto a substrate;

(2) drying the applied composition to form a composition layer;

(3) exposing the composition layer;

(4) heating the exposed composition layer, and (5) developing the heated composition layer.

Applying the resist composition onto the substrate can generally be carried out through the use of a resist application device, such as a spin coater known in the field of semiconductor microfabrication technique. Examples of the substrate include inorganic substrates such as silicon wafer. The substrate may be washed, and an organic antireflection film may be formed on the substrate by use of a commercially available antireflection composition, before the application of the resist composition.

The solvent evaporates from the resist composition to form a composition layer. Drying the composition on a substrate, for example, can be carried out using a heating device such as a hotplate (so-called "prebake"), a decompression device, or a combination thereof. The temperature is preferably within the range of 50 to 200° C. The time for heating is preferably 10 to 180 seconds. The pressure is preferably within the range of 1 to $1.0 \times 10^5$ Pa.

The composition layer thus obtained is generally exposed using an exposure apparatus or a liquid immersion exposure apparatus. The exposure is generally carried out using with various types of exposure light source, such as irradiation with ultraviolet lasers, i.e., KrF excimer laser (wavelength: 248 nm), ArF excimer laser (wavelength: 193 nm), $F_2$ excimer laser (wavelength: 157 nm), irradiation with harmonic laser light of far-ultraviolet or vacuum ultra violet wavelength-converted laser light from a solid-state laser source (YAG or semiconductor laser or the like), or irradiation with electron beam or EUV or the like. In the specification, such exposure to radiation is sometimes referred to be collectively called as exposure. The exposure is generally carried out through a mask that corresponds to the desired pattern. When electron beam is used as the exposure light source, direct writing without using a mask can be carried out.

After exposure, the composition layer is subjected to a heat treatment (so-called "post-exposure bake") to promote the deprotection reaction. The heat treatment can be carried out using a heating device such as a hotplate. The heating temperature is generally in the range of 50 to 200° C., preferably in the range of 70 to 150° C.

The developing of the baked composition film is usually carried out with a developer using a development apparatus. Developing can be conducted in the manner of dipping method, paddle method, spray method and dynamic dispensing method. Temperature for developing is generally 5 to 60° C. The time for developing is preferably 5 to 300 seconds.

The photoresist pattern obtained from the photoresist composition may be a positive one or a negative one by selecting suitable developer.

The development for obtaining a positive photoresist pattern is usually carried out with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The surfactant may be contained in the alkaline developer.

After development, the resist pattern formed is preferably washed with ultrapure water, and the residual water remained on the resist film or on the substrate is preferably removed therefrom.

The development for obtaining a negative photoresist pattern is usually carried out with a developer containing an organic solvent. The organic solvent to be used may be any one of various organic solvents used in the art, examples of which include ketone solvents such as 2-hexanone, 2-heptanone; glycol ether ester solvents such as propylene glycol monomethyl ether acetate; ester solvents such as the butyl acetate; glycol ether solvents such as the propylene glycol monomethyl ether; amide solvents such as N,N-dimethylacetamide; aromatic hydrocarbon solvents such as anisole.

In the developer containing an organic solvent, the amount of organic solvents is preferably 90% by mass to 100% by mass, more preferably 95% by mass to 100% by mass of the developer. The developer still more preferably consists essentially of organic solvents.

Among them, the developer containing an organic solvent preferably contains butyl acetate and/or 2-heptanone. In the developer containing an organic solvent, the total amount of butyl acetate and 2-heptanone is preferably 50% by mass to 100% by mass of the developer, more preferably 90% by mass to 100% by mass of the developer. The developer still more preferably consists essentially of butyl acetate and/or 2-heptanone.

Developers containing an organic solvent may contain a surfactant. Also, the developer containing an organic solvent may include a little water.

The developing with a developer containing an organic solvent can be finished by replacing the developer by another solvent.

After development, the photoresist pattern formed is preferably washed with a rinse agent. Such rinse agent is not unlimited provided that it does not detract a photoresist pattern. Examples of the agent include solvents which contain organic solvents other than the above-mentioned developers, such as alcohol agents or ester agents.

After washing, the residual rinse agent remained on the substrate or photoresist film is preferably removed therefrom.

<Application>

The resist composition of the present disclosure is useful for excimer laser lithography such as with ArF, KrF, electron beam (EB) exposure lithography or extreme-ultraviolet (EUV) exposure lithography, and is more useful for electron beam (EB) exposure lithography, ArF excimer laser exposure lithography and extreme-ultraviolet (EUV) exposure lithography.

The resist composition of the present disclosure can be used in semiconductor microfabrication.

EXAMPLES

All percentages and parts expressing the contents or amounts used in the Examples and Comparative Examples are based on mass, unless otherwise specified.

The weight average molecular weight is a value determined by gel permeation chromatography.

Column: TSK gel Multipore HXL-M×3+guardcolumn (Tosoh Co. Ltd.)

Eluant: tetrahydrofuran
Flow rate: 1.0 mL/min
Detecting device: RI detector
Column temperature: 40° C.
Injection amount: 100 μL
Standard material for calculating molecular weight: standard polystyrene (Tosoh Co. ltd.)

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). The value of the peak in the mass spectrometry is referred to as "MASS".

Example 1

Synthesis of the Salt Represented by Formula (I-1)

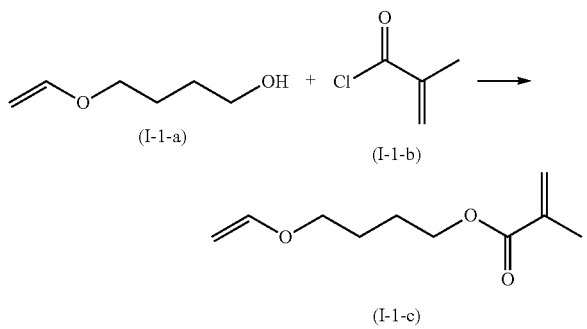

In to a reactor, 5.00 parts of the compound represented by formula (I-1-a), 10 parts of tetrahydrofuran and 4.79 parts of triethylamine were charged and stirred at 23° C. for 30 minutes. The obtained mixture was cooled into 0° C. Then, 4.50 parts of the compound represented by formula (I-1-b) was dropped thereto over 30 minutes at 0° C., and the obtained mixture was stirred for 1 hour at 0° C. 150 parts of ethyl acetate, 50 parts of ion exchanged water and 50 parts of a saturated aqueous ammonium chloride solution were added to the resulting reactant, the obtained mixture was stirred at 23° C. for 30 minutes, and left still to separate an organic layer. To the obtained organic layer, 100 parts of ion exchanged water was added, stirred at 23° C. for 30 minutes, and left still, followed by separating an organic layer to wash with water. The washing step was conducted five times. The obtained organic layer was concentrated and purified with column chromatography [silica gel 60N spherical shape, neutral, 100-210 μm, solvent: mixture of n-heptane/ethyl acetate=10/1, manufactured by Kanto Chem. Ltd.] to provide 3.30 parts of the compound represented by formula (I-1-c).

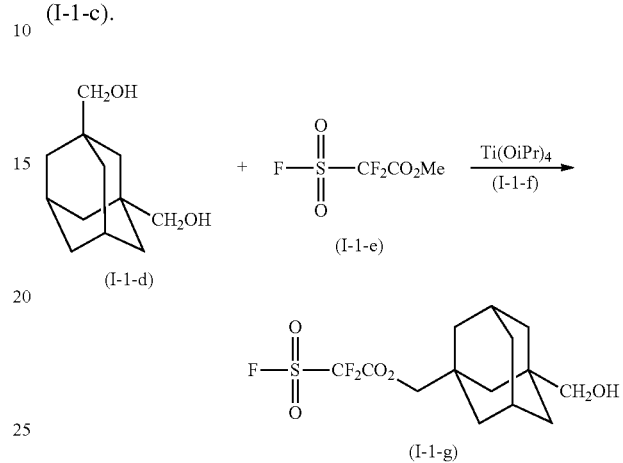

In to a reactor, 5.72 parts of the compound represented by formula (I-1-d), 4.00 parts of the compound represented by formula (I-1-e), 0.26 parts of the compound represented by formula (I-1-f) and 60 parts of chloroform were charged and stirred at 23° C. for 30 minutes. The obtained mixture solution was dehydrated while being stirred at 80° C. for 10 hours, and then cooled into 23° C. To the obtained reactant, 200 parts of chloroform, 125 parts of ion exchanged water and 40 parts of saturated sodium chloride were added, the obtained mixture was stirred at 23° C. for 30 minutes, and left still to separate an organic layer. To the obtained organic layer, 100 parts of ion exchanged water was added, stirred at 23° C. for 30 minutes, and left still, followed by separating an organic layer to wash with water. The washing step was conducted five times. The obtained organic layer was concentrated to provide 5.54 parts of the compound represented by formula (I-1-g).

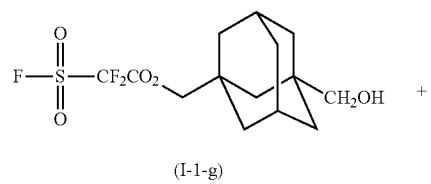

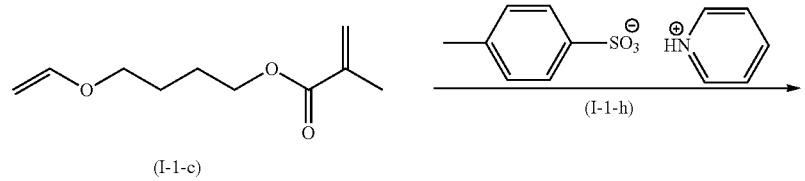

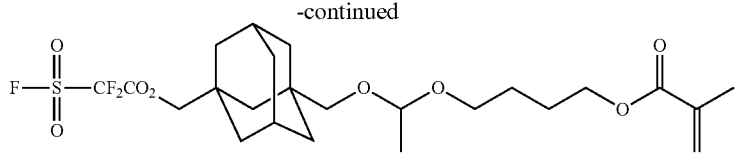

(I-1-i)

In to a reactor, 1.59 parts of the salt represented by formula (I-1-g), 1.21 parts of the compound represented by formula (I-1-c), 0.01 parts of the salt represented by formula (I-1-h) and 25 parts of tetrahydrofuran were charged and stirred at 23° C. for 30 minutes, and further stirred at 23° C. for 18 hours. Then, 200 parts of ethyl acetate, 50 parts of ion exchanged water and 5 parts of a saturated aqueous ammonium chloride solution were added to the resulting reactant, the obtained mixture was stirred at 23° C. for 30 minutes, and left still to separate an organic layer. To the obtained organic layer, 100 parts of ion exchanged water was added, stirred at 23° C. for 30 minutes, and left still, followed by separating an organic layer to wash with water. The washing step was conducted twice. The obtained organic layer was concentrated, to provide 1.43 parts of the compound represented by formula (I-1-i).

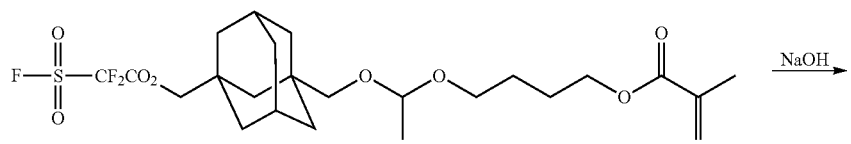

(I-1-i)

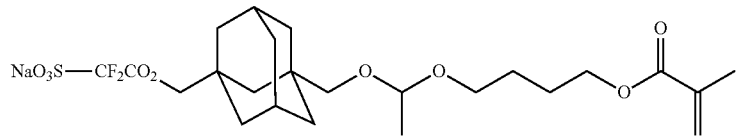

(I-1-j)

In to a reactor, 1.41 parts of the compound represented by formula (I-1-i), 30 parts of ion exchanged water and 30 parts of acetonitrile were charged, the obtained mixture was stirred at 23° C. for 30 minutes, and then cooled into 0° C. Then, a solution containing 0.34 parts of sodium hydrate and 30 parts of ion exchanged was dropped into the obtained mixture over 1 hour, and stirred at 0° C. for about 3 hours. 0.04 parts of concentrated hydrochloric acid was added to the obtained reaction mixture and stirred at 23° C. for 30 minutes to provide the salt represented by formula (I-1-j).

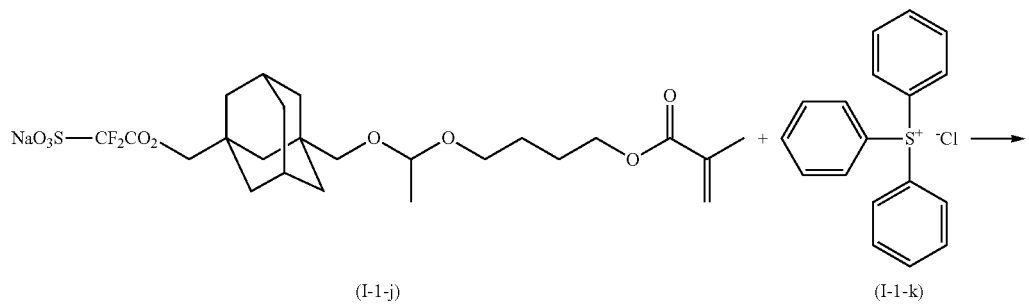

(I-1-j)　　　　　　　　(I-1-k)

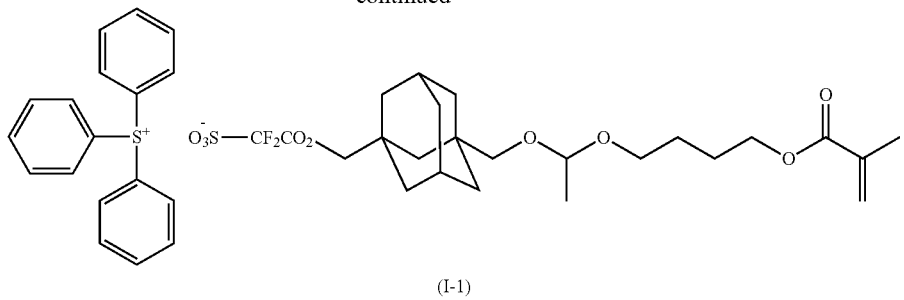

(I-1)

To the obtained reactant, 50 parts of chloroform and 0.78 parts of the salt represented by formula (I-1-k) were added and stirred at 23° C. for 4 hours, followed by being left still to separate an organic layer. To the obtained organic layer, 50 parts of ion exchanged water was added, stirred at 23° C. for 30 minutes, and left still, followed by separating an organic layer to wash with water. The washing step was conducted eight times. The obtained organic layer was concentrated, 20 parts of tert-butylmethylether was added to the obtained residue, stirred, followed by removing the supernatant solution therefrom. The obtained residue was concentrated and 20 parts of ethyl acetate was added thereto, followed by removing the supernatant solution therefrom. 20 parts of tert-butylmethylether was added to the obtained residue, followed by removing the supernatant solution therefrom. The obtained residue wad dissolved in acetonitrile, and the solution was concentrated, to provide 1.01 parts of the salt represented by formula (I-1).

MASS (ESI(+)Spectrum): M⁺ 263.1
MASS (ESI(−)Spectrum): M⁻ 537.2

Example 2

Synthesis of the Salt Represented by Formula (I-2)

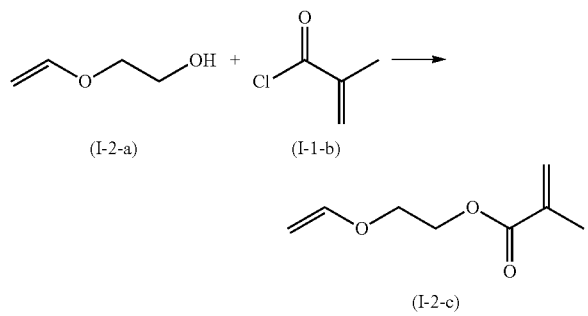

In to a reactor, 3.79 parts of the compound represented by formula (I-2-a), 10 parts of tetrahydrofuran and 4.79 parts of triethylamine were charged and stirred at 23° C. for 30 minutes. The obtained mixture was cooled into 0° C. Then, 4.50 parts of the compound represented by formula (I-1-b) was dropped thereto over 30 minutes at 0° C., and the obtained mixture was stirred for 1 hour at 0° C. 100 parts of ethyl acetate, 50 parts of ion exchanged water and 50 parts of a saturated aqueous ammonium chloride solution were added to the resulting reactant, the obtained mixture was stirred at 23° C. for 30 minutes, and left still to separate an organic layer. To the obtained organic layer, 100 parts of ion exchanged water was added, stirred at 23° C. for 30 minutes, and left still, followed by separating an organic layer to wash with water. The washing step was conducted five times. The obtained organic layer was concentrated and purified with column chromatography [silica gel 60N spherical shape, neutral, 100-210 μm, solvent: mixture of n-heptane/ethyl acetate=5/1, manufactured by Kanto Chem. Ltd.], to provide 3.12 parts of the compound represented by formula (I-2-c).

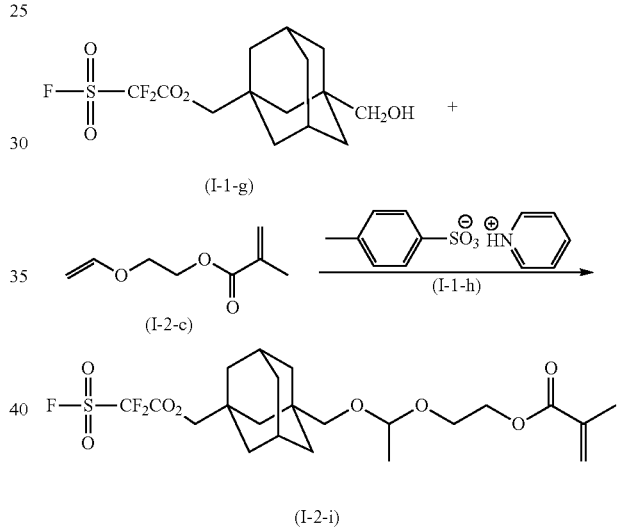

In to a reactor, 1.59 parts of the compound represented by formula (I-1-g), 1.03 parts of the compound represented by formula (I-2-c), 0.01 parts of the compound represented by formula (I-1-h) and 25 parts of tetrahydrofuran were charged and stirred at 23° C. for 30 minutes, and further stirred at 23° C. for about 18 hours. Then, 200 parts of ethyl acetate, 50 parts of ion exchanged water and 5 parts of a saturated aqueous sodium bicarbonate solution were added to the resulting reactant, the obtained mixture was stirred at 23° C. for 30 minutes, followed by being left still to separate an organic layer. To the obtained organic layer, 100 parts of ion exchanged water was added and stirred at 23° C. for 30 minutes, and then left still, followed by separating an organic layer to wash with water. The washing step was conducted twice. The obtained organic layer was concentrated, to provide 1.46 parts of the compound represented by formula (I-2-i).

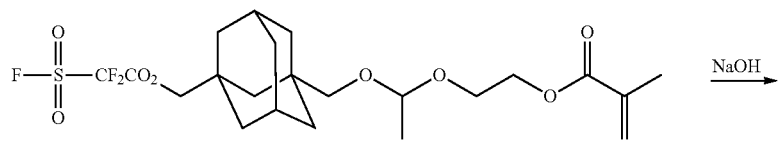

(I-2-i)

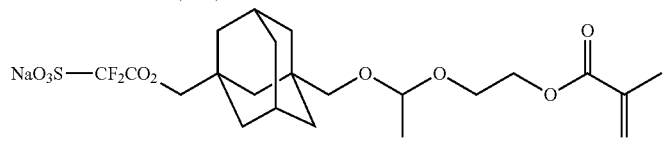

(I-2-j)

In to a reactor, 1.34 parts of the compound represented by formula (I-2-i), 30 parts of ion exchanged water and 30 parts of acetonitrile were charged, the obtained mixture was stirred at 23° C. for 30 minutes, and then cooled into 0° C. Then, a solution containing 0.34 parts of sodium hydrate and 30 parts of ion exchanged was dropped into the obtained mixture over 1 hour, and stirred at 0° C. for about 3 hours. 0.04 parts of concentrated hydrochloric acid was added thereto and stirred at 23° C. for 30 minutes, to provide the salt represented by formula (I-2-j).

for 30 minutes, and left still, followed by separating an organic layer to wash with water. The washing step was conducted eight times. The obtained organic layer was concentrated, 20 parts of tert-butylmethylether was added to the obtained residue, stirred, followed by removing the supernatant solution therefrom. The obtained residue was concentrated, 20 parts of ethyl acetate was added thereto, followed by removing the supernatant solution therefrom. 20 parts of tert-butylmethylether was added to the obtained residue, followed by removing the supernatant solution

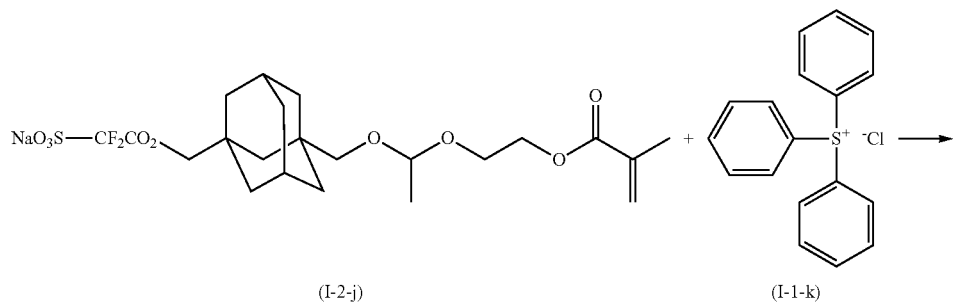

(I-2-j)    (I-1-k)

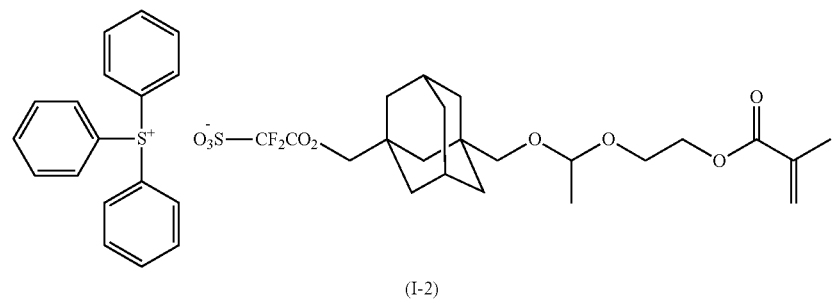

(I-2)

To the obtained reactant, 50 parts of chloroform and 0.78 parts of the salt represented by formula (I-1-k) were added and stirred at 23° C. for 4 hours, followed by being left still to separate an organic layer. To the obtained organic layer, 50 parts of ion exchanged water was added, stirred at 23° C.

therefrom. The obtained residue wad dissolved in acetonitrile, and the solution was concentrated, to provide 0.89 parts of the salt represented by formula (I-2).

MASS (ESI(+)Spectrum): $M^+$ 263.1
MASS (ESI(−)Spectrum): $M^-$ 509.2

Example 3

Synthesis of the Salt Represented by Formula (I-71)

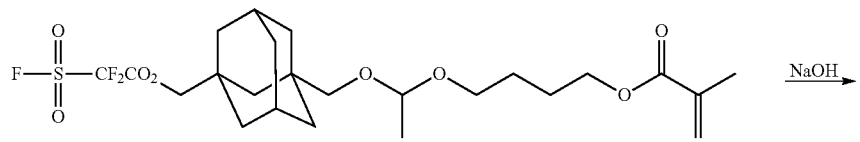

(I-1-i)

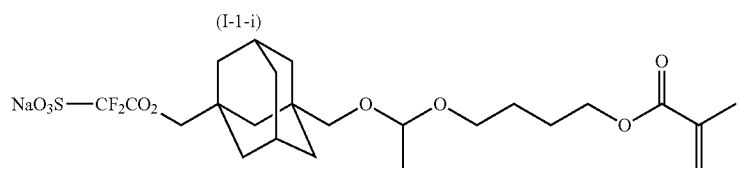

(I-1-j)

In to a reactor, 1.41 parts of the compound represented by formula (I-1-i), 30 parts of ion exchanged water and 30 parts of acetonitrile were charged, the obtained mixture was stirred at 23° C. for 30 minutes, and then cooled into 0° C. Then, a solution containing 0.34 parts of sodium hydrate and 30 parts of ion exchanged was dropped into the obtained mixture over 1 hour, and stirred at 0° C. for about 3 hours. 0.04 parts of concentrated hydrochloric acid was added thereto and stirred at 23° C. for 30 minutes, to provide the salt represented by formula (I-1-j).

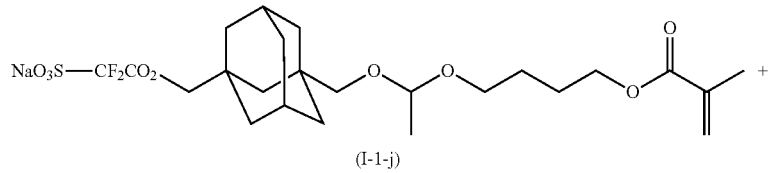

(I-1-j)

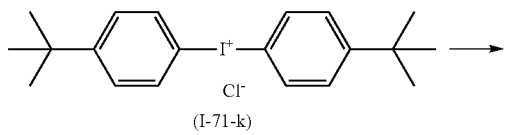

(I-71-k)

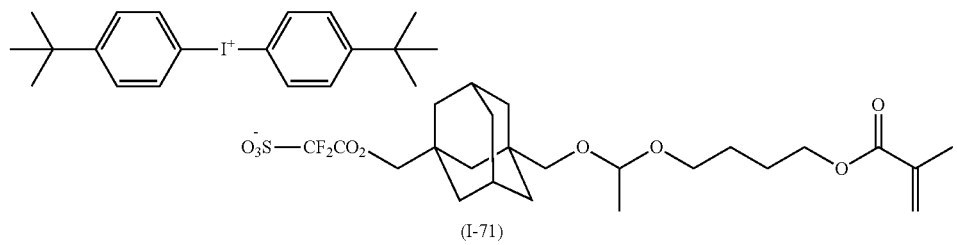

(I-71)

To the obtained reactant, 50 parts of chloroform and 1.12 parts of the salt represented by formula (I-71-k) were added and stirred at 23° C. for 4 hours, followed by being left still to separate an organic layer. To the obtained organic layer, 50 parts of ion exchanged water was added, stirred at 23° C. for 30 minutes, and left still, followed by separating an organic layer to wash with water. The washing step was conducted eight times. The obtained organic layer was concentrated, 20 parts of tert-butylmethylether was added to the obtained residue, stirred, followed by removing the supernatant solution therefrom. The obtained residue was concentrated, 20 parts of ethyl acetate was added thereto, followed by removing the supernatant solution therefrom. 20 parts of tert-butylmethylether was added to the obtained residue, followed by removing the supernatant solution therefrom. The obtained residue was dissolved in acetonitrile, and the solution was concentrated, to provide 1.48 parts of the salt represented by formula (I-71).

MASS (ESI(+)Spectrum): $M^+$ 393.1
MASS (ESI(−)Spectrum): $M^-$ 537.2

Example 4

Synthesis of the Salt Represented by Formula (I-57)

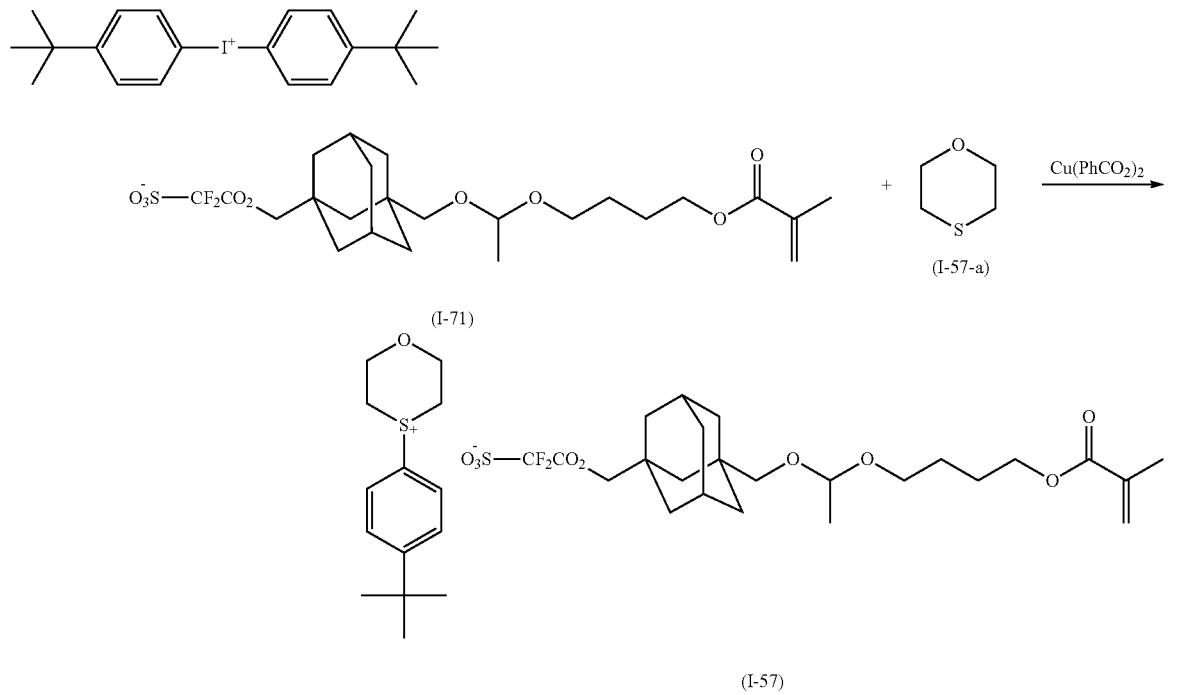

In to a reactor, 1.27 parts of the salt represented by formula (I-71), 0.14 parts of the compound represented by formula (I-57-a) and 20 parts of monochlorobenzene were charged, and stirred at 23° C. for 30 minutes. To the obtained mixture, 0.01 parts of copper (II) benzoate was added, and stirred at 100° C. for 1 hour. The obtained reacted solution was concentrated, 20 parts of chloroform and 10 parts of ion exchanged water were added to the obtained residue, and stirred at 23° C. for 30 minutes to separate an organic layer. To the obtained organic layer, 10 parts of ion exchanged water was added, stirred at 23° C. for 30 minutes, followed by separating an organic layer to wash with water. The washing step was conducted five times. The obtained organic layer was concentrated, 10 parts of tert-butylmethylether was added to the obtained residue, followed by removing the supernatant solution therefrom. The obtained residue was concentrated. The obtained residue wad dissolved in acetonitrile, and the solution was concentrated, to provide 0.71 parts of the salt represented by formula (I-57).

MASS (ESI(+)Spectrum): M⁺ 237.1
MASS (ESI(−)Spectrum): M⁻ 537.2

Synthesis Example 1

Synthesis of the Salt Represented by Formula (B1-21)

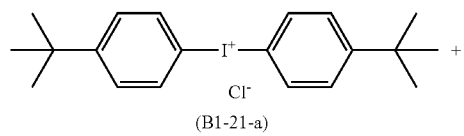

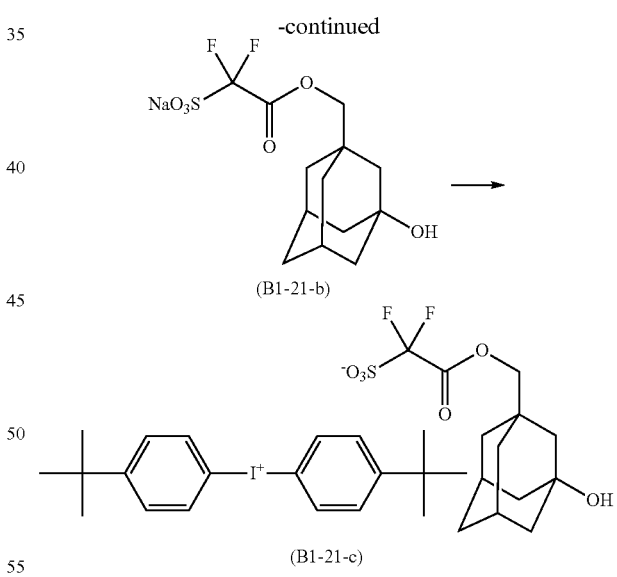

The compound represented by formula (B1-21-b) was produced according to a method recited in JP2008-209917A1.

In to a reactor, 30.00 parts of compound represented by formula (B1-21-b) and 35.50 parts of salt represented by formula (B1-21-a), 100 parts of chloroform and 50 parts of ion exchanged water were charged and stirred at 23° C. for about 15 hours. The obtained reaction mixture, which had two layers, was separated into a chloroform layer therefrom. To the chloroform layer, 30 parts of ion exchanged water was added and washed with it. These steps were conducted five times. Then the washed layer was concentrated, and then, 100 parts of tert-butylmethylether was added to the obtained residues and the obtained mixture was stirred at 23° C. for 30 minutes. The resulting mixture was filtrated, to provide 48.57 parts of salt represented by formula (B1-21-c).

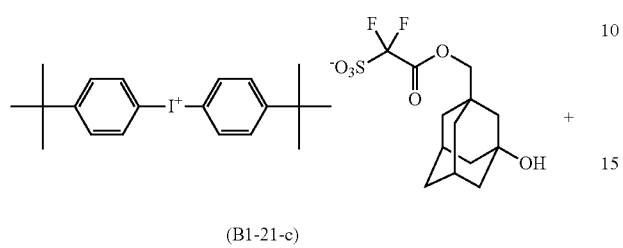

(B1-21-c)

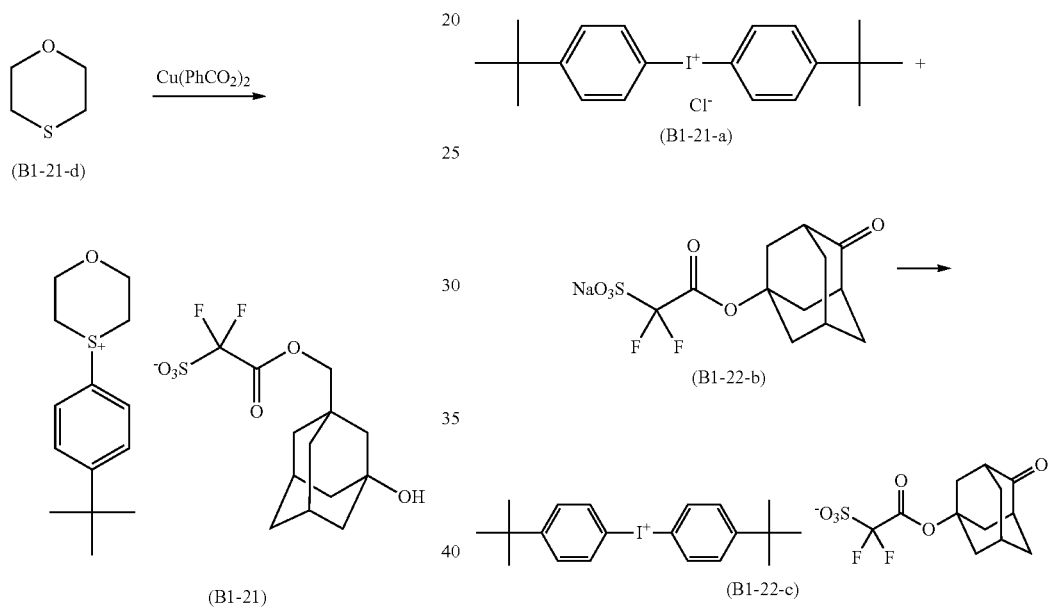

In to a reactor, 20.00 parts of salt represented by formula (B1-21-c), 2.84 parts of compound represented by formula (B1-21-d) and 250 parts of monochlorobenzene were charged and stirred at 23° C. for 30 minutes. To the resulting mixture, 0.21 parts of dibenzoic acid copper (II) was added and the obtained mixture was stirred at 100° C. for 1 hour. The reaction mixture was concentrated, and then, 200 parts of chloroform and 50 parts of ion exchanged water were added to the obtained residues and the obtained mixture was stirred at 23° C. for 30 minutes, followed by separating an organic layer to wash with water. The following washing step was conducted five times. 50 parts of ion exchanged water were added to the obtained organic layer, and the obtained mixture was stirred at 23° C. for 30 minutes, followed by separating an organic layer. The obtained organic layer was concentrated, and then the obtained residues were dissolved in 53.51 parts of acetonitrile. Then the mixture was concentrated, and then 113.05 parts of tert-butylmethylether was added thereto and the obtained mixture was stirred, followed by filtrating it, to provide 10.47 parts of salt represented by formula (B1-21).

MASS (ESI(+)Spectrum): M$^+$ 237.1

MASS (ESI(−)Spectrum): M$^-$ 339.1

Synthesis Example 2

Synthesis of the Salt Represented by Formula (B1-22)

In to a reactor, 11.26 parts of salt represented by formula (B1-21-a), 10.00 parts of compound represented by formula (B1-22-b), 50 parts of chloroform and 25 parts of ion exchanged water were charged and stirred at 23° C. for about 15 hours. The obtained reaction mixture, which had two layers, was separated into a chloroform layer therefrom. To the chloroform layer, 15 parts of ion exchanged water were added and washed with it: These steps were conducted five times. Then the washed layer was concentrated, and then, 50 parts of tert-butylmethylether was added to the obtained residues and the obtained mixture was stirred at 23° C. for 30 minutes. The resulting mixture was filtrated, to provide 11.75 parts of salt represented by formula (B1-22-c).

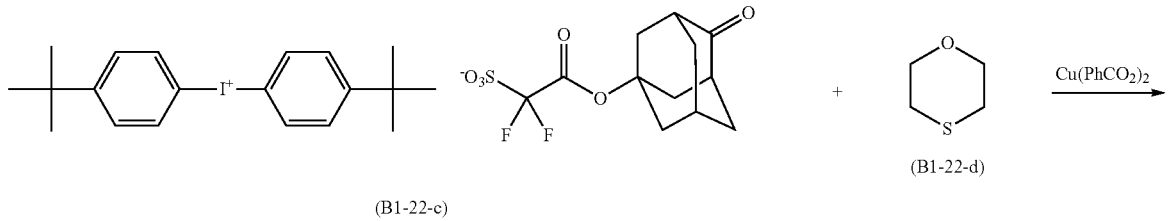

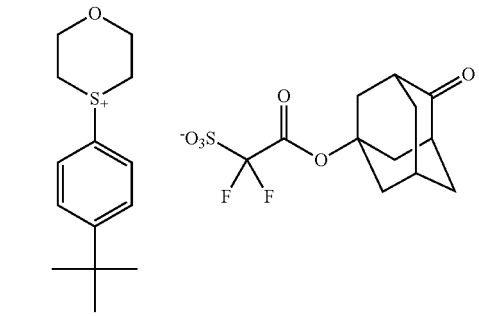

(B1-22)

In to a reactor, 11.71 parts of salt represented by formula (B1-22-c), 1.7 parts of compound represented by formula (B1-22-d) and 46.84 parts of monochlorobenzene were charged and stirred at 23° C. for 30 minutes. To the resulting mixture, 0.12 parts of dibenzoic acid copper (II) was added and the obtained mixture was stirred at 100° C. for 30 minutes. The reaction mixture was concentrated, and then 50 parts of chloroform and 12.5 parts of ion exchanged water were added to the obtained residues, and the obtained mixture was stirred at 23° C. for 30 minutes, followed by separating an organic layer to wash with water. 12.5 parts of ion exchanged water was added to the obtained organic layer and the obtained mixture was stirred at 23° C. for 30 minutes, followed by separating an organic layer to wash with water. The washing step with water was conducted eight times. Then the mixture was concentrated, and 50 parts of tert-butylmethylether were added thereto and the obtained mixture was stirred, followed by filtrating it, to provide 6.84 parts of salt represented by formula (B1-22).

MASS (ESI(+)Spectrum): M⁺ 237.1
MASS (ESI(−)Spectrum): M⁻ 323.0

Synthesis Examples of Resins

The monomers used for Synthesis Examples of the resins are illustrated below. These monomers are referred to as "monomer (X)" where "(X)" is the symbol of formula representing the structure of each monomer.

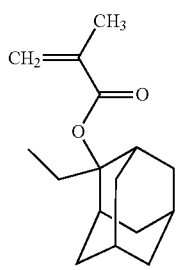

(a1-1-2)

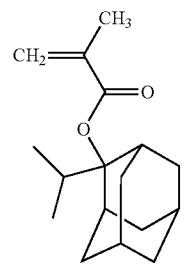

(a1-1-3)

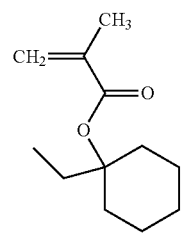

(a1-2-3)

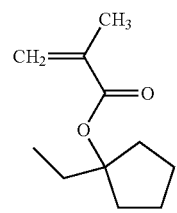

(a1-2-9)

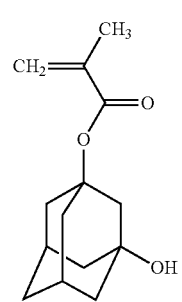

(a2-1-1)

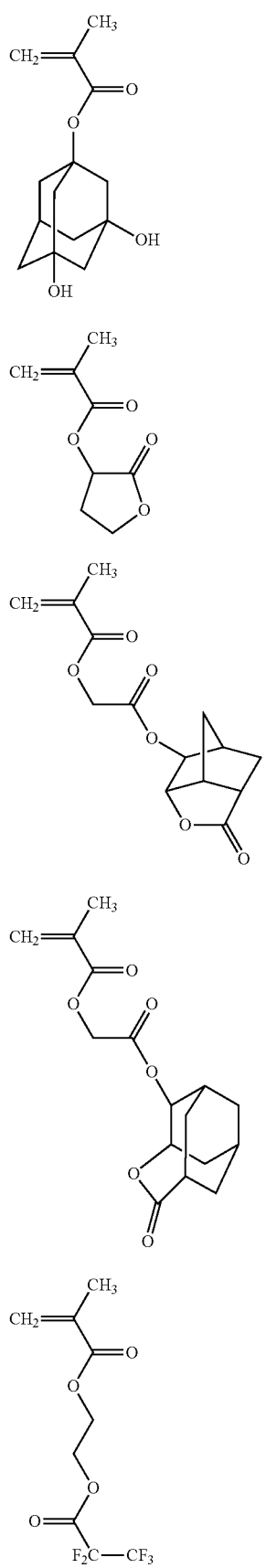
(a2-1-3)
(a3-1-1)
(a3-2-3)
(a3-4-2)
(a4-1-7)
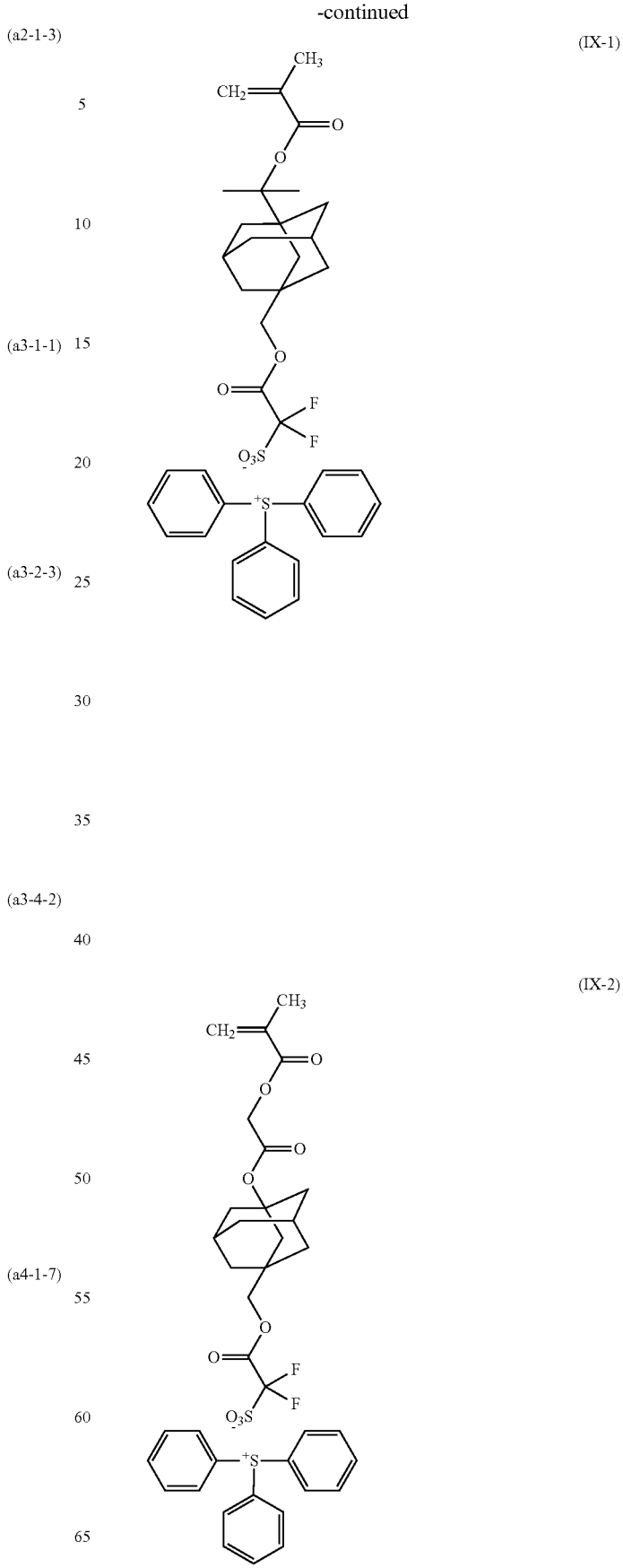
(IX-1)
(IX-2)

-continued (I-1)

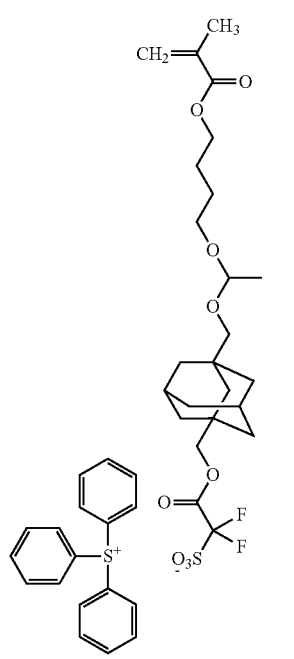

(I-2)

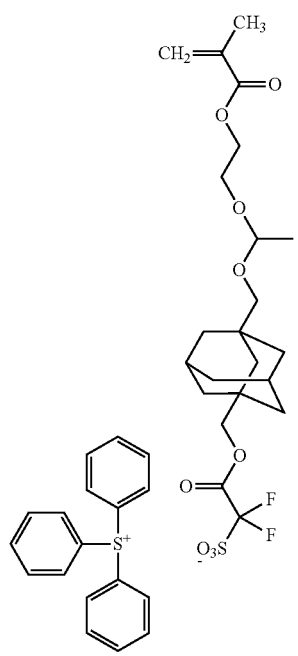

-continued (I-57)

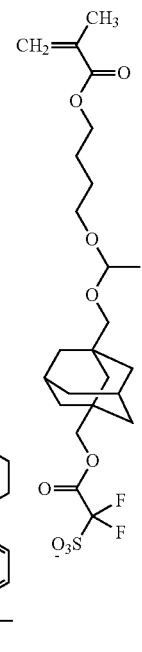

(I-71)

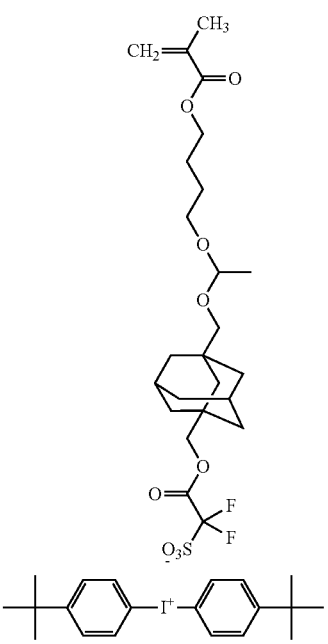

Example 5

Synthesis of Resin A1

Monomer (a1-1-2), monomer (a1-2-3), monomer (a2-1-1), monomer (a3-1-1), monomer (a3-2-3) and salt (I-1) were mixed together with the mole ratio of monomer (a1-1-2), monomer (a1-2-3), monomer (a2-1-1), monomer (a3-1-1), monomer (a3-2-3) and salt (I-1)=30:14:6:20:25:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 73° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 6800, in 77% yield. This resin, which had the structural units of the following formulae, was referred to as Resin A1.

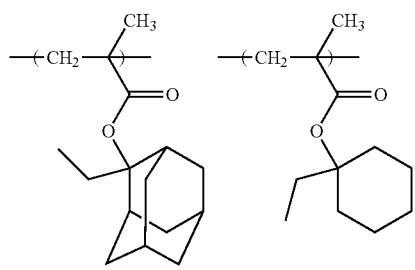

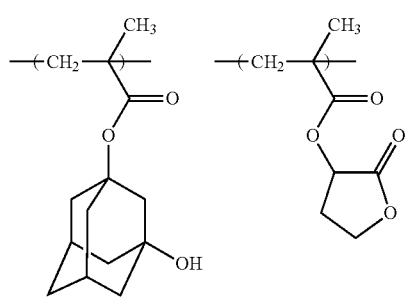

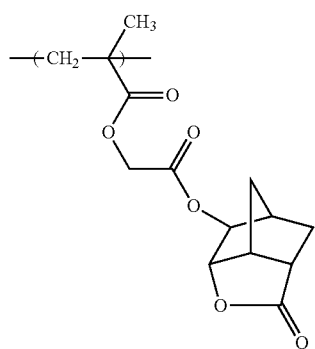

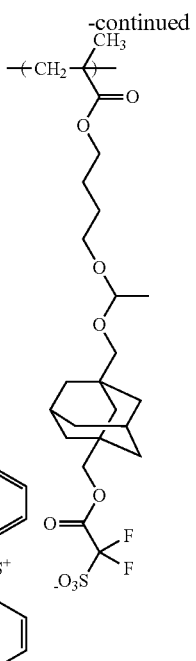

Example 6

Synthesis of Resin A2

Monomer (a1-1-3), monomer (a1-2-9), monomer (a2-1-3), monomer (a3-4-2) and salt (I-1) were mixed together with the mole ratio of monomer (a1-1-3), monomer (a1-2-9), monomer (a2-1-3), monomer (a3-4-2) and salt (I-1)=45:14:2.5:33.5:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 73° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 7300, in 58% yield. This resin, which had the structural units of the following formulae, was referred to as Resin A2.

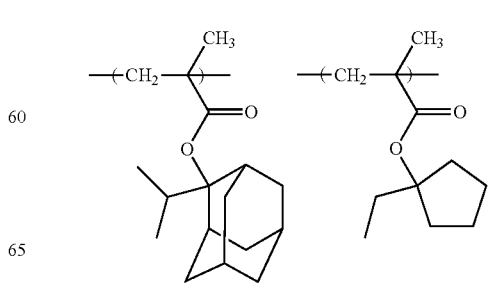

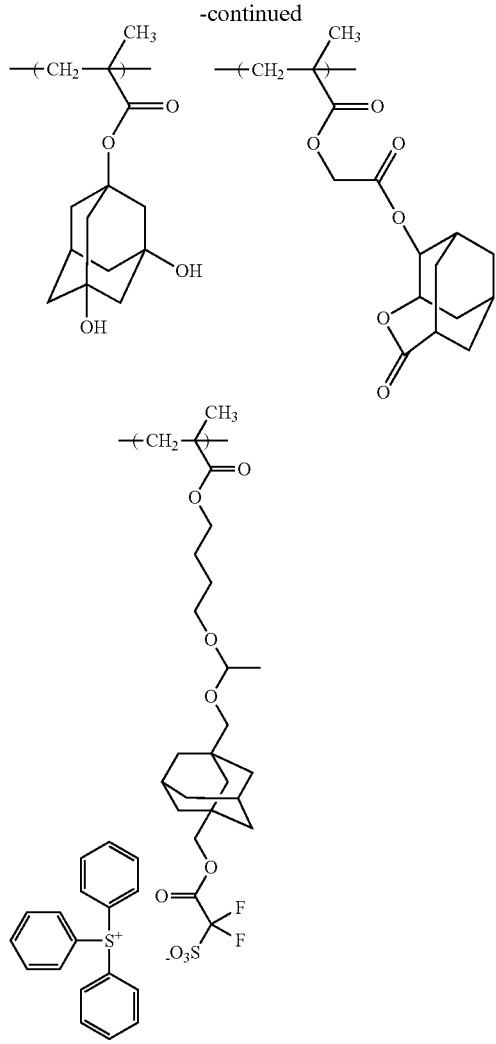

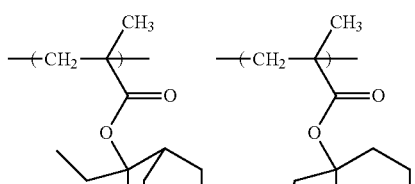
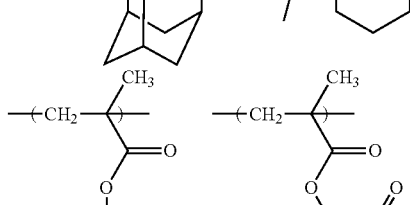
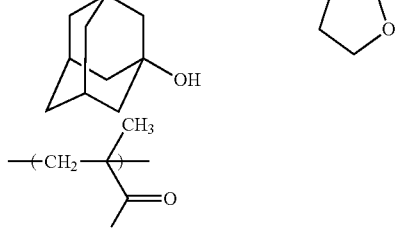
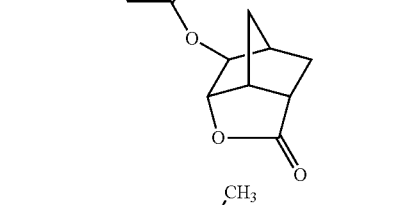
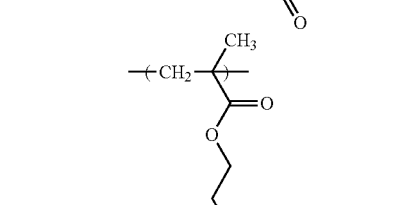
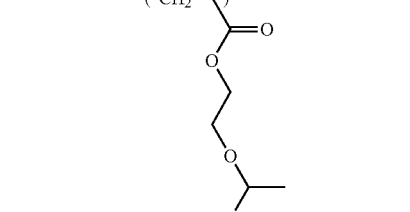
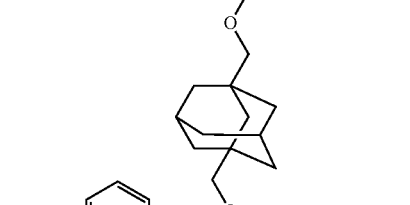
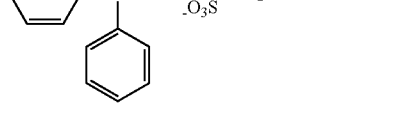

Example 7

Synthesis of Resin A3

Monomer (a1-1-2), monomer (a1-2-3), monomer (a2-1-1), monomer (a3-1-1), monomer (a3-2-3) and salt (I-2) were mixed together with the mole ratio of monomer (a1-1-2), monomer (a1-2-3), monomer (a2-1-1), monomer (a3-1-1), monomer (a3-2-3) and salt (I-2)=30:14:6:20:25:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 75° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 6500, in 75% yield. This resin, which had the structural units of the following formulae, was referred to as Resin A3.

Example 8

Synthesis of Resin A4

Monomer (a1-1-2), monomer (a1-2-3), monomer (a2-1-1), monomer (a3-1-1), monomer (a3-2-3) and salt (I-57)

were mixed together with the mole ratio of monomer (a1-1-2), monomer (a1-2-3), monomer (a2-1-1), monomer (a3-1-1), monomer (a3-2-3) and salt (I-57)=30:14:6:20:25:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 75° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 7100, in 76% yield. This resin, which had the structural units of the following formulae, was referred to as Resin A4.

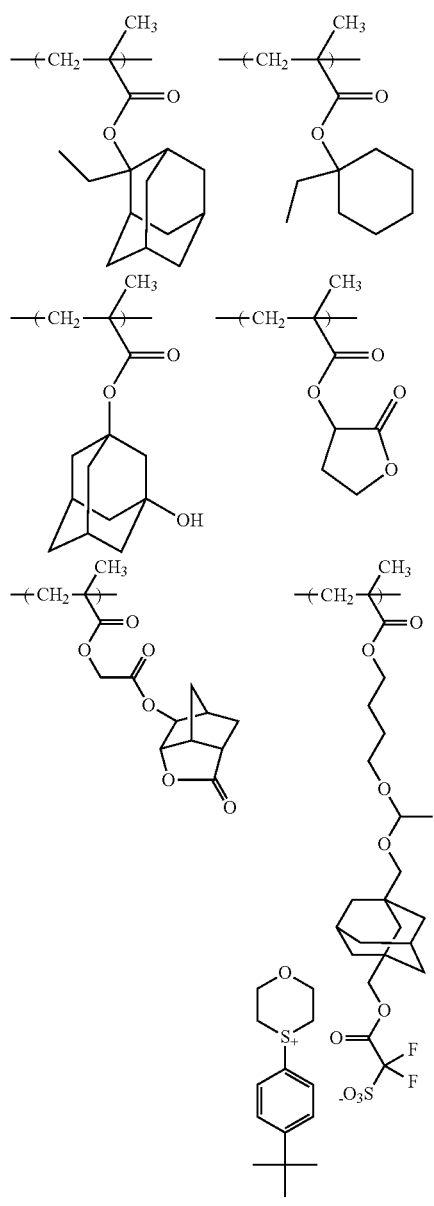

Example 9

Synthesis of Resin A5

Monomer (a1-1-2), monomer (a1-2-3), monomer (a2-1-1), monomer (a3-1-1), monomer (a3-2-3) and salt (I-71) were mixed together with the mole ratio of monomer (a1-1-2), monomer (a1-2-3), monomer (a2-1-1), monomer (a3-1-1), monomer (a3-2-3) and salt (I-71)=30:14:6:20:25:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 75° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 7500, in 68% yield. This resin, which had the structural units of the following formulae, was referred to as Resin A5.

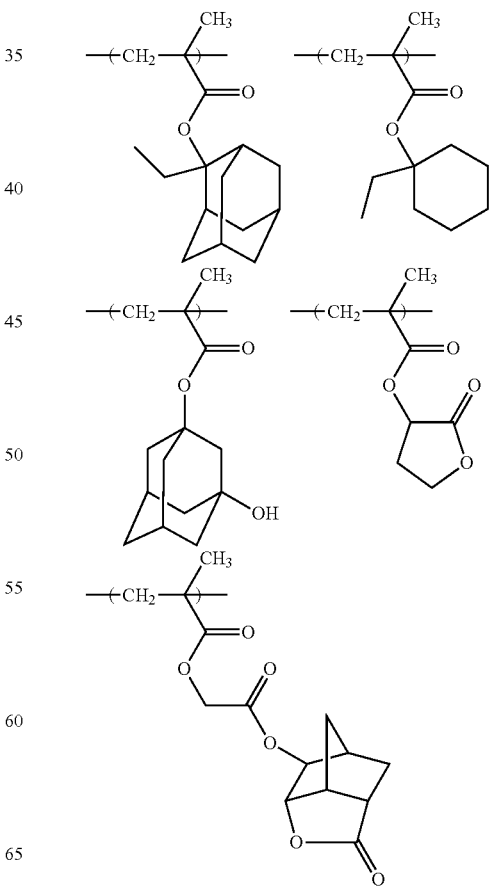

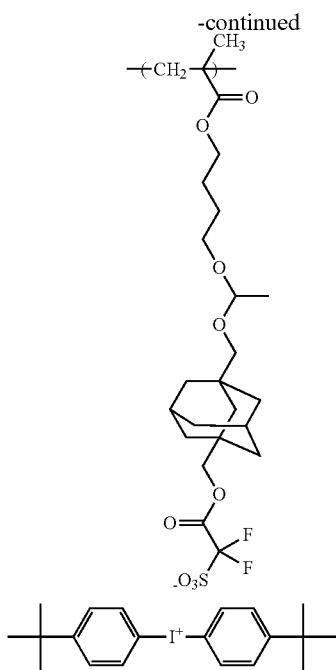

Example 10

Synthesis of Resin A6

Monomer (a1-1-3), monomer (a1-2-9), monomer (a2-1-3), monomer (a3-4-2) and salt (I-2) were mixed together with the mole ratio of monomer (a1-1-3), monomer (a1-2-9), monomer (a2-1-3), monomer (a3-4-2) and salt (I-2)=45:14:2.5:33.5:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 75° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 6900, in 62% yield. This resin, which had the structural units of the following formulae, was referred to as Resin A6.

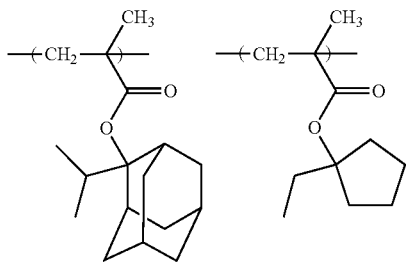

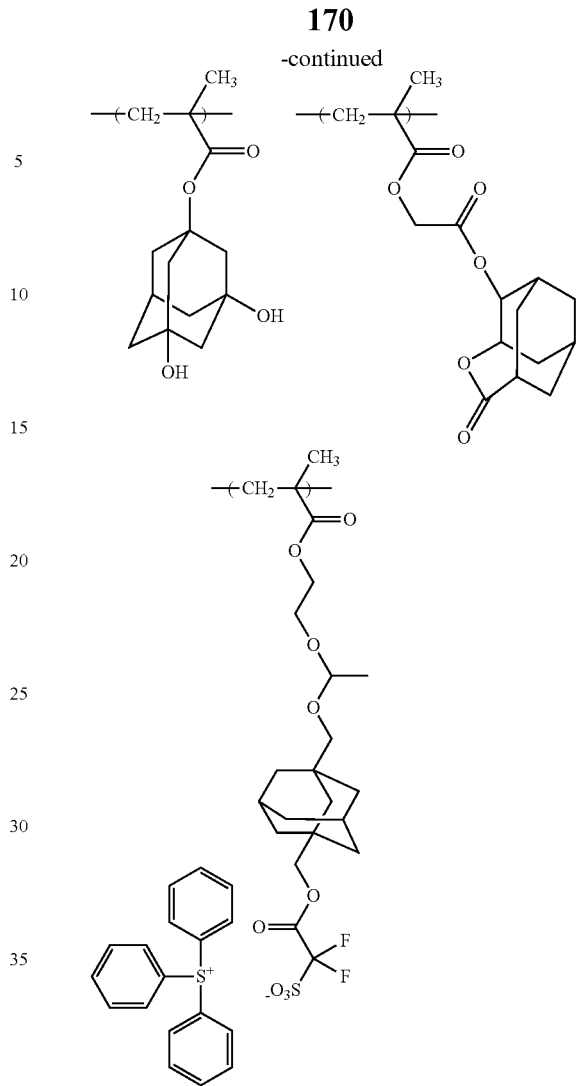

Example 11

Synthesis of Resin A7

Monomer (a1-1-3), monomer (a1-2-9), monomer (a2-1-3), monomer (a3-4-2) and salt (I-57) were mixed together with the mole ratio of monomer (a1-1-3), monomer (a1-2-9), monomer (a2-1-3), monomer (a3-4-2) and salt (I-57)=45:14:2.5:33.5:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 75° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 7000, in 60% yield. This resin, which had the structural units of the following formulae, was referred to as Resin A7.

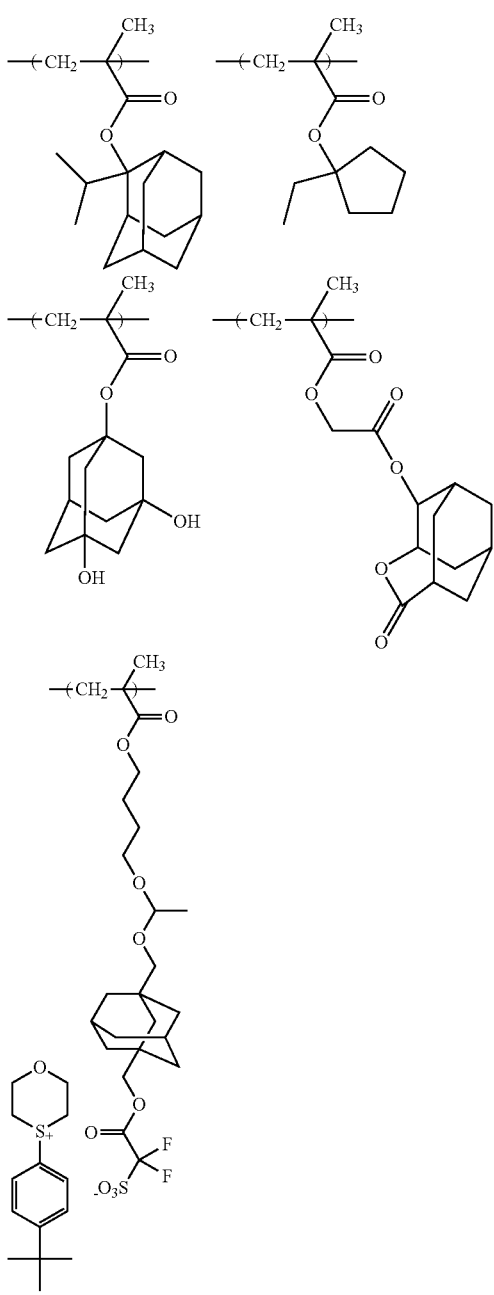

Example 12

Synthesis of Resin A8

Monomer (a1-1-3), monomer (a1-2-9), monomer (a2-1-3), monomer (a3-4-2) and salt (I-71) were mixed together with the mole ratio of monomer (a1-1-3), monomer (a1-2-9), monomer (a2-1-3), monomer (a3-4-2) and salt (I-71)=45:14:2.5:33.5:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 75° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 6900, in 55% yield. This resin, which had the structural units of the following formulae, was referred to as Resin A8.

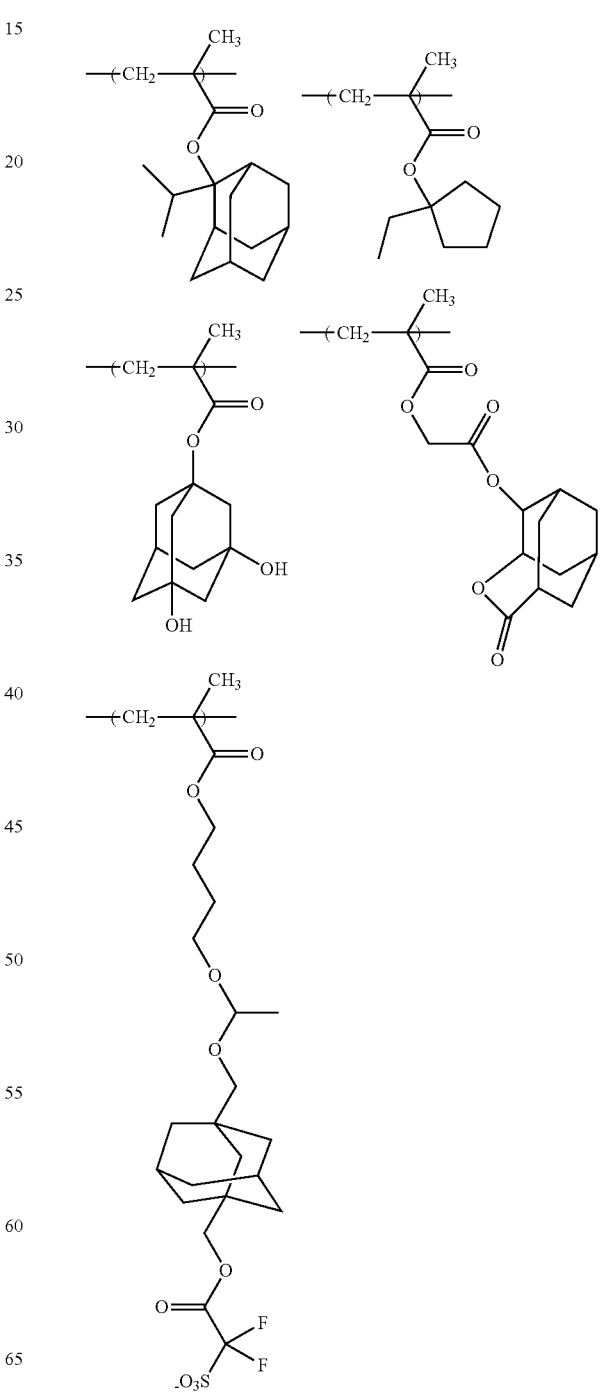

-continued

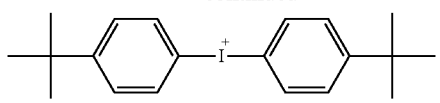

Synthesis Example 3

Synthesis of Resin AX1

Monomer (a1-1-2), monomer (a1-2-3), monomer (a2-1-1), monomer (a3-1-1), monomer (a3-2-3) and salt (IX-1) were mixed together with the mole ratio of monomer (a1-1-2), monomer (a1-2-3), monomer (a2-1-1), monomer (a3-1-1), monomer (a3-2-3) and salt (IX-1)=30:14:6:20:25:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 73° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 7000, in 71% yield. This resin, which had the structural units of the following formulae, was referred to as Resin AX1.

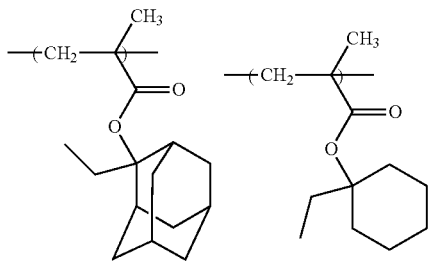

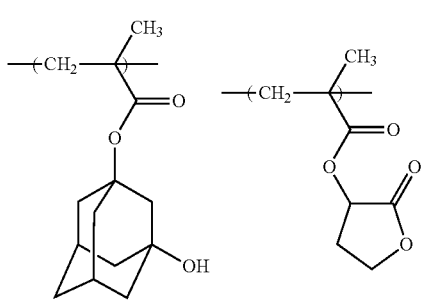

-continued

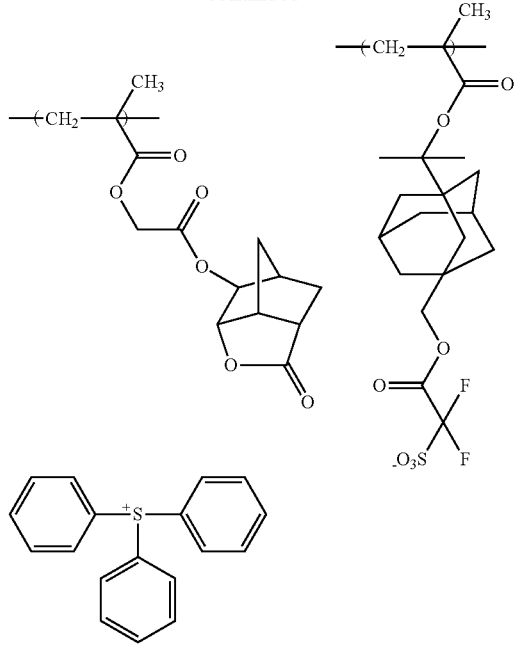

Synthesis Example 4

Synthesis of Resin AX2

Monomer (a1-1-2), monomer (a1-2-3), monomer (a2-1-1), monomer (a3-1-1), monomer (a3-2-3) and salt (IX-2) were mixed together with the mole ratio of monomer (a1-1-2), monomer (a1-2-3), monomer (a2-1-1), monomer (a3-1-1), monomer (a3-2-3) and salt (IX-2)=30:14:6:20:25:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 73° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 6900, in 76% yield. This resin, which had the structural units of the following formulae, was referred to as Resin AX2.

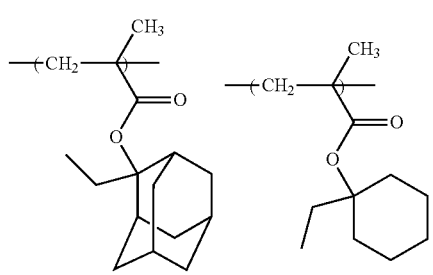

-continued

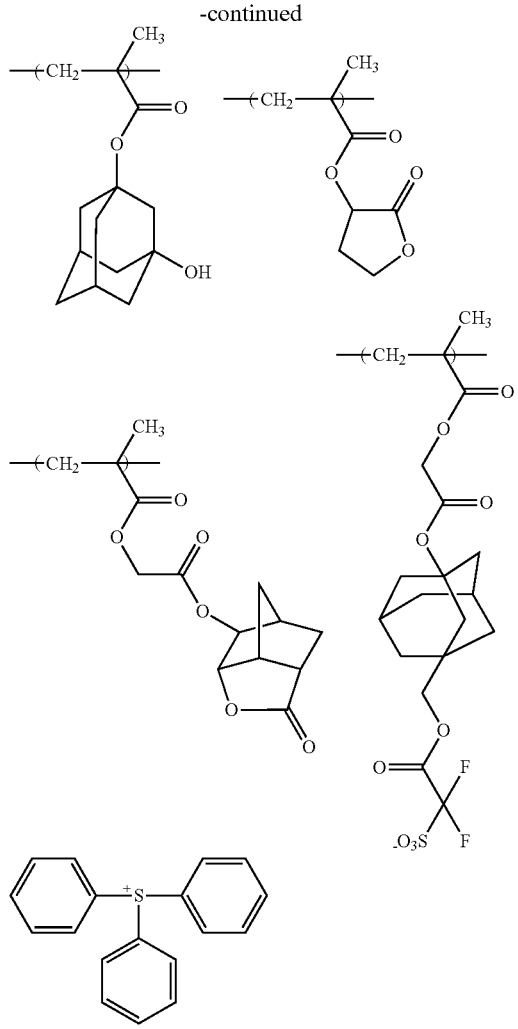

Synthesis Example 5

Synthesis of Resin AX3

Monomer (a1-1-3), monomer (a1-2-9), monomer (a2-1-3), monomer (a3-4-2) and salt (IX-1) were mixed together with the mole ratio of monomer (a1-1-3), monomer (a1-2-9), monomer (a2-1-3), monomer (a3-4-2) and salt (IX-1)=45:14:2.5:33.5:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 73° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate a resin. The obtained resin was filtrated to obtain the resin having a weight average molecular weight of about 7000, in 52% yield. This resin, which had the structural units of the following formulae, was referred to as Resin AX3.

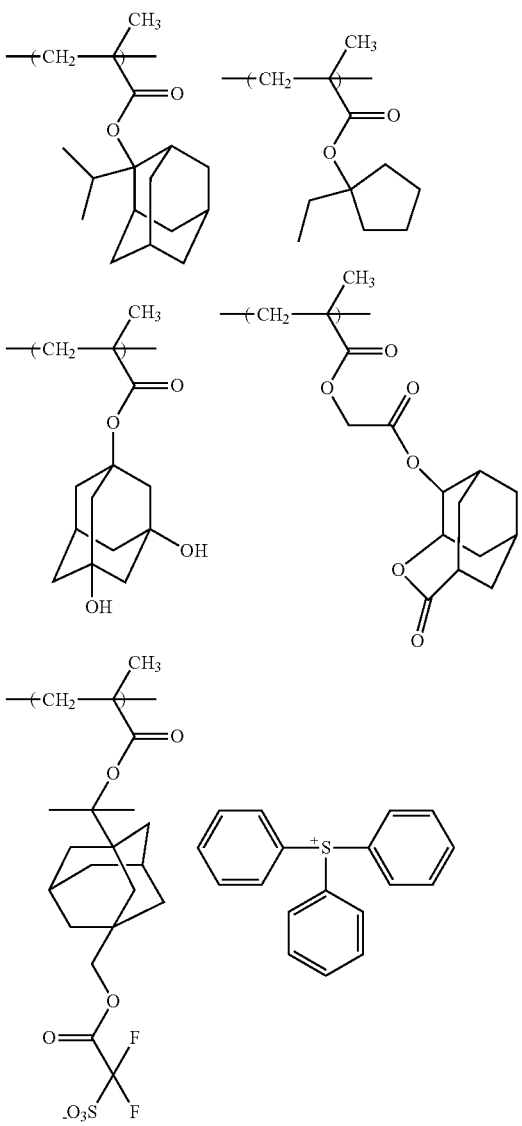

Synthesis Example 6

Synthesis of Resin AX4

Monomer (a1-1-3), monomer (a1-2-9), monomer (a2-1-3), monomer (a3-4-2) and salt (IX-2) were mixed together with the mole ratio of monomer (a1-1-3), monomer (a1-2-9), monomer (a2-1-3), monomer (a3-4-2) and salt (IX-2)=45:14:2.5:33.5:5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1.0% by mole and 3.0% by mole respectively with respect to the total amount of monomers, and the resultant mixture was heated at 73° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 7500, in 69% yield. This resin, which had the structural units of the following formulae, was referred to as Resin AX4.

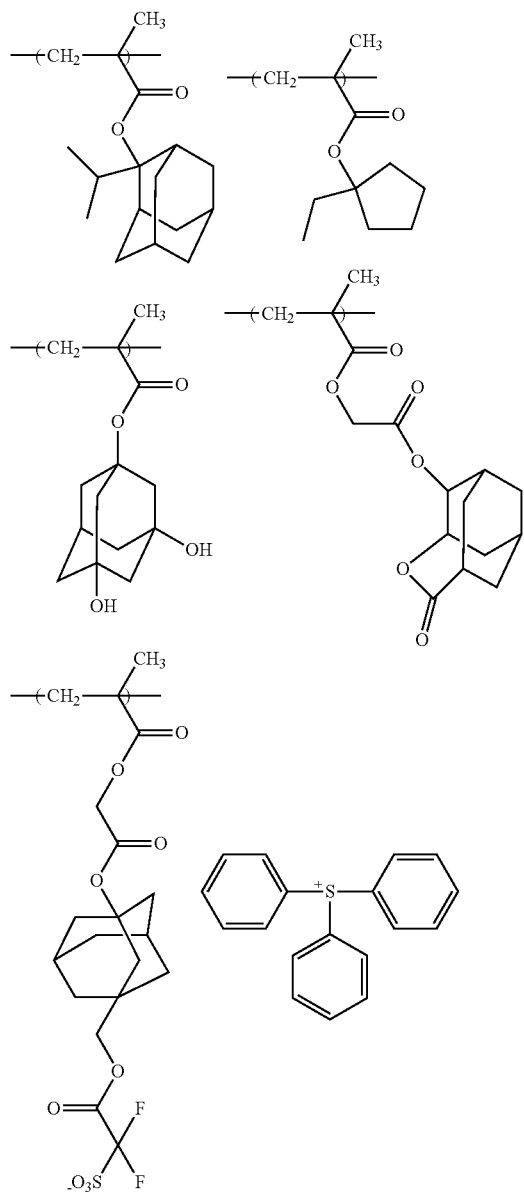

Synthesis Example 7

Synthesis of Resin AA1

Monomer (a1-1-2), monomer (a11-2-3), monomer (a2-1-1), monomer (a3-1-1) and monomer (a3-2-3) were mixed together with the mole ratio of monomer (a1-1-2), monomer (a1-2-3), monomer (a2-1-1), monomer (a3-1-1) and monomer (a3-2-3)=30:14:6:20:30, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated at 73° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 7800, in 76% yield. This resin, which had the structural units of the following formulae, was referred to as Resin AA1.

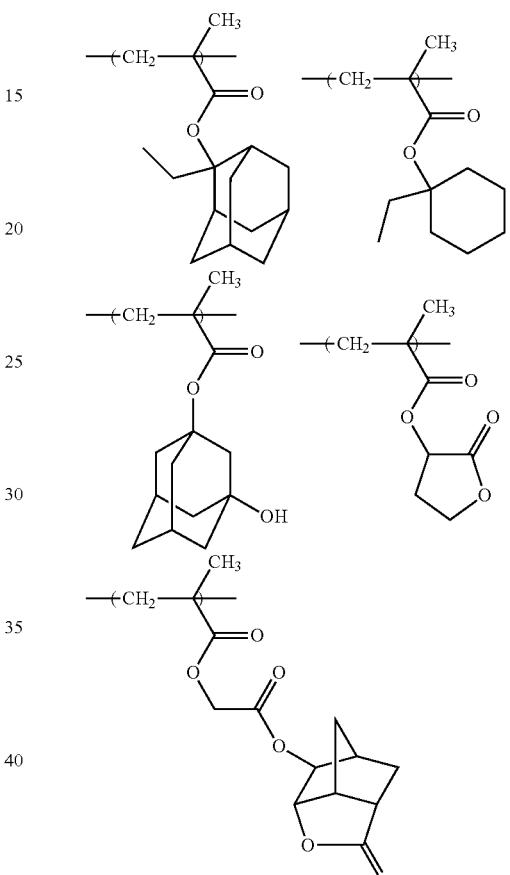

Synthesis Example 8

Synthesis of Resin AA2

Monomer (a1-1-3), monomer (a1-2-9), monomer (a2-1-3) and monomer (a3-4-2) were mixed together with the mole ratio of monomer (a1-1-3), monomer (a1-2-9), monomer (a2-1-3) and monomer (a3-4-2)=45:14:2.5:38.5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated at 73° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 7800, in 65% yield. This resin, which had the structural units of the following formulae, was referred to as Resin AA2.

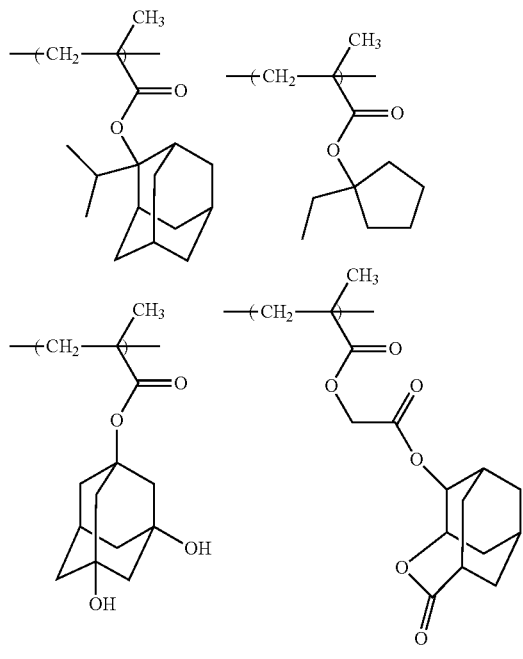

Synthesis Example 9

Synthesis of Resin X1

Monomer (a4-1-7) was used, and dioxane was added thereto in the amount equal to 1.2 times by mass of the total amount of the monomer to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated at 75° C. for about 5 hours. Then, the obtained reaction mixture was poured into a large amount of a mixture of methanol and water to precipitate a resin. The obtained resin was filtrated. Thus obtained resin was poured into a mixture of methanol and water to precipitate the resin. The obtained resin was filtrated to obtain the resin having a weight average molecular weight of about 17000, in 76% yield. This resin, which had the structural units of the following formula, was referred to as Resin X1.

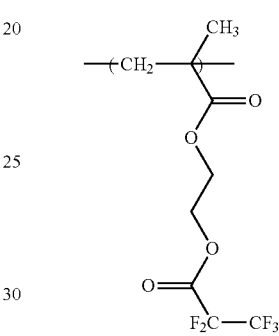

(Preparing Resist Composition)

Resist compositions were prepared by mixing and dissolving each of the components shown in Table 2, and then filtrating through a fluororesin filter having 0.2 μm pore diameter.

TABLE 2

| Resist Comp. | Resin (parts) | Acid Generator (B) (parts) | Salt (a) (parts) | Compound (D) | PB/PEB (° C./° C.) |
|---|---|---|---|---|---|
| Composition 1 | X1/AA1 = 0.4/10 | B1-21/B1-22 = 0.7/0.2 | I-1 = 0.4 | D1 = 0.28 | 110/95 |
| Composition 2 | X1/A1 = 0.4/10 | B1-21/B1-22 = 0.9/0.4 | — | D1 = 0.28 | 110/95 |
| Composition 3 | X1/A1 = 0.4/10 | B1-21/B1-22 = 0.3/0.1 | I-1 = 0.2 | D1 = 0.28 | 110/95 |
| Composition 4 | X1/A1 = 0.4/10 | — | I-1 = 0.3 | D1 = 0.28 | 110/95 |
| Composition 5 | X1/AA1 = 0.4/10 | — | I-1 = 0.9 | D1 = 0.28 | 110/95 |
| Composition 6 | X1/A2 = 0.4/10 | B1-21/B1-22 = 0.7/0.2 | I-1 = 0.4 | D1 = 0.28 | 100/85 |
| Composition 7 | X1/A2 = 0.4/10 | B1-21/B1-22 = 0.9/0.4 | — | D1 = 0.28 | 100/85 |
| Composition 8 | X1/A2 = 0.4/10 | B1-21/B1-22 = 0.3/0.1 | I-1 = 0.2 | D1 = 0.28 | 100/85 |
| Composition 9 | X1/A2 = 0.4/10 | — | I-1 = 0.3 | D1 = 0.28 | 100/85 |
| Composition 10 | X1/AA2 = 0.4/10 | — | I-1 = 0.9 | D1 = 0.28 | 100/85 |
| Composition 11 | X1/A3 = 0.4/10 | B1-21/B1-22 = 0.9/0.4 | — | D1 = 0.28 | 110/95 |
| Composition 12 | X1/A4 = 0.4/10 | B1-21/B1-22 = 0.9/0.4 | — | D1 = 0.28 | 110/95 |
| Composition 13 | X1/A5 = 0.4/10 | B1-21/B1-22 = 0.9/0.4 | — | D1 = 0.28 | 110/95 |
| Composition 14 | X1/A6 = 0.4/10 | B1-21/B1-22 = 0.9/0.4 | — | D1 = 0.28 | 100/85 |
| Composition 15 | X1/A7 = 0.4/10 | B1-21/B1-22 = 0.9/0.4 | — | D1 = 0.28 | 100/85 |
| Composition 16 | X1/A8 = 0.4/10 | B1-21/B1-22 = 0.9/0.4 | — | D1 = 0.28 | 100/85 |

TABLE 2-continued

| Resist Comp. | Resin (parts) | Acid Generator (B) (parts) | Salt (a) (parts) | Compound (D) | PB/PEB (° C./° C.) |
|---|---|---|---|---|---|
| Comp. Comp. 1 | X1/AX1 = 0.4/10 | — | IX-1 = 0.3 | D1 = 0.28 | 110/95 |
| Comp. Comp. 2 | X1/AA1 = 0.4/10 | — | IX-1 = 0.9 | D1 = 0.28 | 110/95 |
| Comp. Comp. 3 | X1/AX2 = 0.4/10 | — | IX-2 = 0.3 | D1 = 0.28 | 110/95 |
| Comp. Comp. 4 | X1/AA1 = 0.4/10 | — | IX-2 = 0.9 | D1 = 0.28 | 110/95 |
| Comp. Comp. 5 | X1/AX3 = 0.4/10 | — | IX-1 = 0.3 | D1 = 0.28 | 100/85 |
| Comp. Comp. 6 | X1/AA2 = 0.4/10 | — | IX-1 = 0.9 | D1 = 0.28 | 100/85 |
| Comp. Comp. 7 | X1/AX4 = 0.4/10 | — | IX-2 = 0.3 | D1 = 0.28 | 100/85 |
| Comp. Comp. 8 | X1/AA2 = 0.4/10 | — | IX-2 = 0.9 | D1 = 0.28 | 100/85 |

<Resin>
Resins: Resins A1 to A8, AX1 to AX4, AA1, AA2, and X1 prepared by Synthesis of Resin.
<Acid Generator (B)>
I-1: a salt represented by formula (I-1)
IX-1: a salt represented by formula (IX-1), which was prepared according to the method described in the Examples of JP2011-215619A
IX-2: a salt represented by formula (IX-2), which was prepared according to the method described in the Examples of JP2014-197168A
B1-21: a salt represented by formula (B1-21)
B1-22: a salt represented by formula (B1-22)
<Compound (D)>
D1: The following salt, which was a product of Tokyo Chemical Industry Co., LTD

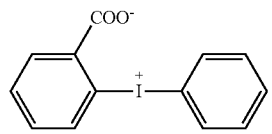

<Solvent of Resist Composition>

| Propyleneglycolmonomethylether acetate | 265 parts |
|---|---|
| Propyleneglycolmonomethylether | 20 parts |
| 2-Heptanone | 20 parts |
| γ-butyrolactone | 3.5 parts |

(Producing Resist Patterns)
A composition for an organic antireflective film ("ARC-29", by Nissan Chemical Co. Ltd.) was applied onto 12-inch silicon wafer and baked for 60 seconds at 205° C. to form a 78 nm thick organic antireflective film.

One of the resist compositions was then applied thereon by spin coating in such a manner that the thickness of the film after drying (pre-baking) became 85 nm.

The obtained wafer was then pre-baked for 60 sec on a direct hot plate at the temperature given in the "PB" column in Table 2.

On the wafers on which the resist film had thus been formed, the film was then exposed through a mask for forming line and space patterns with changing exposure quantity stepwise, by using an ArF excimer laser stepper for immersion lithography ("XT:1900Gi" by ASML Ltd.: NA=1.35, 3/5 Annular XY-pol.). Ultrapure water was used for medium of immersion.

After the exposure, post-exposure baking was carried out for 60 seconds at the temperature given in the "PEB" column in Table 2.

Then, development was carried out with 2.38% by mass of aqueous tetramethylammonium hydroxide solution for 60 seconds in the manner of paddle method to obtain resist patterns.

Effective sensitivity was represented as the exposure quantity at which a resist pattern of 50 nm line and space pattern was obtained with 1:1 line and space pattern.
(Line Edge Roughness (LER) Evaluation)
Irregularities in each wall surface of the obtained resist patterns were observed using a scanning electron microscope and measured the maximum width (nm) of the irregularities.
Table 3 illustrates the results thereof.

TABLE 3

|  | Resist Composition | LER |
|---|---|---|
| Ex. 13 | Composition 1 | 3.42 |
| Ex. 14 | Composition 2 | 3.28 |
| Ex. 15 | Composition 3 | 3.30 |
| Ex. 16 | Composition 4 | 3.33 |
| Ex. 17 | Composition 5 | 3.48 |
| Ex. 18 | Composition 11 | 3.32 |
| Ex. 19 | Composition 12 | 3.22 |
| Ex. 20 | Composition 13 | 3.48 |
| Comparative Ex. 1 | Comparative Comp. 1 | 4.24 |
| Comparative Ex. 2 | Comparative Comp. 2 | 4.78 |
| Comparative Ex. 3 | Comparative Comp. 3 | 4.68 |
| Comparative Ex. 4 | Comparative Comp. 4 | 4.74 |

(Producing Negative Resist Patterns)
A composition for an organic antireflective film ("ARC-29", by Nissan Chemical Co. Ltd.) was applied onto 12-inch silicon wafer and baked for 60 seconds at 205° C. to form a 78 nm thick organic antireflective film.

One of the resist compositions was then applied thereon by spin coating in such a manner that the thickness of the film after drying (pre-baking) became 100 nm.

The obtained wafer was then pre-baked for 60 sec on a direct hot plate at the temperature given in the "PB" column in Table 2.

On the wafers on which the resist film had thus been formed, the film was then exposed through a mask for forming trench patterns (pitch 120 nm/trench width 40 nm) with changing exposure quantity stepwise, by using an ArF excimer laser stepper for liquid-immersion lithography ("XT:1900Gi" by ASML Ltd.: NA=1.35, Annular σout=0.85 σin=0.65 XY-pol.). Ultrapure water was used for medium of liquid-immersion.

After the exposure, post-exposure baking was carried out for 60 seconds at the temperature given in the "PEB" column in Table 2.

Then, development was carried out with butyl acetate (a product of Tokyo Chemical Industry Co., LTD) at 23° C. for 20 seconds in the manner of dynamic dispensing method to obtain negative resist patterns.

Effective sensitivity was represented as the exposure quantity at which a resist pattern with 40 nm trench width was obtained.

(Line Edge Roughness (LER) Evaluation)

Irregularities in each wall surface of the obtained resist patterns were observed using a scanning electron microscope and measured the maximum width (nm) of the irregularities.

Table 4 illustrates the results thereof.

TABLE 4

|  | Resist Composition | LER (nm) |
|---|---|---|
| Ex. 21 | Composition 6 | 2.92 |
| Ex. 22 | Composition 7 | 2.76 |
| Ex. 23 | Composition 8 | 2.79 |
| Ex. 24 | Composition 9 | 2.82 |
| Ex. 25 | Composition 10 | 2.98 |
| Ex. 26 | Composition 14 | 2.78 |
| Ex. 27 | Composition 15 | 2.69 |
| Ex. 28 | Composition 16 | 2.81 |
| Comparative Ex. 5 | Comp. Comp. 5 | 3.34 |
| Comparative Ex. 6 | Comp. Comp. 6 | 3.88 |
| Comparative Ex. 7 | Comp. Comp. 7 | 3.58 |
| Comparative Ex. 8 | Comp. Comp. 8 | 3.78 |

The salt (I) can be used for an acid generator and/or a resin for a resist composition which is capable of providing a resist film with less line edge roughness (LER) and useful to a fine processing to semiconductors.

What is claimed is:

1. A resin comprising a structural unit derived from a salt represented by formula (I):

$$Z^+ \ ^-O_3S-\left[\left(\begin{array}{c}Q^1\\Q^2\end{array}\right)\left(\begin{array}{c}R^1\\R^2\end{array}\right)_z\right]-X^1-A^1-O-\underset{R^4}{\overset{R^3}{C}}-O-A^2-O-\underset{O}{\overset{}{C}}(=O)-C(=CH_2)R^5$$

wherein $Q^1$ and $Q^2$ independently represent a fluorine atom or a $C_1$ to $C_6$ perfluoroalkyl group,
$R^1$ and $R^2$ in each occurrence independently represent a hydrogen atom, a fluorine atom or a $C_1$ to $C_6$ perfluoroalkyl group,
z represents an integer of 0 to 6,
$X^1$ represents *—CO—O—, *—O—CO— or —O—, * represents a binding position to $C(R^1)(R^2)$ or $C(Q^1)(Q^2)$,
$A^1$ represents a $C_4$ to $C_{24}$ hydrocarbon group having a $C_4$ to $C_{18}$ divalent alicyclic hydrocarbon moiety,
$A^2$ represents a $C_2$ to $C_6$ alkanediyl group,
$R^3$ represents a $C_1$ to $C_6$ monovalent saturated hydrocarbon group,
$R^4$ represents a hydrogen atom or represents a $C_1$ to $C_6$ monovalent saturated hydrocarbon group,
$R^5$ represents a hydrogen atom, a fluorine atom, or a $C_1$ to $C_6$ alkyl group where a hydrogen atom may be replaced by a fluorine atom, and
$Z^+$ represents an organic cation.

2. The resin according to claim 1, further comprising a structural unit having an acid-labile group, which structural unit being different from the structural unit derived from the salt represented by formula (I).

3. The resin according to claim 2, wherein the structural unit having an acid-labile group is at least one selected from the group consisting of a structural unit represented by formula (a1-1) and a structural unit represented by formula (a1-2):

$$\text{(a1-1)}$$

$$\text{(a1-2)}$$

wherein $L^{a1}$ and $L^{a2}$ independently represent —O— or *—O—$(CH_2)_{k1}$—CO—O—,
k1 represents an integer of 1 to 7,
* represents a binding position to —CO—,
$R^{a4}$ and $R^{a5}$ independently represent a hydrogen atom or a methyl group,
$R^{a6}$ and $R^{a7}$ independently represent a $C_1$ to $C_8$ alkyl group, a $C_3$ to $C_{18}$ alicyclic hydrocarbon group or a combination thereof,
m1 represents an integer of 0 to 14,
n1 represents an integer of 0 to 10, and
n1' represents an integer of 0 to 3.

4. A resist composition comprising the resin according to claim 1 and an acid generator.

5. The resist composition according to claim 4, wherein the acid generator comprises a salt represented by formula (I):

$$Z^+ \ ^-O_3S-\left[\left(\begin{array}{c}Q^1\\Q^2\end{array}\right)\left(\begin{array}{c}R^1\\R^2\end{array}\right)_z\right]-X^1-A^1-O-\underset{R^4}{\overset{R^3}{C}}-O-A^2-O-\underset{O}{\overset{}{C}}(=O)-C(=CH_2)R^5$$

wherein $Q^1$ and $Q^2$ independently represent a fluorine atom or a $C_1$ to $C_6$ perfluoroalkyl group,
$R^1$ and $R^2$ in each occurrence independently represent a hydrogen atom, a fluorine atom or a $C_1$ to $C_6$ perfluoroalkyl group,
z represents an integer of 0 to 6,
$X^1$ represents *—CO—O—, *—O—CO— or —O—, * represents a binding position to $C(R^1)(R^2)$ or $C(Q^1)(Q^2)$, $A^1$ represents a $C_4$ to $C_{24}$ hydrocarbon group having a $C_4$ to $C_{18}$ divalent alicyclic hydrocarbon moiety, $A^2$ represents a $C_2$ to $C_6$ alkanediyl group, $R^3$ and $R^4$ independently represent a hydrogen atom or a $C_1$ to $C_6$ monovalent saturated hydrocarbon group, $R^5$ represents a hydrogen atom, a fluorine atom, or a $C_1$ to $C_6$ alkyl group where a hydrogen atom may be replaced by a fluorine atom, and $Z^+$ represents an organic cation.

6. The resist composition according to claim 4, wherein the acid generator further comprising a salt represented by formula (B1):

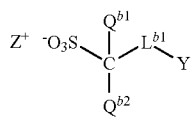

(B1)

wherein $Q^{b1}$ and $Q^{b2}$ respectively represent a fluorine atom or a $C_1$ to $C_6$ perfluoroalkyl group, $L^{b1}$ represents a $C_1$ to $C_{24}$ divalent saturated hydrocarbon group where a methylene group may be replaced by an oxygen atom or a carbonyl group and where a hydrogen atom may be replaced by a hydroxyl group or fluorine atom, and Y represents an optionally substituted methyl group, or an optionally substituted $C_3$ to $C_{18}$ alicyclic hydrocarbon group where a methylene group may be replaced by an oxygen atom, a carbonyl group or a sulfonyl group, and $Z^+$ represents an organic cation.

7. The resist composition according to claim 4 further comprising a salt which generates an acid lower in acidity than an acid generated from the acid generator.

* * * * *